US012708662B2

(12) United States Patent
Xu et al.

(10) Patent No.: US 12,708,662 B2
(45) Date of Patent: Aug. 18, 2026

(54) MONOCLONAL ANTIBODY AGAINST HUMAN ACTIVATED PROTEIN C AND PREPARATION AND USE THEREOF

(71) Applicant: OKLAHOMA MEDICAL RESEARCH FOUNDATION, Oklahoma City, OK (US)

(72) Inventors: Jun Xu, Shanghai (CN); Lu Cheng, Shanghai (CN); Jiawei Yi, Shanghai (CN); Zhisong Xia, Shanghai (CN); Yeheng Liu, Shanghai (CN)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 170 days.

(21) Appl. No.: 17/921,616

(22) PCT Filed: Jul. 28, 2021

(86) PCT No.: PCT/CN2021/108933

§ 371 (c)(1),
(2) Date: Oct. 26, 2022

(87) PCT Pub. No.: WO2023/284012

PCT Pub. Date: Jan. 19, 2023

(65) Prior Publication Data

US 2025/0277057 A1 Sep. 4, 2025

(30) Foreign Application Priority Data

Jul. 13, 2021 (CN) ........................ 202110791310.X

(51) Int. Cl.

*C07K 16/40* (2006.01)
*A61K 39/00* (2006.01)
*A61P 7/04* (2006.01)
*C07K 16/36* (2006.01)

(52) U.S. Cl.

CPC ................ *A61K 39/00* (2013.01); *A61P 7/04* (2018.01); *C07K 16/36* (2013.01); *A61K 2039/505* (2013.01); *C07K 2317/24* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 8,153,766 B2 * | 4/2012 | Xu | .......................... | C07K 16/40 530/387.3 |
| 9,657,111 B2 * | 5/2017 | Zhao | .................... | G01N 33/573 |
| 2015/0307625 A1 | 10/2015 | Zhao et al. | | |
| 2018/0326053 A1 | 11/2018 | Zhao et al. | | |

FOREIGN PATENT DOCUMENTS

| | | | | |
|---|---|---|---|---|
| WO | WO2009055669 A2 | 4/2009 | | |
| WO | WO-2014085527 A1 * | 6/2014 | ................ | A61P 7/00 |
| WO | WO2015179435 A1 | 11/2015 | | |

OTHER PUBLICATIONS

Janeway et al., Immunobiology, 3rd edition, Garland Publishing Inc., 1997, pp. 3:1-3:11.*
Rudikoff et al., Proc Natl Acad Sci U S A. Mar. 1982;79(6):1979-83. doi: 10.1073/pnas.79.6.1979. PMID: 6804947.*
Edwards et al., J Mol Biol. Nov. 14, 2003;334(1):103-18. doi: 10.1016/j.jmb.2003.09.054. PMID: 14596803.*
Llyod et al., Protein Eng Des Sel. Mar. 2009;22(3):159-68. doi: 10.1093/protein/gzn058. Epub Oct. 29, 2008. PMID: 18974080.*
Goel et al., J Immunol. Dec. 15, 2004; 173(12):7358-67 PMID: 15585860 DOI: 10.4049/jimmunol.173.12.7358.*
Lescar et al., J Biol Chem. Jul. 28, 1995;270(30):18067-76. doi: 10.1074/jbc.270.30.18067. PMID: 7629116.*
Kanyavuz et al., Nat Rev Immunol. Jun. 2019;19(6):355-368. doi: 10.1038/S41577-019-0126-7. PMID: 30718829.*
Kipriyanov et al., Mol Biotechnol. Jan. 2004;26(1):39-60. doi: 10.1385/MB:26:1:39. PMID: 14734823.*
Dondelinger et al., Front Immunol. Oct. 16, 2018:9:2278. doi: 10.3389/fimmu.2018.02278. eCollection 2018. PMID: 30386328 PMCID: PMC6198058.*

* cited by examiner

*Primary Examiner* — Michael Szperka
(74) *Attorney, Agent, or Firm* — IPRTOP LLC

(57) ABSTRACT

The present disclosure belongs to the technical field of monoclonal antibodies, and relates to a monoclonal antibody against activated protein C (aPC). Amino acid sequences of a heavy chain and a light chain of the monoclonal antibody are shown in SEQ ID NOs: 5-26, and CDR sequences are shown in SEQ ID NOs: 27-92. The present disclosure further provides a biological material related to the monoclonal antibody, and the monoclonal antibody is capable of selectively binding to aPC rather than unactivated protein C. The present disclosure further provides use of the monoclonal antibody and the related biological material in preparation of a drug for treatment of coagulation deficiency or defect disorders and a related treatment method, which have broad application prospects.

13 Claims, 18 Drawing Sheets

Specification includes a Sequence Listing.

| | EC50 |
|---|---|
| Humab001-1 | 0.5706 |
| Humab001-2 | 0.7343 |
| Humab001-3 | 0.6171 |
| Humab001-4 | 0.7405 |
| Humab001-5 | 0.4888 |
| Humab001-6 | 0.4179 |
| Humab001-7 | 0.4211 |
| Humab001-8 | 0.5803 |

| | EC50 |
|---|---|
| Humab001-9 | 1.550 |
| Humab001-10 | 1.114 |
| Humab001-11 | 1.032 |
| Humab001-12 | 0.8173 |
| Humab001-13 | 0.1991 |
| Humab001-14 | 0.2495 |
| Humab001-15 | 0.2459 |
| Humab001-16 | 0.1723 |

Elisa binding of antibodies to APC
(coating 1ug/ml)

| | EC50 |
|---|---|
| Humab001-17 | 0.3059 |
| Humab001-18 | 0.3392 |
| Humab001-19 | 0.2591 |
| Humab001-20 | 0.2164 |
| Humab001-21 | 0.5604 |
| Humab001-22 | 0.3682 |
| Humab001-23 | 0.2803 |
| Humab001-24 | 0.3870 |

Elisa binding of antibodies to APC
(coating 1ug/ml)

Humab001-25
Humab001-26
Humab001-27
Humab001-28
3657 PC mAb
30120-mAb001× hIgG1
hIgG

| | EC50 |
|---|---|
| Humab001-25 | 0.6980 |
| Humab001-26 | 0.5963 |
| Humab001-27 | 0.3700 |
| Humab001-28 | 0.4157 |
| 3657 PC mAb | 0.4029 |
| 30120-mAb001×hIgG1 | 0.1674 |

Sample ID: APC; Loading Sample ID: HAPC14-7 nm 0.6
0.4
0.2
0

0 100 200 300 400 500

Time (sec)

MONOCLONAL ANTIBODY AGAINST HUMAN ACTIVATED PROTEIN C AND PREPARATION AND USE THEREOF

CROSS REFERENCE TO RELATED PATENT APPLICATION

The present application is the US national stage of PCT/CN2021/108933 filed on 2021 Jul. 28, which claims the priority of the Chinese patent application No. 202110791310.X filed on 2021 Jul. 13, which application is incorporated herein by reference.

INCORPORATION BY REFERENCE

The Sequence Listing associated with this application is filed in ASCII text format via the USPTO patent electronic filing system and is incorporated herein by reference in its entirety. The ASCII text file is named 220391-sequence.txt, created on Jan. 5, 2026, and is 43,306 bytes in size.

BACKGROUND OF THE PRESENT DISCLOSURE

Field of Disclosure

The present disclosure belongs to the technical field of monoclonal antibodies, and relates to a monoclonal antibody against human activated protein C (aPC) and use thereof.

Description of Related Arts

Protein C (PC) pathways play a crucial role in regulating coagulation and inflammation. Thrombin forms a complex with thrombomodulin (TM) on vascular endothelial cells, thereby activating protein C. Activated protein C (aPC) cleaves activated factor V and factor VIII, thereby negatively downregulating formation of thrombin and maintaining the balance between thrombosis and hemostasis in vivo. aPC protects animals against disoperation of endotoxin (LPS) or *Escherichia coli*. Recombinant human aPC products were approved by FDA as the first drug for treating severe sepsis. At present, the molecular mechanisms of aPC for anti-inflammatory and cytoprotective effects are not yet well understood. Studies on mutations showed that the anticoagulant activity of aPC is obviously not necessary for the antiapoptotic effect of aPC on endothelial cells. Vascular endothelial protein C receptors (EPCRs) are mainly expressed on the endothelium of large vessels, and promote activation of protein C through the thrombin-TM complex. Recently, it has been demonstrated that aPC bound to EPCR may cleave PAR-1 on endothelial cells. Moreover, this study shows that all anti-inflammatory and antiapoptotic effects of aPC signaling are mediated by PAR-1 in endothelial cells. However, under the attack of lethal dose of LPS, the phenotype of PAR-1-deficient mice was similar to that of wild-type control mice, which indicated that PAR-1 might not be the only participant in the regulation of inflammation and apoptosis by aPC signaling.

In view of the key role of aPC in regulating pathophysiological functions in vivo, a monoclonal antibody HAPC1573 has been produced. This antibody specifically recognizes the activated form of human protein C (aPC) rather than protein C (Xu, U.S. Pat. Nos. 8,153,766B2, 9,127,072B2). This antibody alters the amidolytic activity of aPC on chromogenic peptide substrates and blocks the anticoagulant activity of aPC in plasma. More importantly, this antibody does not affect the cleavage of extracellular histones H3 and H4 by aPC, nor the cytoprotective activity of aPC on thrombin-induced permeability of endothelial cells. MAPC1591 is an anti-mouse aPC monoclonal antibody having similar functions to HAPC1573. MAPC1591 can block the anticoagulant activity of aPC in mice and maintain the cytoprotective activity of aPC, and thus protecting people with hemophilia A from traumatic hemorrhage. This indicates that the anti-aPC antibody can be applied to clinical settings such as hemophilia, trauma and sepsis.

Zhao et al. reported CDR sequences of HAPC1573 and humanized HAPC1573 against only anticoagulant activity rather than other activities of aPC. These CDR sequences showed an in vivo protective effect against bleeding in a monkey model of acute acquired hemophilia A (Zhao, U.S. Pat. No. 9,657,111B2, WO2017/087391A1, Nat. Communications 2020). The X-ray crystal structure of the aPC-humanized HAPC1573 Fab complex indicates that HAPC 1573 may not bind to the active site of aPC, but bind to an aPC autolysis loop containing the known aPC-FVa binding site. Therefore, humanized HAPC1573 may inhibit the anticoagulant function of aPC by interfering with the interaction between aPC and FVa. The inhibitory effect of humanized HAPC1573 is only limited to the anticoagulant activity of aPC, but does not affect its cytoprotective, anti-inflammatory and cell signaling functions. It is reported that the aPC concentration in human plasma is about 40 pm, and according to a surface plasmon resonance-based assay, the affinity of humanized HAPC 1573 to aPC is 10 nM. The concentration-dependent effect of HAPC 1573 in shortening prolonged APTT in human FVIII-deficient plasma and human FIX-deficient plasma was demonstrated in a Protac-dependent APTT coagulation assay. Even at the concentration of 50 μg/ml, HAPC 1573 still could not achieve the maximum inhibitory effect on the anticoagulant activity of aPC in this in vitro experiment. This observation was consistent with the in vivo observation of humanized HAPC 1573 in the monkey model of acute acquired hemophilia. In animal studies, it was found that only HAPC1573 at high doses of 10 mg/kg and 30 mg/kg could provide great protective effect. However, such high doses are not suitable for clinical use, so humanized HAPC 1573 with higher affinity is the prerequisite and guarantee for the potential use of aPC in treatment in the future.

SUMMARY OF THE PRESENT DISCLOSURE

One aspect of the present disclosure provides an anti-aPC monoclonal antibody. The anti-aPC monoclonal antibody includes an original antibody and a mutant antibody obtained by mutating one or more of the following 6 mutation sites in the original antibody.

The original antibody includes:

(a) a heavy chain CDR represented by any one or more of SEQ ID NOs: 27, 28 and 29; and/or (b) a light chain CDR represented by any one or more of SEQ ID NOs: 30, 31 and 32.

The 6 mutant sites are:

1) N57R/W located in VL CDR2;
2) E59G/P located in VL CDR2;
3) Q93V located in VL CDR3;
4) N31F located in VH CDR1;
5) S55K located in VH CDR2; and
6) Y104T located in VH CDR3.

In the present disclosure, a constant region of the anti-aPC monoclonal antibody includes one or more of human IgG1, IgG2, IgG3 and IgG4 sequences.

Preferably, in the present disclosure, the mutation sites of the anti-aPC monoclonal antibody where the original antibody is mutated include at least: N31F located in VH CDR1; S55K located in VH CDR2; N57R located in VL CDR2; and E59G located in VL CDR2.

Preferably, in the present disclosure, the mutation sites of the anti-aPC monoclonal antibody where the original antibody is mutated include at least: N57R located in VL CDR2; E59G located in VL CDR2; Q93V located in VL CDR3; N31F located in VH CDR1; and S55K located in VH CDR2.

Another aspect of the present disclosure provides a biological material related to the anti-aPC monoclonal antibody, which is any one or more of 1) to 10) as follows:

1) a nucleic acid molecule encoding the anti-aPC monoclonal antibody as described above;
2) an expression cassette containing the nucleic acid molecule as described in 1);
3) a construct containing the nucleic acid molecule as described in 1);
4) a construct containing the expression cassette as described in 2);
5) an expression system containing the nucleic acid molecule as described in 1);
6) an expression system containing the expression cassette as described in 2);
7) an expression system containing the construct as described in 3);
8) an expression system containing a recombinant vector as described in 4);
9) a pair of primers for amplifying the nucleic acid molecule encoding the amino acid sequence of the anti-aPC monoclonal antibody as described above; and
10) a fusion antibody containing the anti-aPC monoclonal antibody as described above.

Another aspect of the present disclosure provides a preparation product. The preparation product is a pharmaceutical composition or a detection kit. The preparation product includes the anti-aPC monoclonal antibody as described above or any one or more of the related biological materials thereof. When being the pharmaceutical composition, the preparation product further includes a pharmaceutically acceptable carrier.

Another aspect of the present disclosure provides a method for treating coagulation-related disorders, which includes: administering to an individual in need of treatment an effective amount of the anti-aPC monoclonal antibody or the related biological material thereof as described above. The individual suffers from coagulation deficiency or defect disorders, or the individual is in need of blood coagulation treatment, or the individual suffers from sepsis or hemophilia, or the individual is in need of regulation of hemostasis.

Another aspect of the present disclosure provides use of the anti-aPC monoclonal antibody or the related biological material thereof in preparation of a drug for prevention and/or treatment of coagulation deficiency or defect disorders. The coagulation deficiency or defect disorders include disorders causing coagulopathy due to deficiency of coagulation factors and thus causing bleeding, and coagulation disturbances caused by trauma or surgery. Further, the coagulation deficiency or defect disorders include hemophilia, sepsis, traumatic hemorrhage and the like.

Another aspect of the present disclosure provides use of the anti-aPC monoclonal antibody or the related biological material thereof in preparation of a promoter for promoting an ability of aPC to cleave histones H3 and H4, or in preparation of a drug for inhibiting anticoagulant activity of activated protein C in an individual, or in preparation of a drug for prevention and/or treatment in an individual in need of blood coagulation, or in preparation of a drug for prevention and/or treatment in an individual suffering from sepsis, or in preparation of a drug for prevention and/or treatment in an individual suffering from hemophilia, or in preparation of a drug for regulating hemostasis in an individual, or in immunoassays for non-disease diagnosis and treatment purposes or in preparation of a detection reagent or kit for aPC, or in combination with other reagents or drugs.

Another aspect of the present disclosure provides a preparation method of the anti-aPC monoclonal antibody as described above. The method includes: cultivating an expression system of the anti-aPC monoclonal antibody under conditions suitable for expressing the anti-aPC monoclonal antibody, so as to express the anti-aPC monoclonal antibody.

The present disclosure has the following beneficial effects: the anti-aPC monoclonal antibody provided in the present disclosure is a humanized antibody obtained by humanizing HAPC 1573, or by performing screening of mutations on a single site and a combination of sites at the same time. The anti-aPC monoclonal antibody selectively binds to and inhibits activated protein C, but does not bind to or inhibit unactivated protein C. The anti-aPC monoclonal antibody selectively binds to human activated protein C, but does not bind to activated protein C of other species or unactivated protein C. The affinity of the antibody is significantly increased, and the affinity of some of the antibodies is 100 times higher than that of HAPC 1573. In a Protac-dependent APTT coagulation assay, a very small amount of the antibody, such as 1 μg/ml, is used in the present disclosure and can achieve the maximum inhibitory effect on the anticoagulant activity of aPC. The antibody can potentially block the anticoagulant activity of aPC, and has broad application prospects in the treatment of coagulation deficiency or defect disorders.

DETAILED DESCRIPTION OF THE PREFERRED EMBODIMENTS

Figure 1A:
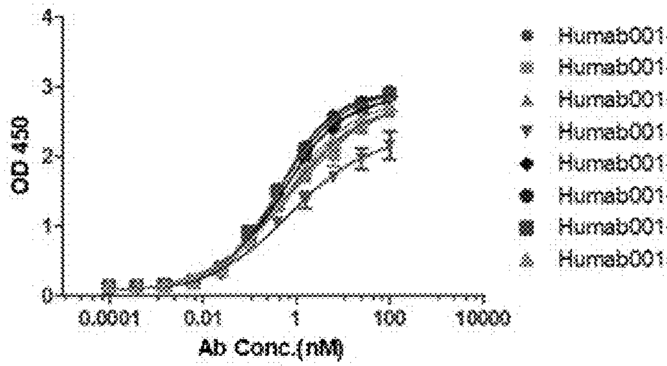
FIG. 1 shows binding abilities of humanized anti-aPC monoclonal antibodies (Humab001-1 to Humab001-28 or HAPC-1 to HAPC-28) to human aPC.
Figure 1B:
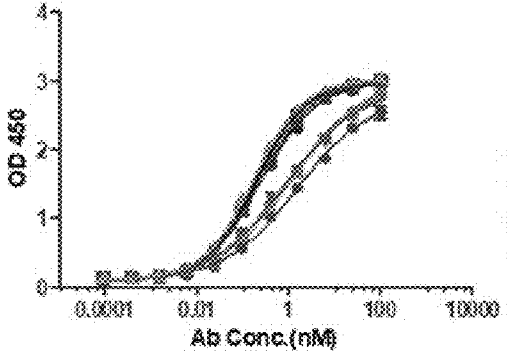
Figure 1C:
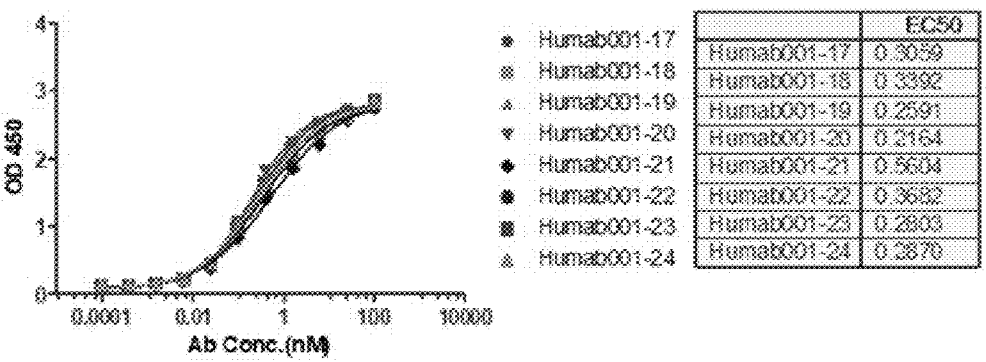
Figure 1D:
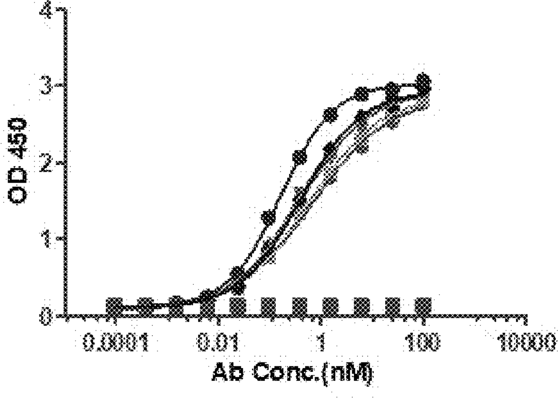

In the present disclosure, HAPC 1573 is humanized and then optimized for affinity, and optimized mutation sites are screened in a Fab-based manner to finally obtain 6 optimal sites. Further, through the combination of mutations, the affinity of the obtained optimized mutants is 100 times higher than that of HAPC 1573, and in a Protac-dependent APTT coagulation assay, the mutant antibody at an amount of 1 μg/ml can achieve the maximum inhibitory effect on the anticoagulant activity of aPC, and thus has the possibility of further clinical application.

The present disclosure provides an anti-aPC antibody, namely an anti-aPC monoclonal antibody 14 (HAPC-14). The antibody includes:

(a) a heavy chain including a heavy chain CDR represented by any one or more of SEQ ID NOs: 27, 28 and 29; and/or (b) a light chain including a light chain CDR represented by any one or more of SEQ ID NOs: 30, 31 and 32.

The anti-aPC monoclonal antibody 14 (HAPC-14) provided in the present disclosure has a heavy chain sequence as shown in SEQ ID NO: 5 and a light chain sequence as shown in SEQ ID NO: 6.

The present disclosure further provides a mutant antibody of a monoclonal antibody (anti-aPC monoclonal antibody 14) against human activated protein C (aPC). After design, screening and statistics of the mutant antibody on the basis of the sequence of the anti-aPC monoclonal antibody 14, it is found that mutations at one or more of the following six sites significantly affect the binding ability of a monoclonal antibody Fab fragment to a capture antibody, and the mutant antibody has high affinity, high functional activity and small differences from germline sequence. The six sites are:

a) N57R/W located in VL CDR2 (N57R is preferred to N57W);
b) E59G/P located in VL CDR2 (E59G is preferred to E59P);
c) Q93V located in VL CDR3;
d) N31F located in VH CDR1;
e) S55K located in VH CDR2; and
f) Y104T located in VH CDR3.

The most crucial mutant sites are N57R in the light chain and N31F in the heavy chain. In some embodiments, a concentration of the anti-aPC monoclonal antibody required to completely inhibit the anticoagulant activity of aPC and restore normal coagulation function in a humanized protein C (haPC) hemophilia mouse model is as low as 1 μg/ml.

For the convenience of description, the combinations of mutations will be described in short forms. N57R refers to N57R located in VL CDR2, N57W refers to N57W located in VL CDR2, E59G refers to E59G located in VL CDR2, E59P refers to E59P located in VL CDR2, Q93V refers to Q93V located in VL CDR3, N31F refers to N31F located in VH CDR1, S55K refers to S55K located in VH CDR2, and Y104T refers to Y104T located in VH CDR3.

In the present disclosure, the combination of mutations at the six sites includes, but not limited to, (1) only one mutation at any one of the following sites: N57R, N57W, E59G, E59P, Q93V, N31F or S55K; or (2) mutations at both of the following two sites: N57R and N57W; E59G and E59P; Q93V and N31F; N31F and S55K; N57R and E59G; N57R and E59P; N57R and Q93V; N57R and N31F; N57R and S55K; N57W and E59P; N57W and Q93V; N57W and N31F; N57W and S55K; E59G and Q93V; E59G and N31F; E59G and S55K; E59P and N31F; E59P and S55K; or Q93V and S55K; or (3) mutations at all of the following three sites: N57R, N57W and E59G; N57R, N57W and E59P; N57R, N57W and Q93V; N57R, N57W and N31F; N57R, N57W and S55K; N57R, E59G and E59P; N57R, E59G and Q93V; N57R, E59G and N31F; N57R, E59G and S55K; N57R, E59P and Q93V; N57R, E59P and N31F; N57R, E59P and S55K; N57R, Q93V and N31F; N57R, Q93V and S55K; N57R, N31F and S55K; N57W, E59G and E59P; N57W, E59G and Q93V; N57W, E59G and N31F; N57W, E59G and S55K; N57W, E59P and Q93V; N57W, E59P and N31F; N57W, E59P and S55K; N57W, Q93V and N31F; N57W, Q93V and S55K; N57W, N31F and S55K; E59G, E59P and Q93V; E59G, E59P and N31F; E59G, E59P and S55K; E59G, Q93V and N31F; E59G, Q93V and S55K; E59G, N31F and S55K; E59P, Q93V and N31F; E59P, Q93V and S55K; E59P, N31F and S55K; or Q93V, N31F and S55K; or (4) mutations at all of the following four sites: N57R, N57W, E59G and E59P; N57R, N57W, E59G and Q93V; N57R, N57W, E59G and N31F; N57R, N57W, E59G and S55K; N57R, E59G, E59P and Q93V; N57R, E59G, E59P and N31F; N57R, E59G, E59P and S55K; N57R, E59G, Q93V and N31F; N57R, E59G, Q93V and S55K; N57R, E59P, Q93V and N31F; N57R, E59P, Q93V and S55K; N57R, E59P, N31F and S55K; N57R, Q93V, N31F and S55K; N57W, E59G, E59P and Q93V; N57W, E59G, E59P and N31F; N57W, E59G, E59P and S55K; N57W, E59P, Q93V and N31F; N57W, E59P, Q93V and S55K; N57W, E59P, N31F and S55K; N57W, Q93V, N31F and S55K; E59G, E59P, Q93V and N31F; E59G, E59P, Q93V and S55K; E59G, Q93V, N31F and S55K; or E59P, Q93V, N31F and S55K; or (5) mutations at all of the following five sites: N57R, N57W, E59G, E59P and Q93V; N57R, N57W, E59G, E59P and N31F; N57R, N57W, E59G, Q93V and N31F; N57R, N57W, E59P, Q93V and N31F; N57R, E59G, E59P, Q93V and N31F; N57W, E59G, E59P, Q93V and N31F; N57R, N57W, E59G, E59P and S55K; N57R, N57W, E59G, Q93V and S55K; N57R, N57W, E59P, Q93V and S55K; N57R, E59G, E59P, Q93V and S55K; N57W, E59G, E59P, Q93V and S55K; N57R, N57W, E59G, N31F and S55K; N57R, N57W, E59P, N31F and S55K; N57R, E59G, E59P, N31F and S55K; N57W, E59G, E59P, N31F and S55K; N57R, N57W, Q93V, N31F and S55K; N57R, E59G, Q93V, N31F and S55K; N57W, E59G, Q93V, N31F and S55K; N57R, E59P, Q93V, N31F and S55K; N57W, E59P, Q93V, N31F and S55K; or E59G, E59P, Q93V, N31F and S55K; or (6) mutations at all of the following six sites: N57R, N57W, E59G, E59P, Q93V and N31F; N57R, N57W, E59G, E59P, Q93V and S55K; N57R, N57W, E59G, E59P, N31F and S55K; N57R, N57W, E59G, Q93V, N31F and S55K; N57R, N57W, E59P, Q93V, N31F and S55K; N57R, E59G, E59P, Q93V, N31F and S55K; or N57W, E59G, E59P, Q93V, N31F and S55K; or (7) mutations at all of the following seven sites: N57R, N57W, E59G, E59P, Q93V, N31F and S55K.

In a specific embodiment, the present disclosure provides an anti-aPC monoclonal antibody, which includes:

- one or two or three of a heavy chain CDR1 represented by SEQ ID NO: 27 or 33, a heavy chain CDR2 represented by SEQ ID NO: 28 or 40, and a heavy chain CDR3 represented by SEQ ID NO: 29 or 77; and/or
- one or two or three of a light chain CDR1 represented by SEQ ID NO: 30, a light chain CDR2 represented by any one of SEQ ID NOs: 31, 37, 43, 49 and 73, and a light chain CDR3 represented by SEQ ID NO: 32 or 44.

In a specific embodiment, the antibody is selected from the following:

- an antibody including (a) heavy chain CDRs represented by SEQ ID NOs: 27, 28 and 29; and/or
- (b) light chain CDRs represented by SEQ ID NOs: 30, 31 and 32;
- an antibody including (c) heavy chain CDRs represented by SEQ ID NOs: 33, 34 and 35; and/or
- (d) light chain CDRs represented by SEQ ID NOs: 36, 37 and 38;
- an antibody including (e) heavy chain CDRs represented by SEQ ID NOs: 39, 40 and 41; and/or
- (f) light chain CDRs represented by SEQ ID NOs: 42, 43 and 44;
- an antibody including (g) heavy chain CDRs represented by SEQ ID NOs: 45, 46 and 47; and/or
- (h) light chain CDRs represented by SEQ ID NOs: 48, 49 and 50;
- an antibody including (i) heavy chain CDRs represented by SEQ ID NOs: 51, 52 and 53; and/or
- (j) light chain CDRs represented by SEQ ID NOs: 54, 55 and 56;
- an antibody including (k) heavy chain CDRs represented by SEQ ID NOs: 57, 58 and 59; and/or
- (1) light chain CDRs represented by SEQ ID NOs: 60, 61 and 62;
- an antibody including (m) heavy chain CDRs represented by SEQ ID NOs: 63, 64 and 65; and/or
- (n) light chain CDRs represented by SEQ ID NOs: 66, 67 and 68;
- an antibody including (o) heavy chain CDRs represented by SEQ ID NOs: 69, 70 and 71; and/or
- (p) light chain CDRs represented by SEQ ID NOs: 72, 73 and 74;
- an antibody including (q) heavy chain CDRs represented by SEQ ID NOs: 75, 76 and 77; and/or
- (r) light chain CDRs represented by SEQ ID NOs: 78, 79 and 80;
- an antibody including(s) heavy chain CDRs represented by SEQ ID NOs: 81, 82 and 83; and/or
- (t) light chain CDRs represented by SEQ ID NOs: 84, 85 and 86; and
- an antibody including (u) heavy chain CDRs represented by SEQ ID NOs: 87, 88 and 89; and/or
- (v) light chain CDRs represented by SEQ ID NOs: 90, 91 and 92.

In the present disclosure, a heavy chain framework region of the anti-aPC monoclonal antibody may be any existing framework region suitable for exerting functions of the anti-aPC monoclonal antibody of the present disclosure, and may be human-originated or mouse-originated.

In the present disclosure, a light chain framework region of the anti-aPC monoclonal antibody may be any existing framework region suitable for exerting functions of the anti-aPC monoclonal antibody of the present disclosure, and may be human-originated or mouse-originated.

In a specific embodiment, the anti-aPC monoclonal antibody includes:

- a heavy chain sequence as shown in any of SEQ ID NOs: 5, 7, 9, 11, 13, 15, 17, 19, 21, 23 and 25; and/or
- a light chain sequence as shown in any of SEQ ID NOs: 6, 8, 10, 12, 14, 16, 18, 20, 22, 24 and 26.

In a specific embodiment, the anti-aPC monoclonal antibody is selected from the following: an antibody HaPC14 including a heavy chain sequence as shown in SEQ ID NO: 5 and a light chain sequence as shown in SEQ ID NO: 6;

- an antibody HaPC14-1 including a heavy chain sequence as shown in SEQ ID NO: 7 and a light chain sequence as shown in SEQ ID NO: 8;
- an antibody HaPC14-2 including a heavy chain sequence as shown in SEQ ID NO: 9 and a light chain sequence as shown in SEQ ID NO: 10;
- an antibody HaPC14-3 including a heavy chain sequence as shown in SEQ ID NO: 11 and a light chain sequence as shown in SEQ ID NO: 12;
- an antibody HaPC14-4 including a heavy chain sequence as shown in SEQ ID NO: 13 and a light chain sequence as shown in SEQ ID NO: 14;
- an antibody HaPC14-5 including a heavy chain sequence as shown in SEQ ID NO: 15 and a light chain sequence as shown in SEQ ID NO: 16;
- an antibody HaPC14-6 including a heavy chain sequence as shown in SEQ ID NO: 17 and a light chain sequence as shown in SEQ ID NO: 18;
- an antibody HaPC14-7 including a heavy chain sequence as shown in SEQ ID NO: 19 and a light chain sequence as shown in SEQ ID NO: 20;
- an antibody HaPC14-8 including a heavy chain sequence as shown in SEQ ID NO: 21 and a light chain sequence as shown in SEQ ID NO: 22;
- an antibody HaPC14-9 including a heavy chain sequence as shown in SEQ ID NO: 23 and a light chain sequence as shown in SEQ ID NO: 24; and
- an antibody HaPC14-10 including a heavy chain sequence as shown in SEQ ID NO: 25 and a light chain sequence as shown in SEQ ID NO: 26.

In the present disclosure, some sequences have the same composition, but different numbers (for details, referring to specific amino acid sequences in the sequence listing).

For example, among the sequences representing the heavy chain CDR1 of the antibody; sequences 27 and 87 are the same, and sequences 33, 39, 45, 51, 57, 63, 69, 75 and 81 are the same.

Among the sequences representing the heavy chain CDR2 of the antibody, sequences 28, 34, 52 and 70 are the same, and sequences 40, 46, 58, 64, 76, 82 and 88 are the same.

Among the sequences representing the heavy chain CDR3 of the antibody, sequences 29, 35, 41, 47, 53, 59, 65 and 71 are the same, and sequences 77, 83 and 89 are the same.

Among the sequences representing the light chain CDR1 of the antibody, sequences 30, 36, 42, 48, 54, 60, 66, 72, 78, 84 and 90 are the same.

Among the sequences representing the light chain CDR2 of the antibody, sequences 37 and 61 are the same, and sequences 49, 55, 67, 79, 85 and 91 are the same.

Among the sequences representing the light chain CDR3 of the antibody, sequences 32, 38, 68, 74 and 86 are the same, and sequences 44, 50, 56, 62, 80 and 92 are the same.

In a specific embodiment, the present disclosure further provides a biological material related to the anti-aPC monoclonal antibody, which is any one or more of 1) to 10) as follows:

1) a nucleic acid molecule encoding the anti-aPC monoclonal antibody as described above;
2) an expression cassette containing the nucleic acid molecule as described in 1);
3) a construct containing the nucleic acid molecule as described in 1);
4) a construct containing the expression cassette as described in 2);
5) an expression system containing the nucleic acid molecule as described in 1);
6) an expression system containing the expression cassette as described in 2);
7) an expression system containing the construct as described in 3);
8) an expression system containing a recombinant vector as described in 4);
9) a pair of primers for amplifying the nucleic acid molecule encoding the amino acid sequence of the anti-aPC monoclonal antibody as described above; and
10) a fusion antibody containing the anti-aPC monoclonal antibody as described above. The expression system may be a cell or a cell line, and the cell or the cell line encodes the anti-aPC monoclonal antibody.

In a specific embodiment, the present disclosure provides a preparation product. The preparation product is a pharmaceutical composition or a detection reagent or a detection kit.

In a specific embodiment, the pharmaceutical composition provided in the present disclosure includes the anti-aPC monoclonal antibody as described above, or any one or more of the biological materials as described above, and a pharmaceutically acceptable carrier. The carrier may include various excipients and diluents, which are not essential active ingredients as such and have no undue toxicity after administration. Suitable carriers are well known to those skilled in the art. For example, relevant contents of pharmaceutically acceptable carriers are described in Remington's Pharmaceutical Sciences (Mack Pub. Co., N.J., 1991).

In a specific embodiment, the detection reagent or detection kit provided in the present disclosure includes the anti-aPC monoclonal antibody as described above, or any one or more of the biological materials as described above. The antibody is labeled.

Labeling may be carried out in any existing manner, such as chemiluminescence labeling, fluorophore, radioactive labeling, chromophore or the like.

The detection reagent or kit may further include buffers, diluents, operating instructions and the like.

The antibody may be present in any form suitable for its functioning or activity, for example, in the form of an aqueous suspension.

In some embodiments, the anti-aPC monoclonal antibody of the present disclosure promotes an ability of aPC to cleave histones H3 and H4, which indicates that the anti-aPC monoclonal antibody can provide a cytoprotective effect against cytotoxicity of the histones H3 and H4.

In a specific embodiment, the present disclosure provides a method for treating coagulation deficiency or defect disorders as defined above, and specifically provides a method for treating hereditary and acquired coagulation deficiency or defect such as hemophilia A and hemophilia B or sepsis. The present disclosure also provides a method for shortening bleeding time by administering an anti-aPC monoclonal antibody to a patient in need (for example, a trauma patient or a patient in need of blood coagulation). The present disclosure further provides a method for inhibiting anticoagulant activity of activated protein C in a subject. The present disclosure further provides a method for regulating thrombosis in a subject. According to the method of the present disclosure, an effective amount of the anti-aPC monoclonal antibody described above in the present disclosure is administered to an individual in need of treatment. The present disclosure also provides a method for producing a monoclonal antibody against human aPC.

In a specific embodiment, the present disclosure provides a method for treating coagulation deficiency or defect disorders, which includes administering an effective amount of the anti-aPC monoclonal antibody or the related biological material thereof as described above to an individual in need of treatment.

In a specific embodiment, the present disclosure provides a method for treating coagulation related disorders, which includes administering an effective amount of the anti-aPC monoclonal antibody as described above or any one or more of the biological materials as described above to an individual in need of treatment. The individual suffers from coagulation deficiency or defect disorders, or the individual is in need of blood coagulation treatment, or the individual suffers from sepsis or hemophilia, or the individual is in need of regulation of hemostasis.

The coagulation deficiency or defect disorders may be hereditary or acquired, including disorders causing coagulopathy due to deficiency of one or more of coagulation factors in plasma and thus causing bleeding, and specifically including: hemophilia A, hemophilia B and hemophilia C, which are caused by the deficiency of coagulation factors VIII, IX and XI, respectively; and rare coagulation factor deficiencies, which are hemorrhagic diseases caused by absence or abnormal working of one or more of other coagulation factors (i.e., coagulation factors I, II, V, V+VIII, VII, X or XIII), for example, coagulation disturbances caused by trauma, and excessive bleeding caused by treatment of sepsis, transplantation, cardiac surgery and cosmetic surgery.

In a specific embodiment, according to the method for promoting the ability of aPC to cleave histones H3 and H4 in the present disclosure, after the administration of the anti-aPC monoclonal antibody or the related biological material or pharmaceutical composition thereof, the ability of aPC to cleave histones H3 and H4 can be promoted, so that the cytoprotective effect against cytotoxicity of histones H3 and H4 can be provided.

In a specific embodiment, according to the method for inhibiting the anticoagulant activity of activated protein C in an individual in the present disclosure, the administration of the anti-aPC monoclonal antibody or the related biological material or pharmaceutical composition thereof can inhibit the anticoagulant activity of the activated protein C in the individual, so that the coagulation function of the individual can be regulated.

In a specific embodiment, the present disclosure provides use of the anti-aPC monoclonal antibody or the related biological material thereof i) in preparation of a drug for prevention and/or treatment of coagulation deficiency or defect disorders;
ii) in preparation of a promoter for promoting the ability of aPC to cleave histones H3 and H4
iii) in preparation of a drug for inhibiting the anticoagulant activity of activated protein C in an individual;
iv) in preparation of a drug for treatment in an individual in need of blood coagulation;

vi) in preparation of a drug for regulating hemostasis in an individual;

vii) in immunoassays for disease or non-disease diagnosis and treatment purposes or in preparation of a detection reagent or kit for aPC; and viii) in combination with other reagents or drugs.

In a specific embodiment, the present disclosure further provides a preparation method of the anti-aPC monoclonal antibody as described above. The method includes: cultivating an expression system of the anti-aPC monoclonal antibody under conditions suitable for expressing the anti-aPC monoclonal antibody, so as to express the anti-aPC monoclonal antibody.

In the present disclosure, a polypeptide having a certain identity with the amino acid sequence of the anti-aPC monoclonal antibody is also within the protection scope of the present disclosure, for example, an antibody or antibody fragment (having 90%, 91%, 92%, 93%, 94%, 95%, 96%, 97%, 98%, 99% or more sequence identity) having 70%, 75%, 80%, 85%, 90%, 95%, 99% or more sequence identity with the anti-aPC monoclonal antibody and having the functions of the anti-aPC monoclonal antibody, and specifically, a polypeptide fragment obtained by substituting, deleting or adding one or more (specifically 1-50, 1-30, 1-20, 1-10, 1-5, 1-3, 1, 2 or 3) amino acids in the anti-aPC monoclonal antibody, or by adding one or more (specifically 1-50, 1-30, 1-20, 1-10, 1-5, 1-3, 1, 2 or 3) amino acids to the N-terminal and/or C-terminal of the anti-aPC monoclonal antibody, and having the functions of the anti-aPC monoclonal antibody.

The term "protein C" or "PC" refers to any variant, isoform and/or species homolog of Protein C in its zymogen form, which is naturally expressed by cells and is present in plasma, and is different from the activated form of protein C.

The term "activated protein C" or "aPC" refers to the activated form of protein C.

The term "anti-aPC monoclonal antibody" refers to an antibody that specifically binds to an epitope of aPC, and is a monoclonal antibody against human aPC. The anti-aPC monoclonal antibody may be in a variety of antibody forms, including but not limited to a complete antibody, an antibody fragment, a human antibody, a humanized antibody and a genetically engineered antibody, such as a monoclonal antibody, a chimeric antibody or a recombinant antibody as well as fragments of these antibodies, provided that they retain their properties according to the present disclosure.

The antibody fragment is further defined as Fab', Fab, $F(ab')_2$, a single-domain antibody, Fv or scFv. The anti-aPC monoclonal antibody used herein refers to an antibody molecule preparation with a single molecular component. The monoclonal antibody component exhibits single binding specificity and affinity to a particular epitope, and may have variable and constant regions derived from human germline immunoglobulin sequences. For example, a Fab fragment refers to a monovalent fragment composed of VL, VH, CL and CH1 domains; a $F(ab')_2$ fragment refers to a divalent fragment containing two Fab fragments linked by disulfide bridges in a hinge region; and a Fv fragment refers to a Fv fragment composed of VL and VH domains of a single arm of an antibody.

The term "identity" may be evaluated with naked eyes or with computer software. Using the computer software, the identity between two or more sequences may be expressed in percentage (%), which can be used to evaluate the identity between related sequences.

The term "individual" generally includes humans and non-human primates, such as mammals, dogs, cats, horses, goats, pigs and cattle, which can benefit from the treatment using the antibody, drug, composition, related preparation, kit or combined preparation described above.

The term "therapeutically effective amount" generally refers to an amount that can achieve the effect of treating the diseases listed above after an appropriate period of administration.

The term "monoclonal antibody" refers to an antibody molecule preparation of a single amino acid composition, which may have variable and constant regions derived from human germline immunoglobulin sequences. In an embodiment, the monoclonal antibody is prepared from a hybridoma including B cells, which is obtained from a transgenic non-human animal, such as a transgenic mouse, having a genome including human heavy chain transgenes and human light chain transgenes fused with immortalized cells.

The term "fusion antibody" refers to a product obtained by fusing an antibody fragment with other bioactive proteins using a genetic engineering technology. It is a recombinant protein with the above two domains, in which a target gene is linked with genes of a fragment of Ig at the gene level and expressed in eukaryotic or prokaryotic cells. The fusion antibodies can be divided into two categories according to the different fragments of Ig linked to the target protein: Fab (Fv) fusion proteins; and Fc fusion proteins. Two different proteins are linked together into one macromolecule. The linage may be realized by a chemical method or by fusion of genes. The method for preparing a fusion antibody involves conventional recombinant DNA and gene transfection techniques well known in the art. Because of the different fusion proteins, this antibody fusion protein has many biological functions, and the expressed recombinant protein affects neither the antigen binding ability of the single chain antibody nor the biological characteristics of the protein fused with it.

The term "humanized antibody" refers to an antibody in which a framework region or "complementary-determining region" (CDR) has been modified into a CDR of an immunoglobulin having different specificities compared to the parental immunoglobulin.

When referring to inhibiting and/or blocking the binding of an aPC substrate to aPC, the term inhibiting and blocking also includes a measurable decrease in the binding affinity of aPC to a physiological substrate when aPC is in contact with an anti-aPC antibody compared with the situation that aPC is not in contact with the anti-aPC antibody, for example, blocking the interaction of aPC with its substrates including Factor Va or Factor VIIIa by at least about 10%, about 20%, about 30%, about 40%, about 50%, about 60%, about 70%, about 80%, about 90%, about 91%, about 92%, about 93%, about 94%, about 95%, about 96%, about 97%, about 98%, about 99% or about 100%.

"Complementary-determining region" or "CDR" refers to one of three hypervariable regions in the heavy chain variable region or light chain variable region of an antibody molecule, which forms an N-terminal antigen-binding surface complementary to a three-dimensional structure of a bound antigen. Starting from the N-terminal of the heavy chain or light chain, these complementarity-determining regions are denoted as "CDR1", "CDR2" and "CDR3" respectively. The CDRs involve antigen-antibody binding, and CDR3 includes a unique region specific for antigen-antibody binding. Therefore, an antigen-binding site may include six CDRs, which include CDRs from each of the heavy chain and light chain variable regions.

The term "epitope" means a range or region of an antigen to/with which an antibody specifically binds or interacts, and in some embodiments, "epitope" indicates where the antigen physically contacts the antibody.

The term "conservative substitution" means a polypeptide modification, which involves the replacement of one or more amino acids with amino acids that have similar biochemical characteristics but do not cause loss of biological or biochemical functions of the polypeptide. "Conservative amino acid substitution" means the replacement of an amino acid residue with an amino acid residue having similar side chains. The families of amino acid residues having similar side chains have been defined in the art. Common conservative substitutions are, for example, mutual substitutions between aromatic amino acids Phe, Trp and Tyr, mutual substitutions between hydrophobic amino acids Leu, Ile and Val, mutual substitutions between polar amino acids Gln and Asn, mutual substitutions between basic amino acids Lys, Arg and His, mutual substitutions between acidic amino acids Asp and Glu, and mutual substitutions between hydroxyl amino acids Ser and Thr.

The term "identity" refers to the proportion of nucleotides being identical when two nucleic acids or two polypeptides are compared, for example, at least about 80% of the nucleotides or amino acid, usually at least about 85%, in some embodiments about 90%, 91%, 92%, 93%, 94% or 95%, in at least one embodiment at least about 96%, 97%, 98%, 99%, 99.1%, 99.2%, 99.3%, 99.4% or 99.5% of the nucleotides or amino acids are identical.

Nucleic acids may be present in whole cells, in cell lysates or in a partially purified or substantially pure form. Nucleic acids are "isolated" or "made substantially pure" when being purified from other cellular components that are normally associated with nucleic acids in a natural environment. Nucleic acids can be isolated using techniques well known in the art, such as alkaline/SDS treatment, CsCl banding, column chromatography, agarose gel electrophoresis and the like.

Relevant terms used in the present disclosure are explained as follows:

| | |
|---|---|
| CDRs | Complementary-determining regions |
| CV | Column volume |
| ELISA | Enzyme-linked immunosorbent assay |
| Fab | Antigen binding fragment |
| hr | Hour |
| HRP | Horseradis peroxydase |
| KDa | Kilodaltons |
| koff | Dissociation Rate |
| OD | Optical density |
| PBS | Phosphate buffered saline |
| PCR | Polymerase chain reaction |
| PE | Periplasmic extract |
| SA | Streptavidin |
| scFv | Single chain variable fragment |
| SPR | Surface plasmon resonance |
| TMB | Tetra-methyl-benzidine |
| VH | Heavy chain variable domain |
| VL | Light chain variable domain |

Further descriptions of the present disclosure are provided below with reference to embodiments. The following embodiments are used to describe the present disclosure, but are not intended to limit the scope of the present disclosure. Except for the content specifically mentioned below, the process, conditions, experimental methods, and the like for implementing the present disclosure are all general knowledge and well-known knowledge in the field, and the present disclosure is not particularly limited.

Example 1 Humanization of Mouse Anti-aPC Monoclonal Antibody

Variable region sequences of mouse hybridoma antibodies were humanized. VH/VL amino acid sequences were numbered using a Kabat system. Then, the VH/VL sequences were analyzed for the presence of hot spot sites, including unpaired cysteine residues, N-linked glycosylation sites and deamination sites inside CDRs. N-linked glycosylation sites close to CDRs would also be considered as high risk sites. If such sites are recognized, they need to be removed. Based on the VH/VL sequence alignment, the best human germline gene frame sequences were selected, and J region sequences were selected and spliced based on the best homology. Homology modeling was carried out on murine VH/VL sequences to form 3D structures. FR residues within a distance of 5 Å from CDRs, residues on a VH/VL binding surface that affect antigen binding after being altered and the like will be considered as potential sites in need of back mutations. The importance of back mutations was determined by analysis using a computer, and different combinations containing a single or several back mutations were designed.

Target segment DNA was amplified through PCR, and plasmids encoding humanized antibody sequences were constructed. The antibodies were subjected to transient transfection and expression and purified by a protein A affinity chromatography column. The humanized antibodies were assayed by SEC-HPLC and SDS-PAGE, and 28 humanized anti-aPC monoclonal antibody clones were obtained.

1.1 ELISA Assays of Affinities of Anti-aPC Monoclonal Antibodies to Human aPC (haPC)

Affinities of chimeric antibodies and the above 28 humanized antibodies to haPC were assayed by ELISA and FACS assays.

The assay results are shown in FIG. 1. NOs. 1-28 (Humab001-1 to Humab001-28 or HAPC-1 to HAPC28) humanized antibodies, 3657 positive control antibody (3657 PC mAb) and chimeric antibody (30120-mAb001×hIgG) had good binding to haPC. NOs. 13-20 antibodies had low EC50 values, which indicated that these antibodies had higher binding abilities to haPC.

1.2 ELISA Assays of Binding Abilities of Anti-aPC Monoclonal Antibodies to Human PC (hPC)

NOs. 13-20 humanized anti-aPC monoclonal antibodies (Humab001-13 to Humab001-20 or HAPC-13 to HAPC-20) were selected and assayed for their binding abilities to hPC.

Figure 2A:
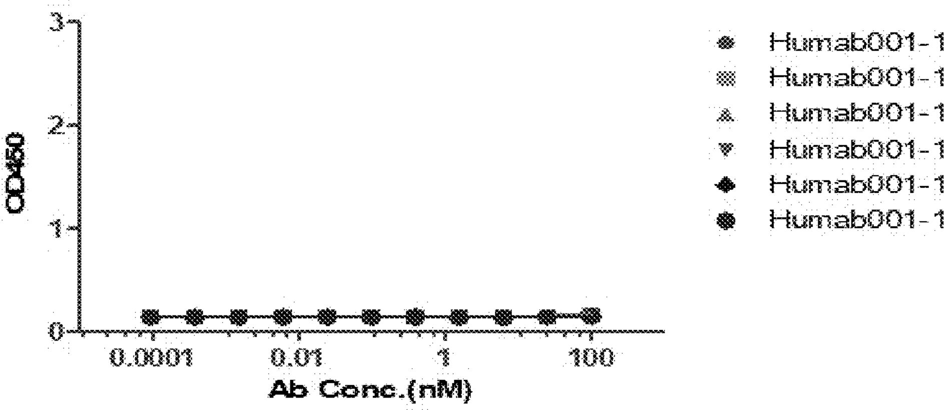
FIG. 2 shows binding abilities of humanized anti-aPC monoclonal antibodies (Humab001-1 to Humab001-28 or HAPC-1 to HAPC-28) to human PC.
Figure 2B:
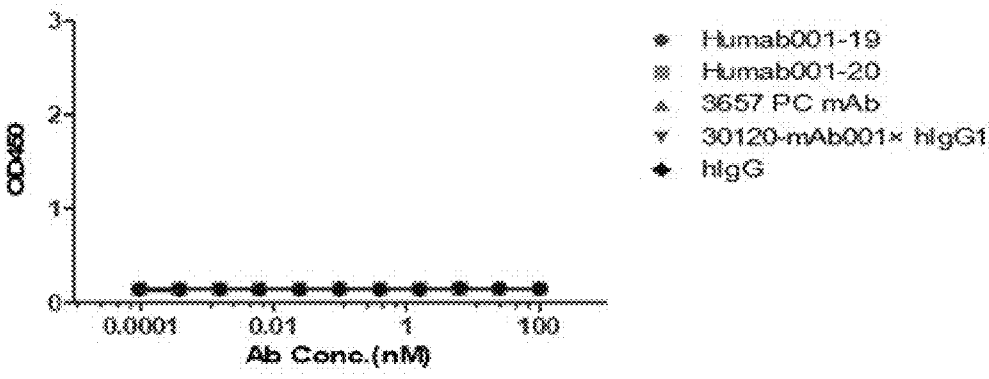
Figure 2C:
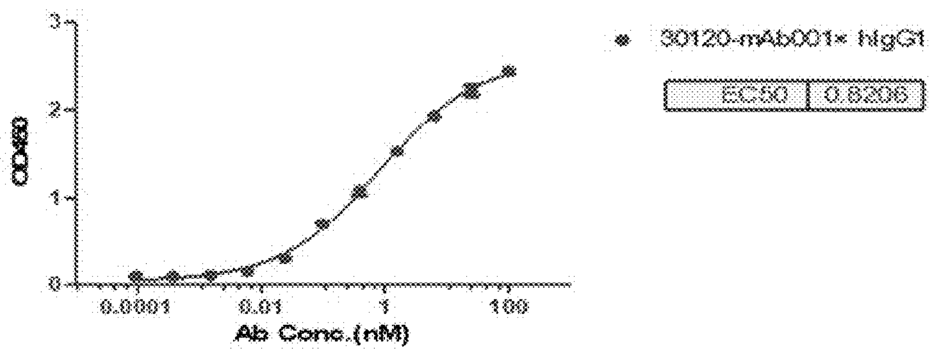
Figure 3A:
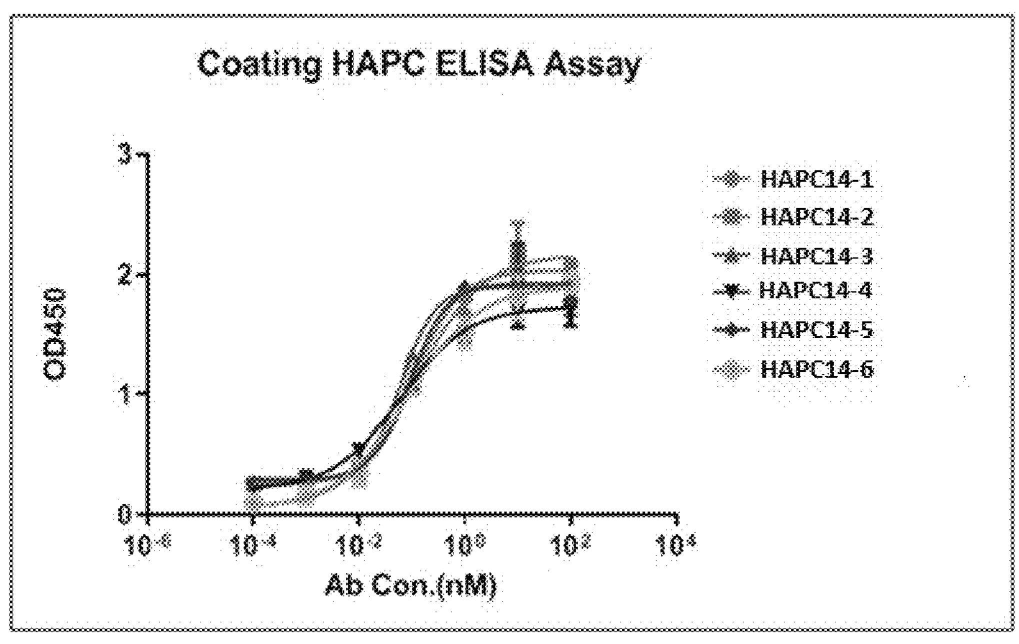
FIG. 3 shows binding abilities of HAPC-14 mutant antibodies (HAPC14-1 to HAPC14-10 or HAPC-14-1 to HAPC-14-10) to hAPC/hPC; where abscissas in FIGS. 3A-3D are respectively $10^{-6}$ nM, $10^{-4}$ nM, $10^{-2}$ nM, $10^{0}$ nM, $10^{2}$ nM and $10^{4}$ nM.
Figure 3B:
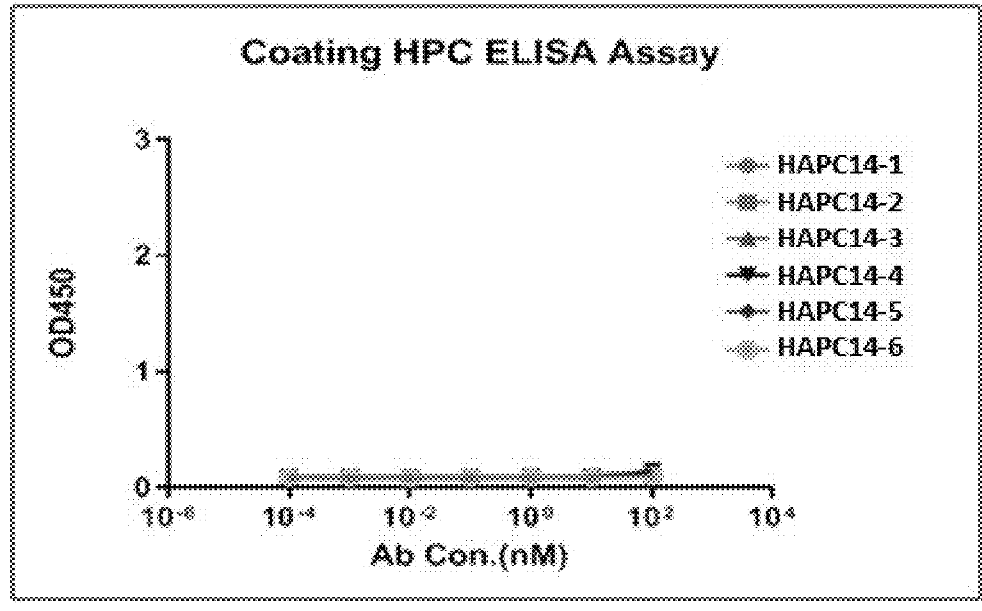
Figure 3C:
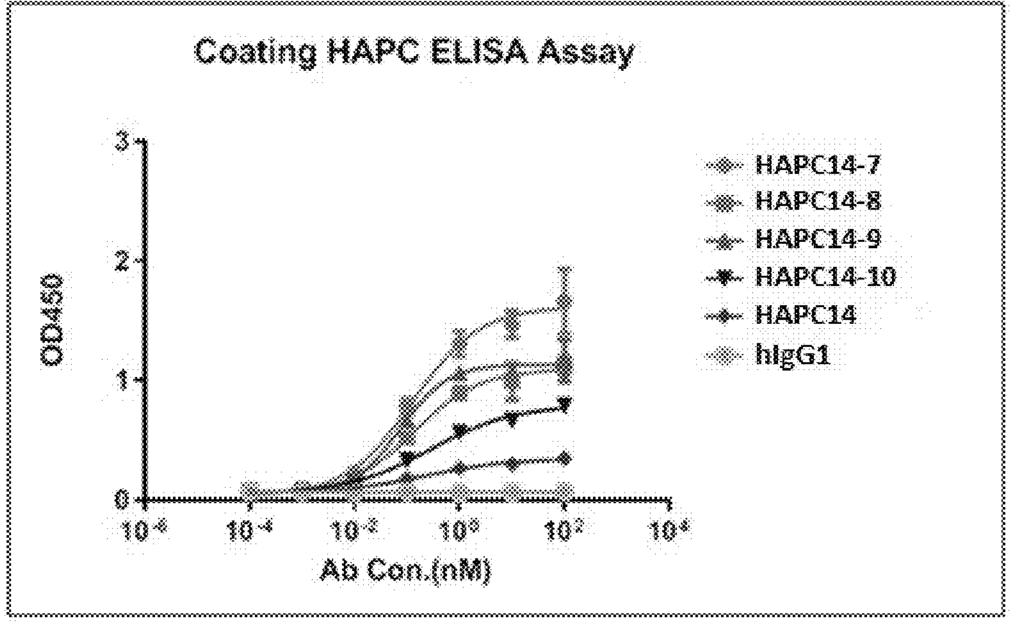
Figure 3D:
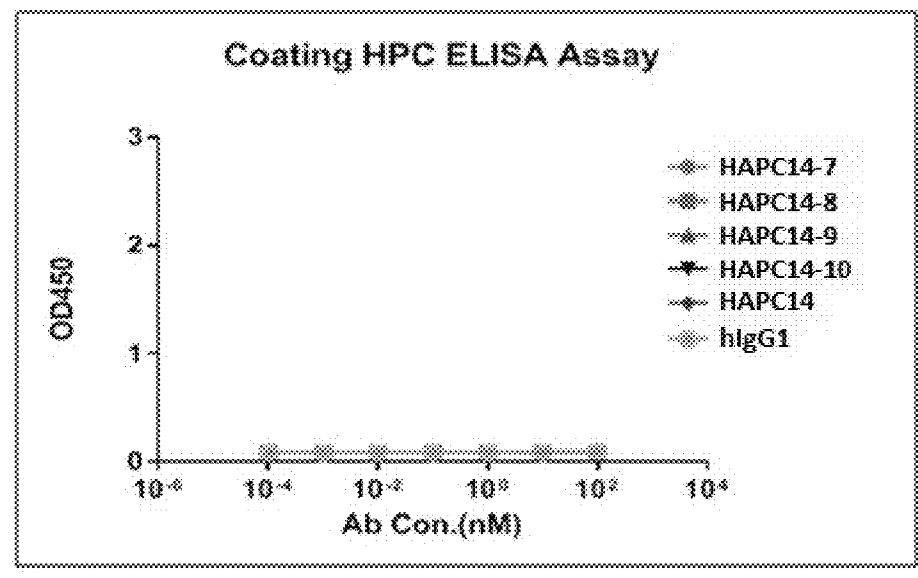
Figure 4A:
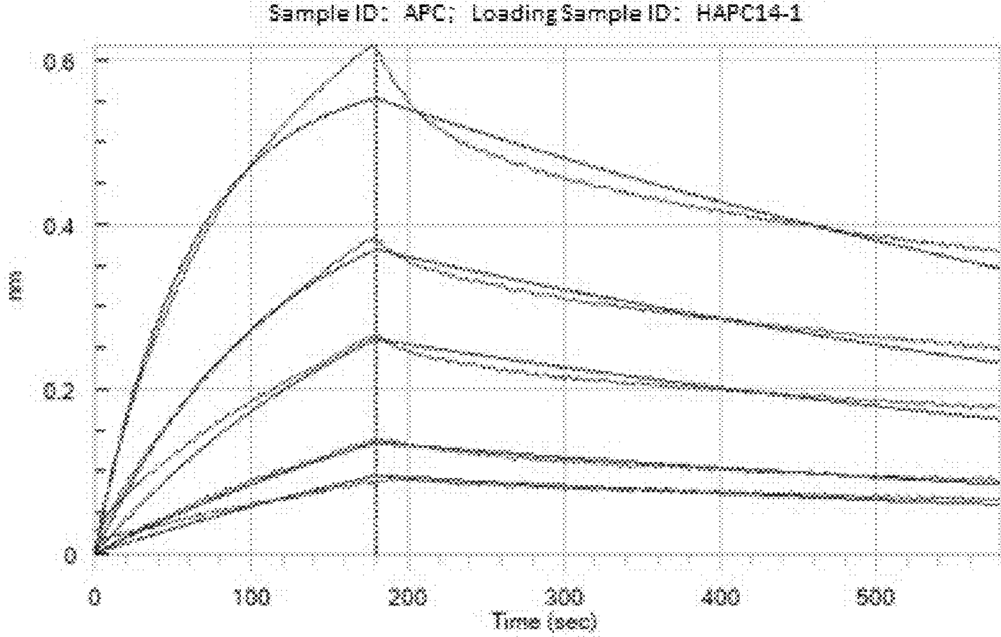
FIG. 4 shows assays of affinities of HAPC-14 mutant antibodies (HAPC14-1 to HAPC14-10 or HAPC-14-1 to HAPC-14-10).
Figure 4B:
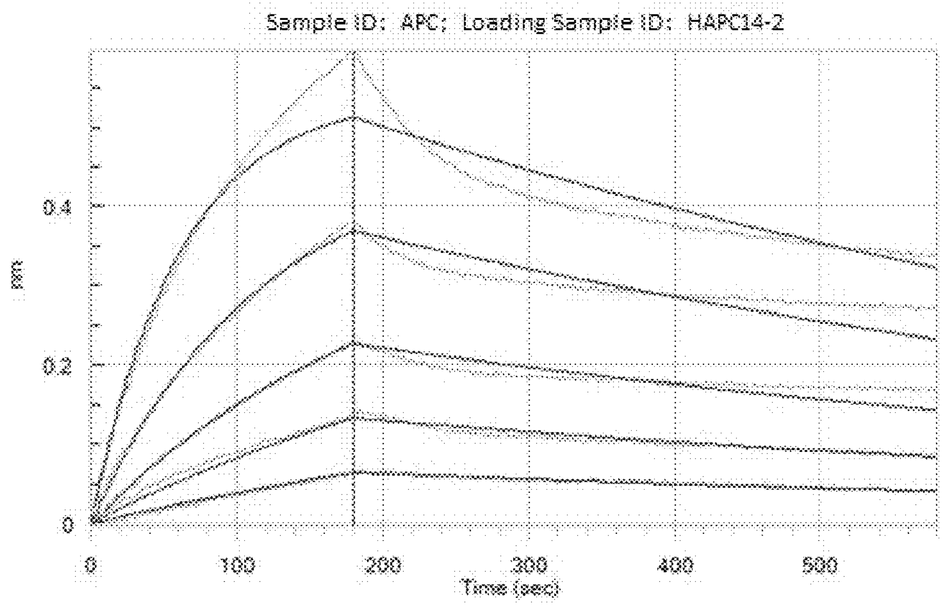
Figure 4C:
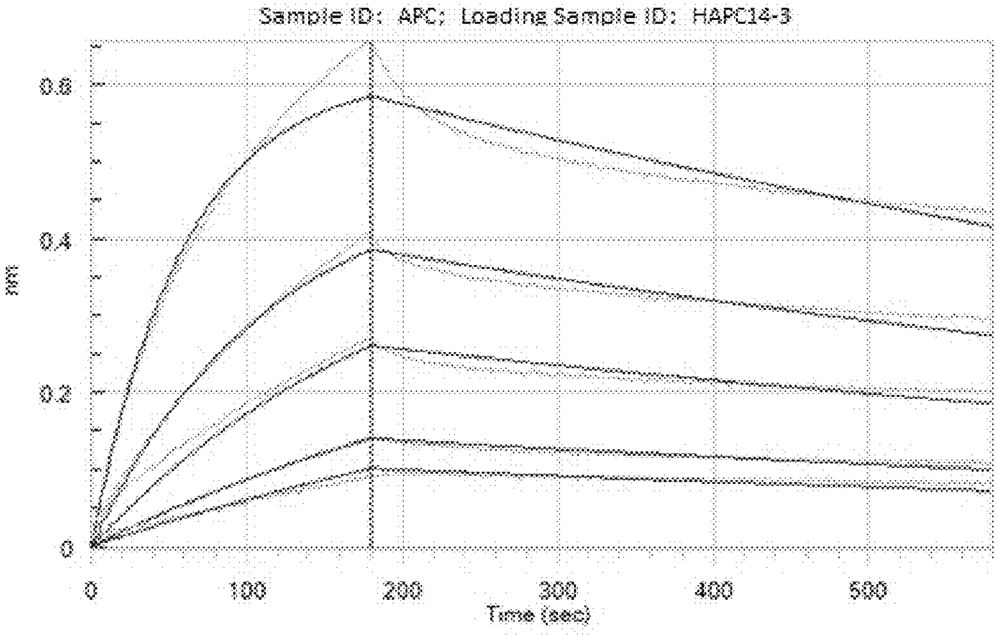
Figure 4D:
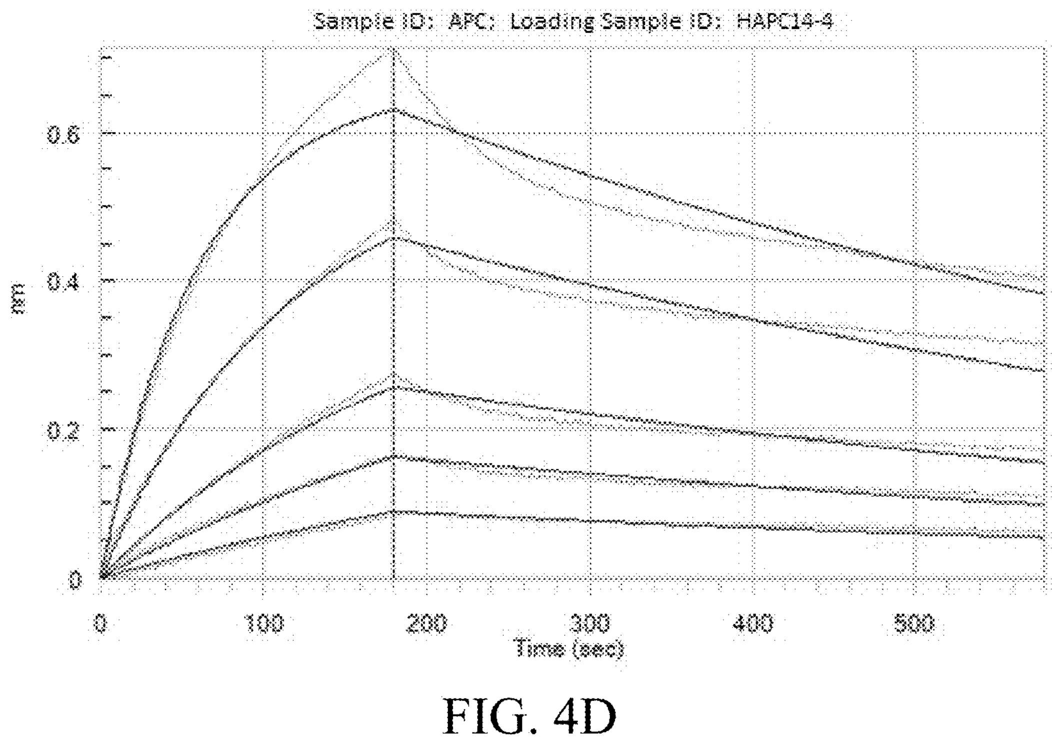
Figure 4E:
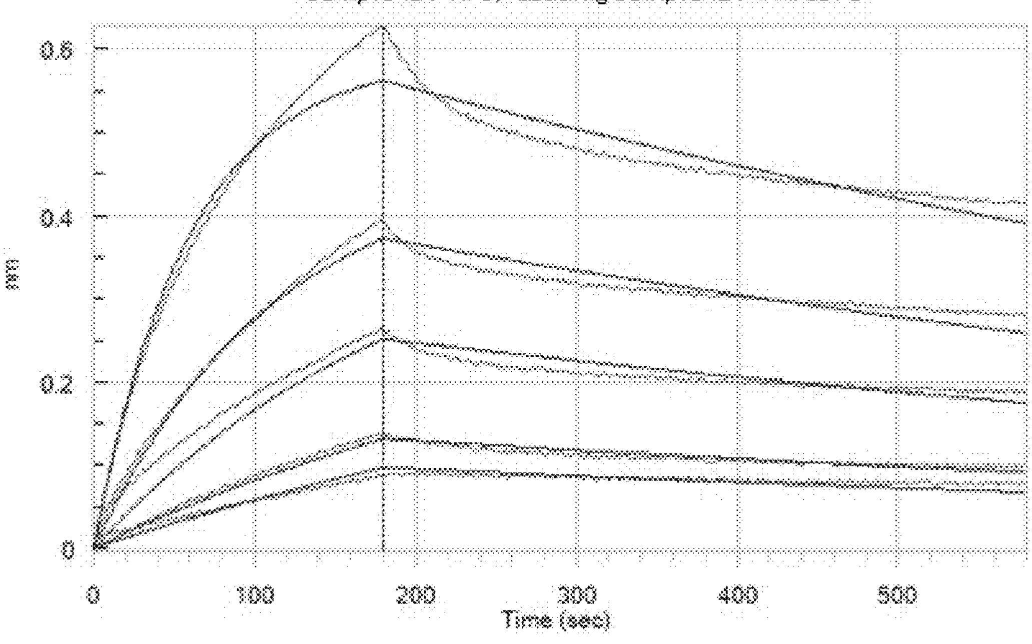
Figures 4F, 4G:
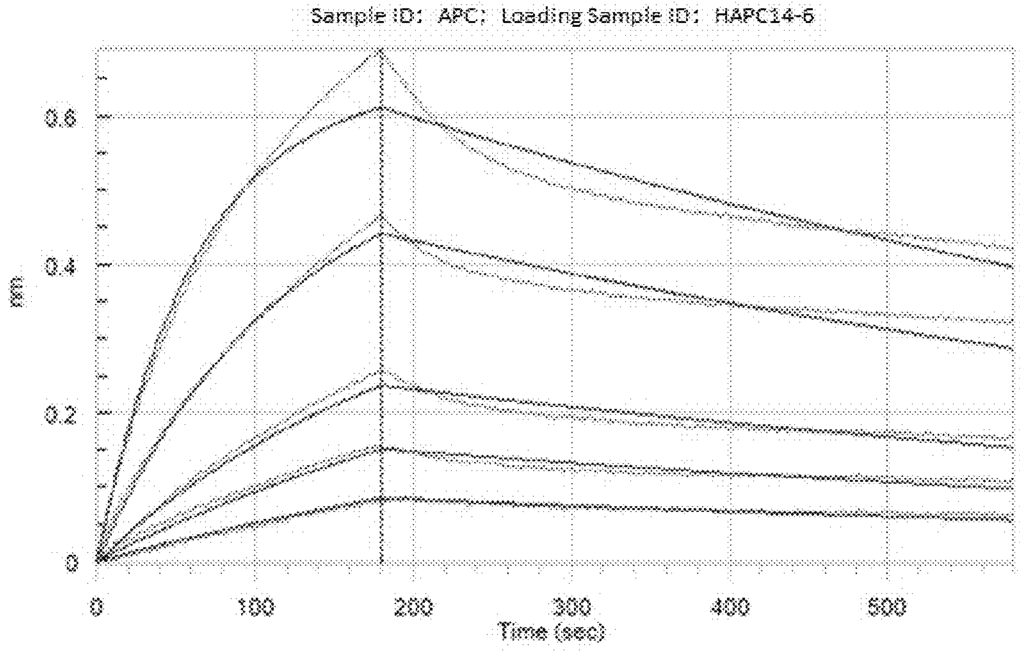
Figure 4H:
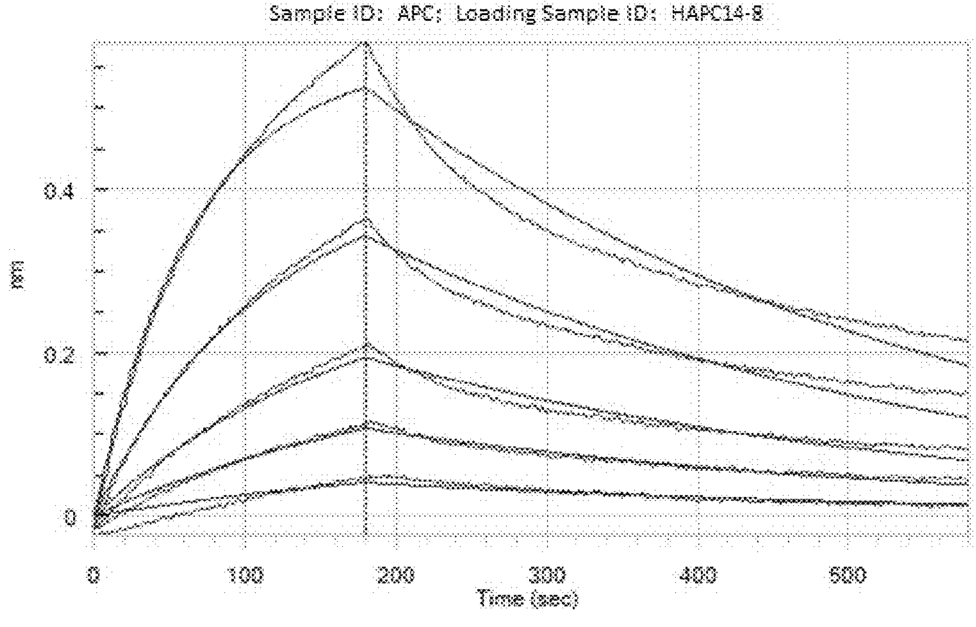
Figure 4I:
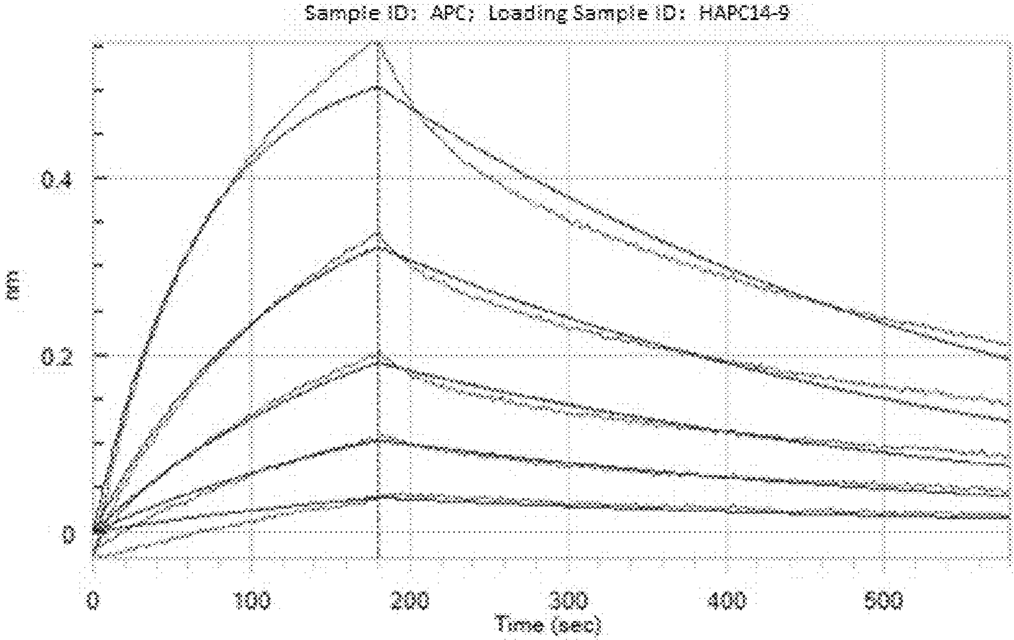
Figure 4J:
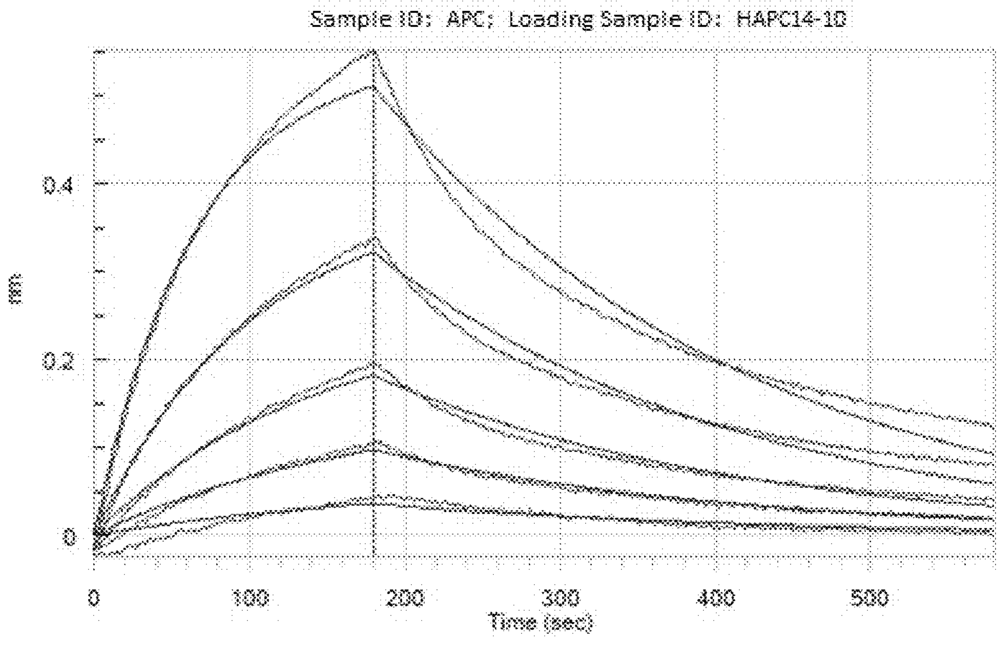
Figure 4K:
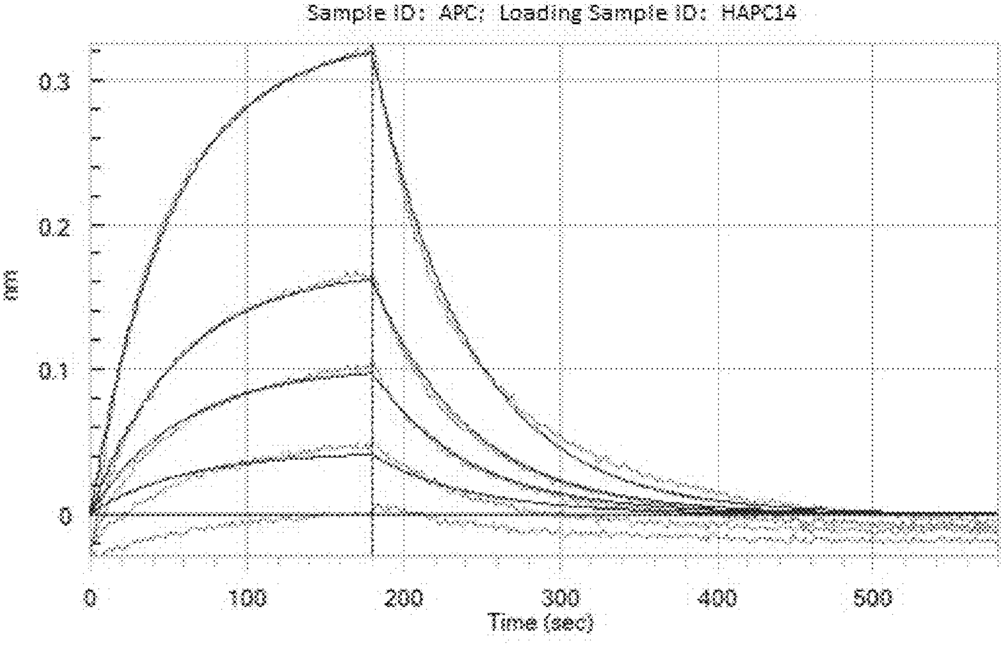

The results are shown in FIG. 2. The results showed that the NOs. 13-20 humanized anti-aPC monoclonal antibodies did not bind to hPC at all.

NO. 13 antibody (HAPC-13), NO. 14 antibody (HAPC-14) and NO. 16 antibody (HAPC-16) were three parental antibodies selected for optimization of affinity. These three antibodies had the same heavy chain framework regions and different light chain framework regions. HAPC-13 was the original, HAPC-14 had 1 back mutation based on HAPC-13, and HAPC-16 had 5 back mutations based on HAPC-13. In the following embodiments, the antibody HAPC-14 was selected for subsequent optimization of affinity.

Example 2 Optimization of Affinity of Anti-aPC Monoclonal Antibody HAPC-14

On the basis of NO. 14 antibody (Humab001-14 or HAPC14 or HAPC-14) described above, the affinity of this antibody was optimized, and mutants was constructed.

| Materials | Vendor/Generator | Catalog No. |
|---|---|---|
| Blocker Casein in PBS | Pierce | 37528 |
| SA-HRP | Sigma | S5512 |
| Goat Anti-Human IgG Fd | Southern Biotech | 2046-01 |
| Goat anti-Human IgG F(ab')2-HRP | Jackson | 109-035-006 |
| Goat anti-c-myc HRP conjugated | BETHYL | A190-104P |
| Blocker Casein in PBS | Pierce | 37528 |
| SA-HRP | Sigma | S5512 |
| Expi293F ™ Cells | Thermo Fisher | A14527 |
| ExpiFectamine293 transfection kit | Thermo Fisher | A14524 |
| Expi293F ™ expression medium | Thermo Fisher | A1435101 |
| Lipofectamine ™ 2000 Transfection Reagent | Thermo Fisher | 11668019 |
| Fetal bovine serum (FBS) | Corning | 35-076-CV |
| Opti-MEM | Thermo Fisher | 31985070 |
| MabSelect SuRe column | GE healthcare | 11-0034-93 |
| NuPAGE4%-12% Bis-Tris Gel | Thermo Fisher | NP0322BOX |
| PageRuler ™ Unstained Protein Ladder | Thermo Fisher | 26614 |
| HPLC-SEC column | TOSOH | 08541 |
| Series S Sensor Chip CM5 | GE healthcare | 29-1496-03 |
| Amine Coupling Kit | GE healthcare | BR100633 |
| 10 × HBS-EP + buffer | GE healthcare | BR100669 |
| anti-human Fc IgG | Jackson | 109-005-098 |
| 10 mM Glycine, pH 1.5 | Cool pharm | KH-59224 |

2.1 Site-Directed Mutation

Each amino acid of six complementary-determining regions (CDRs) of a parental HAPC-14 Fab clone was respectively mutated into 19 other amino acids by using site-directed mutation. DNA primers containing NNS codons encoding 20 amino acids were used to introduce mutations into each target CDR position. Phosphorylated degenerate primers were used in site-directed mutation reactions.

2.2 PCR

PCR was carried out at 94° C. for 2 minutes (94° C. for 30 seconds, 55° C. for 30 seconds, 72° C. for 5 minutes) for 16 cycles, and then at 72° C. for 10 minutes.

A PCR product was purified, and then introduced into *Escherichia coli* TG1 by electroporation for colony formation and Fab fragment production.

2.3 Preliminary Screening of Fab Mutant Library

The preliminary screening included single-point ELISA (SPE) assay carried out by capture ELISA.

Each well of 96-well plates was coated with an anti-Fab antibody in a coating buffer PBS with pH 7.4 at 4° C. The next day, the plates were blocked with casein in PBS with pH 7.4 at 25° C. for 1 hour. Then, Fab PE was added to the plates, and incubated at 25° C. for 1 hour. After the plates were washed, biotinylated antigen was added to the wells and incubated at 25° C. for 1 hour. Then, the biotinylated antigen was incubated with an SA-horseradish peroxidase (HRP) conjugate at 25° C. for 1 hour. HRP activity was detected with a tetramethylbenzidine (TMB) substrate, and the reaction was quenched with 2M HCl. The plates were read at 450 nM. Clones exhibiting an optical density (OD) signal at 450 nm that was 3 times greater than that of the parental clone were selected and sequenced. Binding-improved mutants with unique sequences of HAPC-14 were demonstrated by capture ELISA at pH 7.4. The binding-improved mutants with unique sequences of HAPC-14 were ranked by direct antigen coating ELISA. The results are shown in Table 1 below.

TABLE 1

| Antibody | Mutation | Capture Elisa OD450 | Bmax | EC50 |
|---|---|---|---|---|
| HAPC-14-Fab | WT | about 0.6196 | 0.221 | 221.3 |
| HAPC-14-R1-1H1-F2 | N to F | 2.5193 | 0.2776 | 20.33 |
| HAPC-14-R1-2H6-C2 | S to K | 1.8358 | 0.2621 | 19.42 |
| HAPC-14-R1-3H4-C5 | Y to S | 1.77415 | 0.3275 | 102.80 |
| HAPC-14-R1-3H4-C6 | Y to T | 1.4995 | 0.3245 | 55.82 |
| HAPC-14-R1-3H7-F2 | Y to P | 1.42405 | 0.1933 | 25.13 |
| HAPC-14-R1-1L7-B9 | D to A | 1.34885 | 0.1509 | 28.41 |
| HAPC-14-R1-2L4-A1 | N to L | 2.1465 | 0.2441 | 13.38 |
| HAPC-14-R1-2L4-B2 | N to W | 2.99075 | 0.6618 | 4.82 |
| HAPC-14-R1-2L4-D4 | N to R | 3.0343 | 0.5669 | 10.45 |
| HAPC-14-R1-2L4-G9 | N to K | 2.3219 | 0.2868 | 13.19 |
| HAPC-14-R1-2L6-G1 | E to G | 2.00495 | 0.4919 | 35.65 |
| HAPC-14-R1-2L6-F2 | E to K | 1.37175 | 0.2995 | 28.24 |
| HAPC-14-R1-2L6-G11 | E to P | 1.56065 | 0.2199 | 18.04 |
| HAPC-14-R1-3L1-D11 | Q to W | 2.06855 | 0.2612 | 13.64 |
| HAPC-14-R1-3L1-G8 | Q to V | 1.4895 | 0.2405 | 30.79 |

As shown in Table 1, the affinity-improved mutations in the nine individuals (HAPC-14-R1-1H1-F2, HAPC-14-R1-2H6-C2, HAPC-14-R1-3H4-C6, HAPC-14-R1-2L4-B2, HAPC-14-R1-2L4-D4, HAPC-14-R1-2L6-G1, HAPC-14-R1-2L6-G11, HAPC-14-R1-3L1-D11 and HAPC-14-R1-3L1-G8) identified in the preliminary screening of HAPC-14 were further used for designing and constructing a combinatorial mutant library.

2.4 Verification of Main Fab Mutant Library by Direct KD ELISA Ranking

KD ranking of the binding-improved Fab of each mutant was determined by KD ELISA of direct antigen coating ELISA.

Each well of 96-well plates was coated with hPro1. biotin in 1×PBS buffer with pH 7.4, and incubation was carried out overnight at 4° C. The next day, the plates were blocked with casein in 1×PBS buffer with pH 7.4 at 25° C. for 1 hour. Fab PE of each mutant diluted according to one concentration was added to the plates and incubated at 25° C. for 1 hour. Then the Fab PE was incubated with goat anti-c-myc HRP conjugated at 25° C. for 1 hour. HRP activity was detected with a tetramethylbenzidine (TMB) substrate, and the reaction was quenched with 2M HCl. OD values of each plate were read at 450 nM.

2.5 Combinatorial Screening of HAPC-14 Fab Library

Point mutations in VH and VL determined to be beneficial for antigen binding were further combined for additional binding synergy. In short, each degenerate primer was phosphorylated and then used with uracilated ssDNA at a ratio of 10:1. The mixture was heated to 85° C. for 5 minutes and then cooled to 55° C. for more than 1 hour. Then, T4 ligase and T4 DNA polymerase were added, and the mixture was incubated at 37° C. for 1.5 hours. 100 ng of combinatorial library DNA was introduced into TG1 by electroporation to form colonies and produce Fab fragments.

The combinatorial mutants were expressed as Fab, and screened using capture ELISA. Clones exhibiting an optical density (OD) signal at 450 nm that was 3 times greater than that of the first-round precursor clone were selected and sequenced. The binding-improved mutants with unique sequences were further demonstrated by capture ELISA and sequenced by direct antigen coating ELISA.

A plurality of combinatorial mutants of HAPC-14 were screened, and the top 16 combinatorial mutants with significantly improved affinity were confirmed by KD ELISA (as shown in Nos. 1-16 in Table 2).

TABLE 2

| No. | Name | Capture Elisa OD450 | KD Elisa ranking Bmax | KD Elisa ranking EC50 | VHCDR1 **NYYLN** (SEQ ID NO: 27) | VHCDR2 **DIRLKSNNYE KHYAESVKG** (SEQ ID NO: 28) | VHCDR3 **EGDYFDY** (SEQ ID NO: 29) | VLCDR2 **LASNLES** (SEQ ID NO: 31) | VLCDR3 **QQNNEDPYT** (SEQ ID NO: 32) |
|---|---|---|---|---|---|---|---|---|---|
| | HAPC-14 | 0.0758 | / | / | | | | | |
| 1 | R2-24F3 | 2.7928 | 1.366 | 1.373 | F.... (SEQ ID NO: 33) | .....K.... ......... (SEQ ID NO: 40) | ....... (SEQ ID NO: 29) | ...W.G. (SEQ ID NO: 37) | V........ (SEQ ID NO: 44) |
| 2 | R2-23H2 | 2.6867 | 1.26 | 1.934 | F.... (SEQ ID NO: 33) | .....K.... ......... (SEQ ID NO: 40) | ....... (SEQ ID NO: 29) | ...W.G. (SEQ ID NO: 37) | ......... (SEQ ID NO: 32) |
| 3 | R2-25G5 | 2.6576 | 1.045 | 5.659 | F.... (SEQ ID NO: 33) | .....K.... ......... (SEQ ID NO: 40) | ....... (SEQ ID NO: 29) | ...W.P. (SEQ ID NO: 93) | V........ (SEQ ID NO: 44) |
| 4 | R2-26E4 | 2.5923 | 1.211 | 1.838 | F.... (SEQ ID NO: 33) | .....K.... ......... (SEQ ID NO: 40) | ....... (SEQ ID NO: 29) | ...R.G. (SEQ ID NO: 49) | V........ (SEQ ID NO: 44) |
| 5 | R2-25B7 | 2.5891 | 1.067 | 2.724 | F.... (SEQ ID NO: 33) | .....K.... ......... (SEQ ID NO: 40) | ....... (SEQ ID NO: 29) | ...W.P. (SEQ ID NO: 93) | V........ (SEQ ID NO: 44) |
| 6 | R2-27G7 | 2.58 | 0.7152 | 1.004 | F.... (SEQ ID NO: 33) | .....K.... ......... (SEQ ID NO: 40) | ....... (SEQ ID NO: 29) | ...R.G. (SEQ ID NO: 49) | ......... (SEQ ID NO: 32) |
| 7 | R2-29D9 | 2.5494 | 0.9603 | 7.854 | F.... (SEQ ID NO: 33) | .....K.... ......... (SEQ ID NO: 40) | ...T... (SEQ ID NO: 77) | ...R.P. (SEQ ID NO: 94) | V........ (SEQ ID NO: 44) |
| 8 | R2-24H1 | 2.4255 | 1.251 | 2.517 | F.... (SEQ ID NO: 33) | .....K.... ......... (SEQ ID NO: 40) | ....... (SEQ ID NO: 29) | ...R.G. (SEQ ID NO: 49) | V........ (SEQ ID NO: 44) |
| 9 | R2-22A10 | 2.3922 | 1.015 | 2.679 | F.... (SEQ ID NO: 33) | .....K.... ......... (SEQ ID NO: 40) | ....... (SEQ ID NO: 29) | ...R... (SEQ ID NO: 73) | V........ (SEQ ID NO: 44) |
| 10 | R2-24D4 | 2.373 | 0.7169 | 2.104 | F.... (SEQ ID NO: 33) | .....K.... ......... (SEQ ID NO: 40) | ...T... (SEQ ID NO: 77) | ...W.P. (SEQ ID NO: 93) | ......... (SEQ ID NO: 32) |
| 11 | R2-30F7 | 2.3418 | 0.6171 | 7.274 | F.... (SEQ ID NO: 33) | .......... ......... (SEQ ID NO: 28) | ....... (SEQ ID NO: 29) | ...R.P. (SEQ ID NO: 94) | V........ (SEQ ID NO: 44) |

TABLE 2-continued

| No. | Name | Capture Elisa OD450 | KD Elisa ranking Bmax | KD Elisa ranking EC50 | VHCDR1 NYYLN (SEQ ID NO: 27) | VHCDR2 DIRLKSNNYE KHYAESVKG (SEQ ID NO: 28) | VHCDR3 EGDYFDY (SEQ ID NO: 29) | VLCDR2 LASNLES (SEQ ID NO: 31) | VLCDR3 QQNNEDPYT (SEQ ID NO: 32) |
|---|---|---|---|---|---|---|---|---|---|
| 12 | R2-23E10 | 2.3192 | 1.235 | 1.299 | F.... (SEQ ID NO: 33) | .................. (SEQ ID NO: 28) | ....... (SEQ ID NO: 29) | ...W.G. (SEQ ID NO: 37) | ......... (SEQ ID NO: 32) |
| 13 | R2-22B1 | 2.3056 | 1.225 | 1.194 | F.... (SEQ ID NO: 33) | .....K............ (SEQ ID NO: 40) | ...T... (SEQ ID NO: 77) | ...W.P. (SEQ ID NO: 93) | V........ (SEQ ID NO: 44) |
| 14 | R2-32E6 | 2.1754 | 1.41 | 3.879 | F.... (SEQ ID NO: 27) | .....K............ (SEQ ID NO: 40) | ....... (SEQ ID NO: 29) | ...W.G. (SEQ ID NO: 37) | V........ (SEQ ID NO: 44) |
| 15 | R2-22B6 | 2.1719 | 1.214 | 3.971 | F.... (SEQ ID NO: 33) | .................. (SEQ ID NO: 28) | ....... (SEQ ID NO: 29) | ...R.G. (SEQ ID NO: 49) | ......... (SEQ ID NO: 32) |
| 16 | R2-9C1 | 1.9471 | 1.089 | 1.8 | F.... (SEQ ID NO: 33) | .....K............ (SEQ ID NO: 40) | ....... (SEQ ID NO: 29) | ...W... (SEQ ID NO: 43) | V........ (SEQ ID NO: 44) |

After screening and statistics, it was found that the mutations at the following 6 sites would significantly affect the binding ability of the Fab fragment to the capture antibody. These six sites were:

a) N57R/W located in VL CDR2 (N57R is preferred to N57W);
b) E59G/P located in VL CDR2 (E59G is preferred to E59P);
c) Q93V located in VL CDR3;
d) N31F located in VH CDR1;
e) S55K located in VH CDR2; and
f) Y104T located in VH CDR3.

The most crucial mutant sites were N57R located in the light chain and N31F located in the heavy chain.

Example 3 Anti-aPC Monoclonal Antibodies Based on HAPC-14 Combinatorial Mutation Sites (Constructing Whole IgG1)

3.1 Construction of Anti-aPC Monoclonal Antibodies (HAPC14-1 to HAPC14-10) Based on HAPC14 Combinatorial Mutation Sites Based on the 6 mutation sites in Example 2, a combinatorial construction was carried out to obtain 10 mutants (14-1 to 14-10 in Table 3 below) (HAPC14-1 to HAPC14-10), and then the sequences were constructed into a whole IgG form for expression and purification. The expression level, affinity and other bioactivities of the antibodies were investigated.

Amino acid sequences of HAPC-14 and the 10 mutants are shown in SEQ ID NOs: 5-26.

Humanized antibody 13 (HAPC-13)
Heavy chain (SEQ ID NO: 1)

EVQLVESGGGLVQPGGSLRLSCAASGFTFSNYYLNWVRQAPGKGLEWVGDIRLKSNNYEK

HYAESVKGRFTISRDDSKSITYLQMNSLRAEDTAVYYCAREGDYFDYWGQGTTVTVSS

Light chain (SEQ ID NO: 2)

DIQMTQSPSSLSASVGDRVTITCRASESVDSFGATFMHWYQQKPGKAPKLLIYLASNLESGV

PSRFSGSGSGTDFTLTISSLQPEDFATYYCQQNNEDPYTFGQGTKLEIK

Humanized antibody 16 (HAPC-16)
Heavy chain (SEQ ID NO: 3)

EVQLVESGGGLVQPGGSLRLSCAASGFTFSNYYLNWVRQAPGKGLEWVGDIRLKSNNYEK

HYAESVKGRFTISRDDSKSITYLQMNSLRAEDTAVYYCAREGDYFDYWGQGTTVTVSS

-continued

Light chain (SEQ ID NO: 4)

NIVLTQSPSSLSASVGDRVTITCRASESVDSFGATFMHWYQQKPGKPPKLLIYLASNLESGV

PSRFSGSGSRTDFTLTISSLQPEDFATYYCQQNNEDPYTFGQGTKLEIK

Humanized antibody 14 (HAPC-14)
Heavy chain (SEQ ID NO: 5)

EVQLVESGGGLVQPGGSLRLSCAASGFTFSNYYLNWVRQAPGKGLEWVGDIRLKSNNYEK

HYAESVKGRFTISRDDSKSITYLQMNSLRAEDTAVYYCAREGDYFDYWGQGTTVTVSS

Light chain (SEQ ID NO: 6)

DIQLTQSPSSLSASVGDRVTITCRASESVDSFGATFMHWYQQKPGKAPKLLIYLASNLESGV

PSRFSGSGSGTDFTLTISSLQPEDFATYYCQQNNEDPYTFGQGTKLEIK

HAPC-14-1
Heavy chain (SEQ ID NO: 7)

EVQLVESGGGLVQPGGSLRLSCAASGFTFSFYYLNWVRQAPGKGLEWVGDIRLKSNNYEK

HYAESVKGRFTISRDDSKSITYLQMNSLRAEDTAVYYCAREGDYFDYWGQGTTVTVSS

Light chain (SEQ ID NO: 8)

DIQLTQSPSSLSASVGDRVTITCRASESVDSFGATFMHWYQQKPGKAPKLLIYLASWLGSGV

PSRFSGSGSGTDFTLTISSLQPEDFATYYCQQNNEDPYTFGQGTKLEIK

HAPC-14-2
Heavy chain (SEQ ID NO: 9)

EVQLVESGGGLVQPGGSLRLSCAASGFTFSFYYLNWVRQAPGKGLEWVGDIRLKKNNYEK

HYAESVKGRFTISRDDSKSITYLQMNSLRAEDTAVYYCAREGDYFDYWGQGTTVTVSS

Light chain (SEQ ID NO: 10)

DIQLTQSPSSLSASVGDRVTITCRASESVDSFGATFMHWYQQKPGKAPKLLIYLASWLESGV

PSRFSGSGSGTDFTLTISSLQPEDFATYYCVQNNEDPYTFGQGTKLEIK

HAPC-14-3
Heavy chain (SEQ ID NO: 11)

EVQLVESGGGLVQPGGSLRLSCAASGFTFSFYYLNWVRQAPGKGLEWVGDIRLKKNNYEK

HYAESVKGRFTISRDDSKSITYLQMNSLRAEDTAVYYCAREGDYFDYWGQGTTVTVSS

Light chain (SEQ ID NO: 12)

DIQLTQSPSSLSASVGDRVTITCRASESVDSFGATFMHWYQQKPGKAPKLLIYLASRLGSGV

PSRFSGSGSGTDFTLTISSLQPEDFATYYCVQNNEDPYTFGQGTKLEIK

HAPC-14-4
Heavy chain (SEQ ID NO: 13)

EVQLVESGGGLVQPGGSLRLSCAASGFTFSFYYLNWVRQAPGKGLEWVGDIRLKSNNYEK

HYAESVKGRFTISRDDSKSITYLQMNSLRAEDTAVYYCAREGDYFDYWGQGTTVTVSS

Light chain (SEQ ID NO: 14)

DIQLTQSPSSLSASVGDRVTITCRASESVDSFGATFMHWYQQKPGKAPKLLIYLASRLGSGV

PSRFSGSGSGTDFTLTISSLQPEDFATYYCVQNNEDPYTFGQGTKLEIK

HAPC-14-5
Heavy chain (SEQ ID NO: 15)

EVQLVESGGGLVQPGGSLRLSCAASGFTFSFYYLNWVRQAPGKGLEWVGDIRLKKNNYEK

HYAESVKGRFTISRDDSKSITYLQMNSLRAEDTAVYYCAREGDYFDYWGQGTTVTVSS

-continued

Light chain
(SEQ ID NO: 16)
DIQLTQSPSSLSASVGDRVTITCRASESVDSFGATFMHWYQQKPGKAPKLLIYLASWLGSGV

PSRFSGSGSGTDFTLTISSLQPEDFATYYCVQNNEDPYTFGQGTKLEIK

HAPC-14-6
Heavy chain
(SEQ ID NO: 17)
EVQLVESGGGLVQPGGSLRLSCAASGFTFSFYYLNWVRQAPGKGLEWVGDIRLKKNNYEK

HYAESVKGRFTISRDDSKSITYLQMNSLRAEDTAVYYCAREGDYFDYWGQGTTVTVSS

Light chain
(SEQ ID NO: 18)
DIQLTQSPSSLSASVGDRVTITCRASESVDSFGATFMHWYQQKPGKAPKLLIYLASRLGSGV

PSRFSGSGSGTDFTLTISSLQPEDFATYYCQQNNEDPYTFGQGTKLEIK

HAPC-14-7
Heavy chain
(SEQ ID NO: 19)
EVQLVESGGGLVQPGGSLRLSCAASGFTFSFYYLNWVRQAPGKGLEWVGDIRLKSNNYEK

HYAESVKGRFTISRDDSKSITYLQMNSLRAEDTAVYYCAREGDYFDYWGQGTTVTVSS

Light chain
(SEQ ID NO: 20)
DIQLTQSPSSLSASVGDRVTITCRASESVDSFGATFMHWYQQKPGKAPKLLIYLASRLESGV

PSRFSGSGSGTDFTLTISSLQPEDFATYYCQQNNEDPYTFGQGTKLEIK

HAPC-14-8
Heavy chain
(SEQ ID NO: 21)
EVQLVESGGGLVQPGGSLRLSCAASGFTFSFYYLNWVRQAPGKGLEWVGDIRLKKNNYEK

HYAESVKGRFTISRDDSKSITYLQMNSLRAEDTAVYYCAREGDTFDYWGQGTTVTVSS

Light chain
(SEQ ID NO: 22)
DIQLTQSPSSLSASVGDRVTITCRASESVDSFGATFMHWYQQKPGKAPKLLIYLASRLGSGV

PSRFSGSGSGTDFTLTISSLQPEDFATYYCVQNNEDPYTFGQGTKLEIK

HAPC-14-9
Heavy chain
(SEQ ID NO: 23)
EVQLVESGGGLVQPGGSLRLSCAASGFTFSFYYLNWVRQAPGKGLEWVGDIRLKKNNYEK

HYAESVKGRFTISRDDSKSITYLQMNSLRAEDTAVYYCAREGDTFDYWGQGTTVTVSS

Light chain
(SEQ ID NO: 24)
DIQLTQSPSSLSASVGDRVTITCRASESVDSFGATFMHWYQQKPGKAPKLLIYLASRLGSGV

PSRFSGSGSGTDFTLTISSLQPEDFATYYCQQNNEDPYTFGQGTKLEIK

HAPC-14-1
Heavy chain
(SEQ ID NO: 25)
EVQLVESGGGLVQPGGSLRLSCAASGFTFSNYYLNWVRQAPGKGLEWVGDIRLKKNNYEK

HYAESVKGRFTISRDDSKSITYLQMNSLRAEDTAVYYCAREGDTFDYWGQGTTVTVSS

Light chain
(SEQ ID NO: 26)
DIQLTQSPSSLSASVGDRVTITCRASESVDSFGATFMHWYQQKPGKAPKLLIYLASRLGSGV

PSRFSGSGSGTDFTLTISSLQPEDFATYYCVQNNEDPYTFGQGTKLEIK

HAPC-14
Heavy chain CDR1
(SEQ ID NO: 27)
NYYLN

HAPC-14
Heavy chain CDR2
(SEQ ID NO: 28)
DIRLKSNNYEKHYAESVKG

-continued

HAPC-14
Heavy chain CDR3
(SEQ ID NO: 29)
EGDYFDY

HAPC-14
Light chain CDR1
(SEQ ID NO: 30)
RASESVDSFGATFMH

HAPC-14
Light chain CDR2
(SEQ ID NO: 31)
LASNLES

HAPC-14
Light chain CDR3
(SEQ ID NO: 32)
QQNNEDPYT

HAPC-14-1
Heavy chain CDR1
(SEQ ID NO: 33)
FYYLN

HAPC-14-1
Heavy chain CDR2
(SEQ ID NO: 34)
DIRLKSNNYEKHYAESVKG

HAPC-14-1
Heavy chain CDR3
(SEQ ID NO: 35)
EGDYFDY

HAPC-14-1
Light chain CDR1
(SEQ ID NO: 36)
RASESVDSFGATFMH

HAPC-14-1
Light chain CDR2
(SEQ ID NO: 37)
LASWLGS

HAPC-14-1
Light chain CDR3
(SEQ ID NO: 38)
QQNNEDPYT

HAPC-14-2
Heavy chain CDR1
(SEQ ID NO: 39)
FYYLN

HAPC-14-2
Heavy chain CDR2
(SEQ ID NO: 40)
DIRLKKNNYEKHYAESVKG

HAPC-14-2
Heavy chain CDR3
(SEQ ID NO: 41)
EGDYFDY

HAPC-14-2
Light chain CDR1
(SEQ ID NO: 42)
RASESVDSFGATFMH

HAPC-14-2
Light chain CDR2
(SEQ ID NO: 43)
LASWLES

HAPC-14-2
Light chain CDR3
(SEQ ID NO: 44)
VQNNEDPYT

-continued

HAPC-14-3
Heavy chain CDR1
(SEQ ID NO: 45)
FYYLN

HAPC-14-3
Heavy chain CDR2
(SEQ ID NO: 46)
DIRLKKNNYEKHYAESVKG

HAPC-14-3
Heavy chain CDR3
(SEQ ID NO: 47)
EGDYFDY

HAPC-14-3
Light chain CDR1
(SEQ ID NO: 48)
RASESVDSFGATFMH

HAPC-14-3
Light chain CDR2
(SEQ ID NO: 49)
LASRLGS

HAPC-14-3
Light chain CDR3
(SEQ ID NO: 50)
VQNNEDPYT

HAPC-14-4
Heavy chain CDR1
(SEQ ID NO: 51)
FYYLN

HAPC-14-4
Heavy chain CDR2
(SEQ ID NO: 52)
DIRLKSNNYEKHYAESVKG

HAPC-14-4
Heavy chain CDR3
(SEQ ID NO: 53)
EGDYFDY

HAPC-14-4
Light chain CDR1
(SEQ ID NO: 54)
RASESVDSFGATFMH

HAPC-14-4
Light chain CDR2
(SEQ ID NO: 55)
LASRLGS

HAPC-14-4
Light chain CDR3
(SEQ ID NO: 56)
VQNNEDPYT

HAPC-14-5
Heavy chain CDR1
(SEQ ID NO: 57)
FYYLN

HAPC-14-5
Heavy chain CDR2
(SEQ ID NO: 58)
DIRLKKNNYEKHYAESVKG

HAPC-14-5
Heavy chain CDR3
(SEQ ID NO: 59)
EGDYFDY

HAPC-14-5
Light chain CDR1
(SEQ ID NO: 60)
RASESVDSFGATFMH

-continued

HAPC-14-5
Light chain CDR2
(SEQ ID NO: 61)
LASWLGS

HAPC-14-5
Light chain CDR3
(SEQ ID NO: 62)
VQNNEDPYT

HAPC-14-6
Heavy chain CDR1
(SEQ ID NO: 63)
FYYLN

HAPC-14-6
Heavy chain CDR2
(SEQ ID NO: 64)
DIRLKKNNYEKHYAESVKG

HAPC-14-6
Heavy chain CDR3
(SEQ ID NO: 65)
EGDYFDY

HAPC-14-6
Light chain CDR1
(SEQ ID NO: 66)
RASESVDSFGATFMH

HAPC-14-6
Light chain CDR2
(SEQ ID NO: 67)
LASRLGS

HAPC-14-6
Light chain CDR3
(SEQ ID NO: 68)
QQNNEDPYT

HAPC-14-7
Heavy chain CDR1
(SEQ ID NO: 69)
FYYLN

HAPC-14-7
Heavy chain CDR2
(SEQ ID NO: 70)
DIRLKSNNYEKHYAESVKG

HAPC-14-7
Heavy chain CDR3
(SEQ ID NO: 71)
EGDYFDY

HAPC-14-7
Light chain CDR1
(SEQ ID NO: 72)
RASESVDSFGATFMH

HAPC-14-7
Light chain CDR2
(SEQ ID NO: 73)
LASRLES

HAPC-14-7
Light chain CDR3
(SEQ ID NO: 74)
QQNNEDPYT

HAPC-14-8
Heavy chain CDR1
(SEQ ID NO: 75)
FYYLN

HAPC-14-8
Heavy chain CDR2
(SEQ ID NO: 76)
DIRLKKNNYEKHYAESVKG

-continued

HAPC-14-8
Heavy chain CDR
(SEQ ID NO: 77)
EGDTFDY

HAPC-14-8
Light chain CDR1
(SEQ ID NO: 78)
RASESVDSFGATFMH

HAPC-14-8
Light chain CDR2
(SEQ ID NO: 79)
LASRLGS

HAPC-14-8
Light chain CDR3
(SEQ ID NO: 80)
VQNNEDPYT

HAPC-14-9
Heavy chain CDR1
(SEQ ID NO: 81)
FYYLN

HAPC-14-9
Heavy chain CDR2
(SEQ ID NO: 82)
DIRLKKNNYEKHYAESVKG

HAPC-14-9
Heavy chain CDR3
(SEQ ID NO: 83)
EGDTFDY

HAPC-14-9
Light chain CDR1
(SEQ ID NO: 84)
RASESVDSFGATFMH

HAPC-14-9
Light chain CDR2
(SEQ ID NO: 85)
LASRLGS

HAPC-14-9
Light chain CDR3
(SEQ ID NO: 86)
QQNNEDPYT

HAPC-14-10
Heavy chain CDR1
(SEQ ID NO: 87)
NYYLN

HAPC-14-10
Heavy chain CDR2
(SEQ ID NO: 88)
DIRLKKNNYEKHYAESVKG

HAPC-14-10
Heavy chain CDR3
(SEQ ID NO: 89)
EGDTFDY

HAPC-14-10
Light chain CDR1
(SEQ ID NO: 90)
RASESVDSFGATFMH

HAPC-14-10
Light chain CDR2
(SEQ ID NO: 91)
LASRLGS

-continued

HAPC-14-10
Light chain CDR3

(SEQ ID NO: 92)

VQNNEDPYT

Detailed information is shown in Table 3.

TABLE 3

| Back bone Entry | hIgG1 Mutations | H chain | L chain |
|---|---|---|---|
| 1 | L57W, L59G, H31F | EVQLVESGGGLVQPGGSLRLSCAASGFTFSFYYLN WVRQAPGKGLEWVGDIRLKSNNYEKHYAESVKGR FTISRDDSKSITYLQMNSLRAEDTAVYYCAREGDYF DYWGQGTTVTVSS (SEQ ID NO: 7) | DIQLTQSPSSLSASVGDRVTITCRASESVDSFGATF MHWYQQKPGKAPKLLIYLASWLGSGVPSRFSGSG SGTDFTLTISSLQPEDFATYYCQQNNEDPYTFGQG TKLEIK (SEQ ID NO: 8) |
| 2 | L57W, L93V, H31F, H55K | EVQLVESGGGLVQPGGSLRLSCAASGFTFSFYYLN WVRQAPGKGLEWVGDIRLKKNNYEKHYAESVKGR FTISRDDSKSITYLQMNSLRAEDTAVYYCAREGDYF DYWGQGTTVTVSS (SEQ ID NO: 9) | DIQLTQSPSSLSASVGDRVTITCRASESVDSFGATF MHWYQQKPGKAPKLLIYLASWLESGVPSRFSGSG SGTDFTLTISSLQPEDFATYYCVQNNEDPYTFGQG TKLEIK (SEQ ID NO: 10) |
| 3 | L57R, L59G, L93V, H31F, H55K | EVQLVESGGGLVQPGGSLRLSCAASGFTFSFYYLN WVRQAPGKGLEWVGDIRLKKNNYEKHYAESVKGR FTISRDDSKSITYLQMNSLRAEDTAVYYCAREGDYF DYWGQGTTVTVSS (SEQ ID NO: 11) | DIQLTQSPSSLSASVGDRVTITCRASESVDSFGATF MHWYQQKPGKAPKLLIYLASRLGSGVPSRFSGSG SGTDFTLTISSLQPEDFATYYCVQNNEDPYTFGQG TKLEIK (SEQ ID NO: 12) |
| 4 | L57R, L59G, L93V, H31F | EVQLVESGGGLVQPGGSLRLSCAASGFTFSFYYLN WVRQAPGKGLEWVGDIRLKSNNYEKHYAESVKGR FTISRDDSKSITYLQMNSLRAEDTAVYYCAREGDYF DYWGQGTTVTVSS (SEQ ID NO: 13) | DIQLTQSPSSLSASVGDRVTITCRASESVDSFGATF MHWYQQKPGKAPKLLIYLASRLGSGVPSRFSGSG SGTDFTLTISSLQPEDFATYYCVQNNEDPYTFGQG TKLEIK (SEQ ID NO: 14) |
| 5 | L57W, L59G, L93V, H31F, H55K | EVQLVESGGGLVQPGGSLRLSCAASGFTFSFYYLN WVRQAPGKGLEWVGDIRLKKNNYEKHYAESVKGR FTISRDDSKSITYLQMNSLRAEDTAVYYCAREGDYF DYWGQGTTVTVSS (SEQ ID NO: 15) | DIQLTQSPSSLSASVGDRVTITCRASESVDSFGATF MHWYQQKPGKAPKLLIYLASWLGSGVPSRFSGSG SGTDFTLTISSLQPEDFATYYCVQNNEDPYTFGQG TKLEIK (SEQ ID NO: 16) |
| 6 | L57R, L59G, H31F, H55K | EVQLVESGGGLVQPGGSLRLSCAASGFTFSFYYLN WVRQAPGKGLEWVGDIRLKKNNYEKHYAESVKGR FTISRDDSKSITYLQMNSLRAEDTAVYYCAREGDYF DYWGQGTTVTVSS (SEQ ID NO: 17) | DIQLTQSPSSLSASVGDRVTITCRASESVDSFGATF MHWYQQKPGKAPKLLIYLASRLGSGVPSRFSGSG SGTDFTLTISSLQPEDFATYYCQQNNEDPYTFGQG TKLEIK (SEQ ID NO: 18) |
| 7 | L57R, H31F | EVQLVESGGGLVQPGGSLRLSCAASGFTFSFYYLN WVRQAPGKGLEWVGDIRLKSNNYEKHYAESVKGR FTISRDDSKSITYLQMNSLRAEDTAVYYCAREGDYF DYWGQGTTVTVSS (SEQ ID NO: 19) | DIQLTQSPSSLSASVGDRVTITCRASESVDSFGATF MHWYQQKPGKAPKLLIYLASRLESGVPSRFSGSGS GTDFTLTISSLQPEDFATYYCQQNNEDPYTFGQGT KLEIK (SEQ ID NO: 20) |
| 8 | L57R, L59G, L93V, H31F, H55K, H104T | EVQLVESGGGLVQPGGSLRLSCAASGFTFSFYYLN WVRQAPGKGLEWVGDIRLKKNNYEKHYAESVKGR FTISRDDSKSITYLQMNSLRAEDTAVYYCAREGDTF DYWGQGTTVTVSS (SEQ ID NO: 21) | DIQLTQSPSSLSASVGDRVTITCRASESVDSFGATF MHWYQQKPGKAPKLLIYLASRLGSGVPSRFSGSG SGTDFTLTISSLQPEDFATYYCVQNNEDPYTFGQG TKLEIK (SEQ ID NO: 22) |
| 9 | L57R, L59G, H31F, H55K, H104T | EVQLVESGGGLVQPGGSLRLSCAASGFTFSFYYLN WVRQAPGKGLEWVGDIRLKKNNYEKHYAESVKGR FTISRDDSKSITYLQMNSLRAEDTAVYYCAREGDTF DYWGQGTTVTVSS (SEQ ID NO: 23) | DIQLTQSPSSLSASVGDRVTITCRASESVDSFGATF MHWYQQKPGKAPKLLIYLASRLGSGVPSRFSGSG SGTDFTLTISSLQPEDFATYYCQQNNEDPYTFGQG TKLEIK (SEQ ID NO: 24) |
| 10 | L57R, L59G, H55K, H104T | EVQLVESGGGLVQPGGSLRLSCAASGFTFSNYYLN WVRQAPGKGLEWVGDIRLKKNNYEKHYAESVKGR FTISRDDSKSITYLQMNSLRAEDTAVYYCAREGDTF DYWGQGTTVTVSS (SEQ ID NO: 25) | DIQLTQSPSSLSASVGDRVTITCRASESVDSFGATF MHWYQQKPGKAPKLLIYLASRLGSGVPSRFSGSG SGTDFTLTISSLQPEDFATYYCVQNNEDPYTFGQG TKLEIK (SEQ ID NO: 26) |

The underlined parts are CDRs, and the other parts are framework regions.

Humanized antibody 14 (anti-aPC monoclonal antibody 14)

```
Heavy chain
                                         (SEQ ID NO: 5)
EVQLVESGGGLVQPGGSLRLSCAASGFTFSNYYLNWVRQAPGKGLEWVG

DIRLKSNNYEKHYAESVKGRFTISRDDSKSITYLQMNSLRAEDTAVYYC

AREGDYFDYWGQGTTVTVSS

Light chain
                                         (SEQ ID NO: 6)
DIQLTQSPSSLSASVGDRVTITCRASESVDSFGATFMHWYQQKPGKAPK

LLIYLASNLESGVPSRFSGSGSGTDFTLTISSLQPEDFATYYCQQNNED

PYTFGQGTKLEIK
```

The underlined parts are CDRs, the other parts are framework regions, and bold fonts indicate humanized sites.

| Protein number | mutation sites |
|---|---|
| HPAC14-1 | L57W, L59G, H31F |
| HPAC14-2 | L57W, L93V, H31F, H55K |
| HPAC14-3 | L57R, L59G, L93V, H31F, H55K |
| HPAC14-4 | L57R, L59G, L93V, H31F |
| HPAC14-5 | L57W, L59G, L93V, H31F, H55K |
| HPAC14-6 | L57R, L59G, H31F, H55K |
| HPAC14-7 | L57R, H31F |
| HPAC14-8 | L57R, L59G, L93V, H31F, H55K, H104T |
| HPAC14-9 | L57R, L59G, H31F, H55K, H104T |
| HPAC14-10 | L57R, L59G, L93V, H55K, H104T |
| HAPC14 | |

3.2 Assays of Binding Abilities of Anti-aPC Monoclonal Antibodies Constructed Based on HAPC14 Combinatorial Mutation Sites to haPC/hPC (HAPC14-1 to HAPC14-10)

Assay Method:

The binding abilities of the anti-aPC monoclonal antibodies to haPC/hPC were assayed by Elisa.

1. ELISA plates were coated with haPC/hPC (1 μg/mL in PBS), 100 μL/well, at 4° C. overnight.
2. The plates were washed 3 times with PBST (0.1% Tween 20), 200 μL/well.
3. The plates were blocked with 2% BSA (PBS solution), 200 μL/well, at room temperature for 1 hour.
4. The plates were washed 3 times with PBST (0.1% Tween 20), 200 μL/well.
5. The plates were incubated with anti-aPC monoclonal antibody as primary antibody (diluted from 10 μg/mL in 2% BSA), 100 μL/well, at room temperature for 1 hour.
6. The plates were washed 3 times with PBST (0.1% Tween 20), 200 μL/well.
7. The plates were incubated with anti-hIgG-Fc antibody-HRP (diluted 5000-fold in 2% BSA buffer) at room temperature for 1 hour.
8. The plates were washed 6 times with PBST (0.1% Tween 20), 200 μL/well.
9. The plates were incubated with a TMB substrate (prepared from solutions A and B at 1:1 (v/v)), 100 μL/well, away from light for 10 minutes.
10. The reaction was quenched with HCl (1 M), 100 μL/well, and OD450 was read.

The assay results are shown in FIG. 3, Table 4 and Table 5. As can be seen, the anti-aPC monoclonal antibodies bind to hAPC and do not bind to hPC.

TABLE 4

| Antigen | Antibody | EC50 (nM) | Span |
|---|---|---|---|
| hAPC | HAPC14-1 | 0.1141 | 2.106 |
| | HAPC14-2 | 0.111 | 1.775 |
| | HAPC14-3 | 0.0618 | 1.615 |
| | HAPC14-4 | 0.06052 | 1.52 |
| | HAPC14-5 | 0.09239 | 1.631 |
| | HAPC14-6 | 0.08212 | 1.854 |
| | HAPC14-7 | 0.1304 | 1.578 |
| | HAPC14-8 | 0.1382 | 1.046 |
| | HAPC14-9 | 0.07608 | 1.07 |
| | HAPC14-10 | 0.2799 | 0.7453 |
| | HAPC14 | 0.2203 | 0.2909 |

TABLE 5

| Antigen | Antibody | Span |
|---|---|---|
| hPC | HAPC14-1 | 0.023 |
| | HAPC14-2 | 0.01042 |
| | HAPC14-3 | about 0.2673 |
| | HAPC14-4 | 0.1571 |
| | HAPC14-5 | about 0.04753 |
| | HAPC14-6 | about 0.01332 |
| | HAPC14-7 | about 0.006612 |
| | HAPC14-8 | −0.004647 |
| | HAPC14-9 | 0.012 |
| | HAPC14-10 | about 0.001450 |
| | HAPC14 | about 0.03871 |

3.3 Assays of Affinities of Anti-aPC Monoclonal Antibodies Constructed Based on HAPC-14 Combinatorial Mutation Sites Using Octet System for Biomolecular Interactions (HAPC-14-1 to HAPC-14-10)

Assay method: Octet analysis was carried out at 25° C. using a Protein A Octet biosensor in 1× Kinetics buffer. During the kinetics assay, the baseline step assay was run in 1× Kinetics buffer for 120 seconds, and then run for 240 seconds after the antibody was loaded to the biosensor. Next, the baseline 2 step assay was run in 1× Kinetics buffer for 120 seconds. Then, the biosensor with the capture antibody was immersed in wells containing antigen (huAPC) of 5 diluted concentrations (3.13 nM, 6.25 nM, 12.5 nM, 25 nM and 50 nM) for 180 seconds, and then dissociation was carried out in 1× Kinetics buffer for 400 seconds. The 1× Kinetics buffer was used as a blank control to show the natural dissociation of the antibody in the buffer. 10 mM glycine at pH 1.5 was used for the regeneration step. Octet data analysis software was used to calculate binding kinetics, and a 1:1 binding model was used for curve fitting.

The affinities of the mutant antibodies were assayed at pH 7.4. The results are shown in FIG. 4 and Table 6:

TABLE 6

| Sample | KD (M) | kon (1/Ms) | kdis (1/s) | Full R^2 |
|---|---|---|---|---|
| HAPC14-1 | 3.83E−09 | 3.06E+05 | 1.17E−03 | 0.9932 |
| HAPC14-2 | 3.78E−09 | 3.07E+05 | 1.16E−03 | 0.9877 |
| HAPC14-3 | 2.67E−09 | 3.20E+05 | 8.54E−04 | 0.9933 |
| HAPC14-4 | 4.06E−09 | 3.10E+05 | 1.26E−03 | 0.9911 |
| HAPC14-5 | 2.83E−09 | 3.22E+05 | 9.11E−04 | 0.9924 |
| HAPC14-6 | 3.64E−09 | 2.97E+05 | 1.08E−03 | 0.9917 |
| HAPC14-7 | 7.72E−09 | 2.56E+05 | 1.97E−03 | 0.9929 |
| HAPC14-8 | 1.05E−08 | 2.50E+05 | 2.62E−03 | 0.9901 |
| HAPC14-9 | 9.69E−09 | 2.45E+05 | 2.38E−03 | 0.9917 |
| HAPC14-10 | 1.90E−08 | 2.25E+05 | 4.28E−03 | 0.9906 |
| HAPC14 | 2.54E−07 | 6.40E+04 | 1.62E−02 | 0.9866 |

As can be seen from the results in FIG. 4 and Table 6, the mutated antibodies could still bind to haPC, but could not bind to hPC, and their affinities were increased as compared with the unmutated No. 14 antibody HAPC-14. Especially No. 6 (HAPC14-6) and No. 3 (HAPC14-3) showed a nearly 100-times increase.

Example 4 Cleavage of Histones by Anti-aPC Monoclonal Antibody HAPC14-6 and aPC

Assay Method:

| Reagent | Content (ug/μL) | Incubation |
|---|---|---|
| Calf thymus histone in each tube | 0.2 | 37° C. 4 h |
| aPC present or absent in each tube | When aPC was present, its content was 0.012 | |
| HAPC present or absent in each tube | When HAPC was present, its content was 0.06 | |
| PBS Buffer at pH 7.3 was added until the reaction volume reached 100 ul | | |

After SDS-PAGE, Coomassie Blue staining was carried out, and whether the HAPC monoclonal antibody promoted or inhibited the cleavage of histones by aPC was observed.

Figure 5:
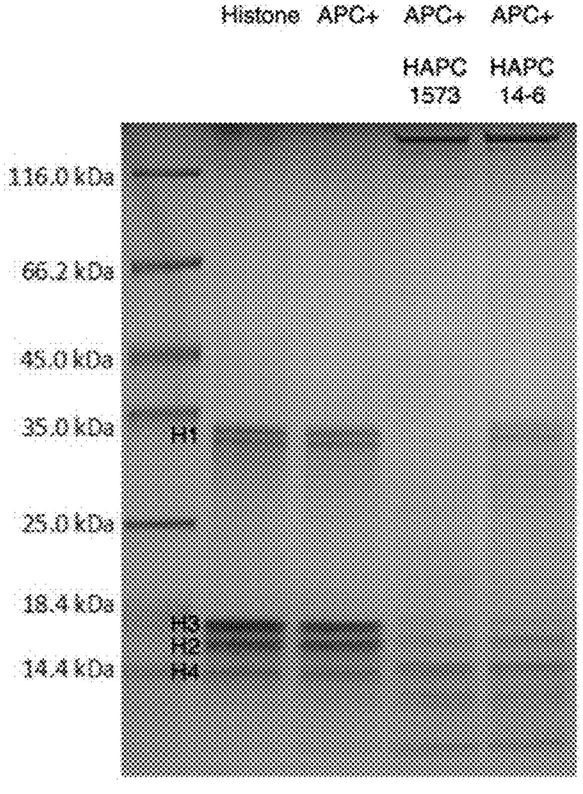
FIG. 5 shows effects of HAPC-14 mutant antibody HAPC-14-6 on the ability of aPC to cleave histones.

The assay results are shown in FIG. 5 (from left to right in FIG. 5: containing histones only; containing histones and APC; containing histones, APC and HAPC1573; containing histones, APC and HAPC14-6). As can be seen, HAPC1573 and HAPC14-6 promoted the ability of aPC to cleave histones, which indicated that the HAPC14-6 monoclonal antibody of the present disclosure could provide the cyto-protective effect against cytotoxicity of the histones H3 and H4.

Consistent with HAPC1573, HAPC-14-6 did not inhibit, but actually promoted the cleavage of histones H3 and H4 by aPC. Different from HAPC1573, HAPC-14-6 slightly inhibited the cleavage of histone H1 by aPC. This indicated that HAPC-14-6 could provide the cytoprotective effect against cytotoxicity of the histones H3 and H4.

Example 5 In Vitro Pharmacodynamic Studies of Anti-aPC Monoclonal Antibodies HAPC-14-3 and HAPC-14-6

In this example, the effects of different antibodies at different concentrations on coagulation factor-deficient plasma were assayed.

Protc-induced APTT experiments were used to measure the minimum dose of monoclonal antibody to inhibit the anticoagulant activity of aPC in human plasma deficient in multiple coagulation factors. It was found that a concentration of at most 1 ug/mg could inhibit 95% or more of the anticoagulant activity of aPC, while a concentration of 100 ug/ml or above was required for HAPC1573.

5.1 Experimental Method and Principle

Principle of activated partial thromboplastin time (APTT) assay: At 37° C., factors XII and XI were activated with kaolin, platelet factor 3 was replaced with cephalin (partial thromboplastin), and in the presence of $Ca^{2+}$, the time required by clotting of plasma was observed, which was the activated partial thromboplastin time. The APTT assay is a sensitive and most commonly used screening test for the intrinsic coagulation system.

The newly developed anti-aPC monoclonal antibody HAPC-14-6 at a concentration of at most 1 μg/ml could inhibit the anticoagulant activity of aPC in human plasma deficient in various coagulation factors, including human plasma deficient in coagulation factor V, coagulation factor VII, coagulation factor VIII, coagulation factor IX, coagulation factor X, coagulation factor XI, coagulation factor XII, VWF and the like.

5.2 Assay of Effects of Antibodies on Coagulation Factor-Deficient Plasma (1) Experimental Result of Effects of Different Antibodies at Different Concentrations on Coagulation Factor VIII and VIX-Deficient Plasma Experimental method: The antibodies were diluted to corresponding concentrations with OWREN-KOLLER buffer.

Coagulation factor FVIII-deficient plasma+antibodies at various dilutions in Table 7 (final concentration)+0.05 U/ml Protac (final concentration)+OWREN-KOLLER buffer, at room temperature for 15 min.

| 150 μl | total 150 ul |
|---|---|

Control: coagulation factor FVIII-deficient plasma 150 μl+OWREN-KOLLER buffer 150 μl.

Assay method: STAGO Compact Max APTT-procedure.

Coagulation factor FIX-deficient plasma+antibodies at various dilutions in Table 7 (final concentration)+0.01 U/ml Protac (final concentration)+OWREN-KOLLER buffer, at room temperature for 15 min.

| 150 μl | total 150 ul |
|---|---|

Control: coagulation factor FIX-deficient plasma 150 μl+OWREN-KOLLER buffer 150 μl.

Assay method: STAGO Compact Max APTT-procedure.

Assay result: As shown in Table 7, in the coagulation factor VIII and VIX-deficient plasma, the anti-aPC monoclonal antibodies HAPC14-1 to HAPC14-10 could inhibit the anticoagulant activity of aPC to different degrees. At the same antibody concentration, the anti-aPC monoclonal antibodies HAPC14-1 to HAPC14-10 all had better effects in inhibiting the anticoagulant activity of aPC than the murine antibodies 1573, HAPC13 and HAPC14.

TABLE 7

| Antibody | APC-antibody concentration (μg/ml) | Mean clotting time (s) | |
|---|---|---|---|
| | | FVIII-deficient plasma | FIX-deficient plasma |
| 1573 | 5 | 388.9 | 403.5 |
| | 1 | 629 | 566.8 |
| | 0.5 | 600 | 584.2 |
| HAPC-13 | 5 | 300.7 | 325.7 |
| | 1 | 546.3 | 402.3 |
| | 0.5 | 628.8 | 502.1 |
| HAPC-14 | 5 | 324.4 | 310.2 |
| | 1 | 457.3 | 415.3 |
| | 0.5 | 574.5 | 457 |
| HAPC14-1 | 5 | 165.8 | 171.3 |
| | 1 | 222.5 | 194.6 |
| | 0.5 | 327.1 | 219.3 |
| HAPC14-2 | 5 | 158.9 | 142.9 |
| | 1 | 195.6 | 210.8 |
| | 0.5 | 358.4 | 233.2 |
| HAPC14-3 | 5 | 176.4 | 185.1 |
| | 1 | 188 | 199.6 |
| | 0.5 | 205.2 | 208.4 |
| HAPC14-4 | 5 | 158.3 | 176.2 |
| | 1 | 184.3 | 193.7 |
| | 0.5 | 220.6 | 219.6 |
| HAPC14-5 | 5 | 171.2 | 166.1 |
| | 1 | 200.2 | 187.5 |
| | 0.5 | 223.9 | 197.4 |
| HAPC14-6 | 5 | 161.7 | 179.5 |
| | 1 | 186.9 | 198.5 |
| | 0.5 | 182.3 | 181.3 |
| HAPC14-7 | 5 | 175.5 | 146.5 |
| | 1 | 197.9 | 145.4 |
| | 0.5 | 296.7 | 240.9 |
| HAPC14-8 | 0.5 | 189.7 | 276.4 |
| | 0.1 | 251.9 | 392 |
| | 0.05 | 315.9 | 732 |
| HAPC14-9 | 0.5 | 181.6 | 170 |
| | 0.25 | — | 497.8 |
| | 0.1 | 217.3 | 610.8 |
| | 0.05 | 261.6 | 670.1 |
| HAPC14-10 | 1 | — | 158.2 |
| | 0.5 | 254.5 | 330.7 |
| | 0.1 | 309.1 | 595.5 |
| | 0.05 | 414.6 | 733.3 |

(2) Experimental Result of Effects of Different Antibodies at Different Concentrations on Coagulation Factor FVIII-Deficient Plasma Experimental method: The antibodies were diluted to corresponding concentrations with OWREN-KOLLER buffer.

Figure 6A:
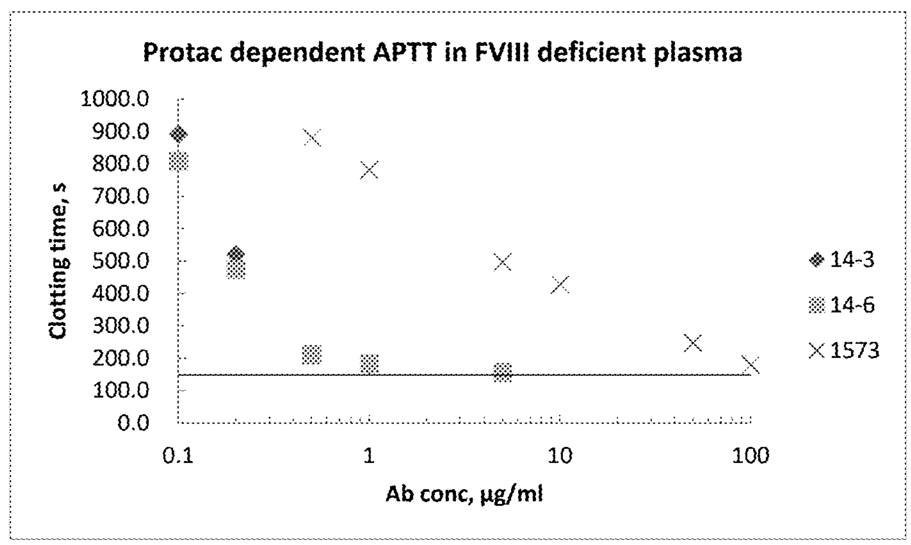
FIG. 6 shows in vitro pharmacodynamic experiments. Functions of HAPC-14 mutant antibodies HAPC-14-3 and HAPC-14-6 on inhibiting the anticoagulant activity of aPC in coagulation factor-deficient plasma: A: for coagulation factor FVIII-deficient plasma, B: for coagulation factor FIX-deficient plasma, C: for coagulation factor FXI-deficient plasma, D: for coagulation factor FVII-deficient plasma, E: for coagulation factor FXII-deficient plasma, F: for coagulation factor FV-deficient plasma, G: for coagulation factor FX-deficient plasma, H: for VWF-deficient plasma.

Coagulation factor FVIII-deficient plasma+antibodies at various dilutions in FIG. 6A (final concentration)+0.05 U/ml Protac (final concentration)+OWREN-KOLLER buffer, at room temperature for 15 min.

| 150 μl | total 150 ul |
|---|---|

Control: coagulation factor FVIII-deficient plasma 150 μl+OWREN-KOLLER buffer 150 μl.

Assay method: STAGO Compact Max APTT-procedure.

Experimental result: As shown in FIG. 6A, in the coagulation factor FVIII-deficient plasma, the anti-aPC monoclonal antibodies completely inhibited the anticoagulant activity of aPC.

(3) Experimental Result of Effects of Different Antibodies at Different Concentrations on Coagulation Factor FIX-Deficient Plasma Experimental method: The antibodies were diluted to corresponding concentrations with OWREN-KOLLER buffer.

Figure 6B:
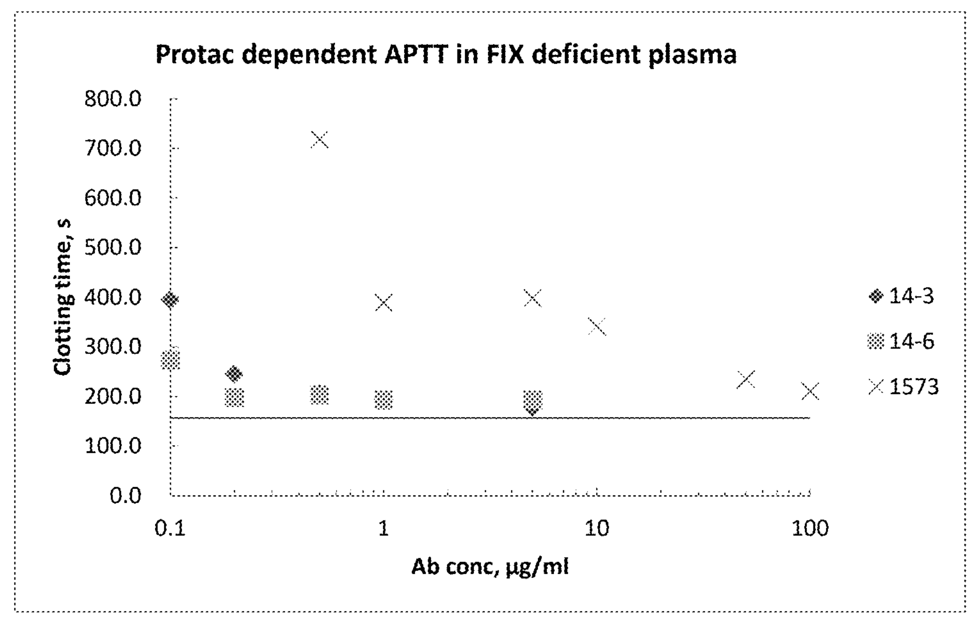

Coagulation factor FIX-deficient plasma+antibodies at various dilutions in FIG. 6B (final concentration)+0.01 U/ml Protac (final concentration)+OWREN-KOLLER buffer, at room temperature for 15 min.

| 150 μl | total 150 ul |
|---|---|

Control: coagulation factor FIX-deficient plasma 150 μl+OWREN-KOLLER buffer 150 μl.

Assay method: STAGO Compact Max APTT-procedure.

Assay result: As shown in FIG. 6B, in the coagulation factor FIX-deficient plasma, the anti-aPC monoclonal antibodies completely inhibited the anticoagulant activity of aPC.

(4) Experimental Result of Effects of Different Antibodies at Different Concentrations on Coagulation Factor FXI-Deficient Plasma Experimental method: The antibodies were diluted to corresponding concentrations with OWREN-KOLLER buffer.

Figure 6C:
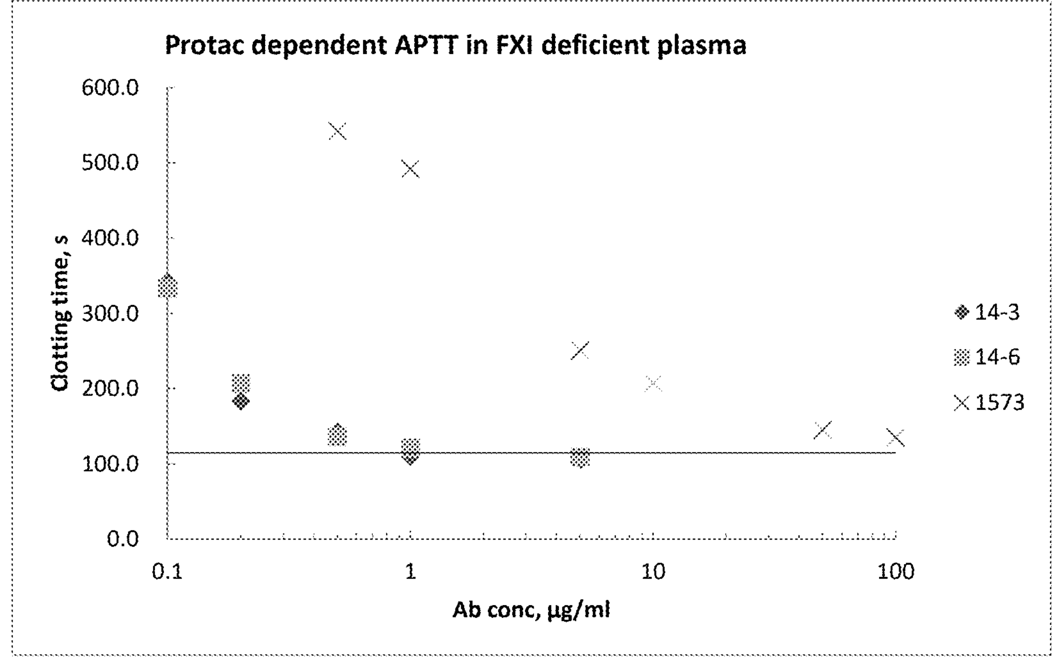

Coagulation factor FXI-deficient plasma+antibodies at various dilutions in FIG. 6C (final concentration)+0.06 U/ml Protac (final concentration)+OWREN-KOLLER buffer, at room temperature for 15 min.

| 150 μl | total 150 ul |
|---|---|

Control: coagulation factor FXI-deficient plasma 150 μl+OWREN-KOLLER buffer 150 μl.

Assay method: STAGO Compact Max APTT-procedure.

Assay result: As shown in FIG. 6C, in the coagulation factor FXI-deficient plasma, the anti-aPC monoclonal antibodies completely inhibited the anticoagulant activity of aPC.

(5) Experimental Result of Effects of Different Antibodies at Different Concentrations on Coagulation Factor FVII-Deficient Plasma Experimental method: The antibodies were diluted to corresponding concentrations with OWREN-KOLLER buffer.

Figure 6D:
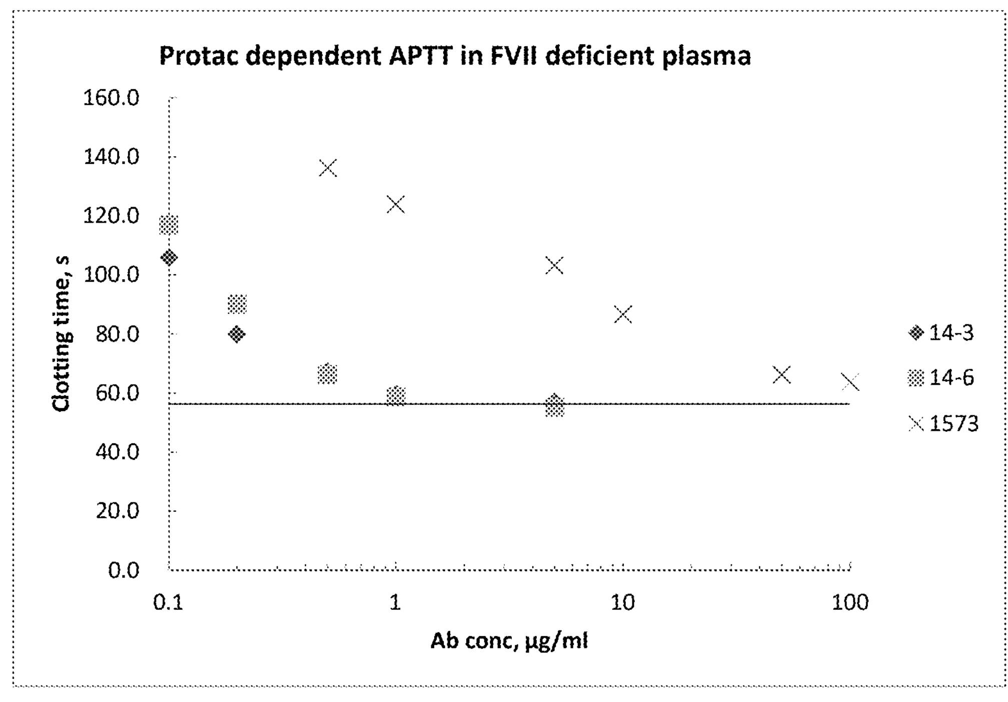

Coagulation factor FVII-deficient plasma+antibodies at various dilutions in FIG. 6D (final concentration)+0.1 U/ml Protac (final concentration)+OWREN-KOLLER buffer, at room temperature for 15 min.

| 150 μl | total 150 ul |
|---|---|

Control: coagulation factor FVII-deficient plasma 150 μl+OWREN-KOLLER buffer 150 μl.

Assay method: STAGO Compact Max APTT-procedure.

Assay result: As shown in FIG. 6D, in the coagulation factor FVII-deficient plasma, the anti-aPC monoclonal antibodies completely inhibited the anticoagulant activity of aPC.

(6) Experimental Result of Effects of Different Antibodies at Different Concentrations on Coagulation Factor FXII-Deficient Plasma Experimental method: The antibodies were diluted to corresponding concentrations with OWREN-KOLLER buffer.

Figure 6E:
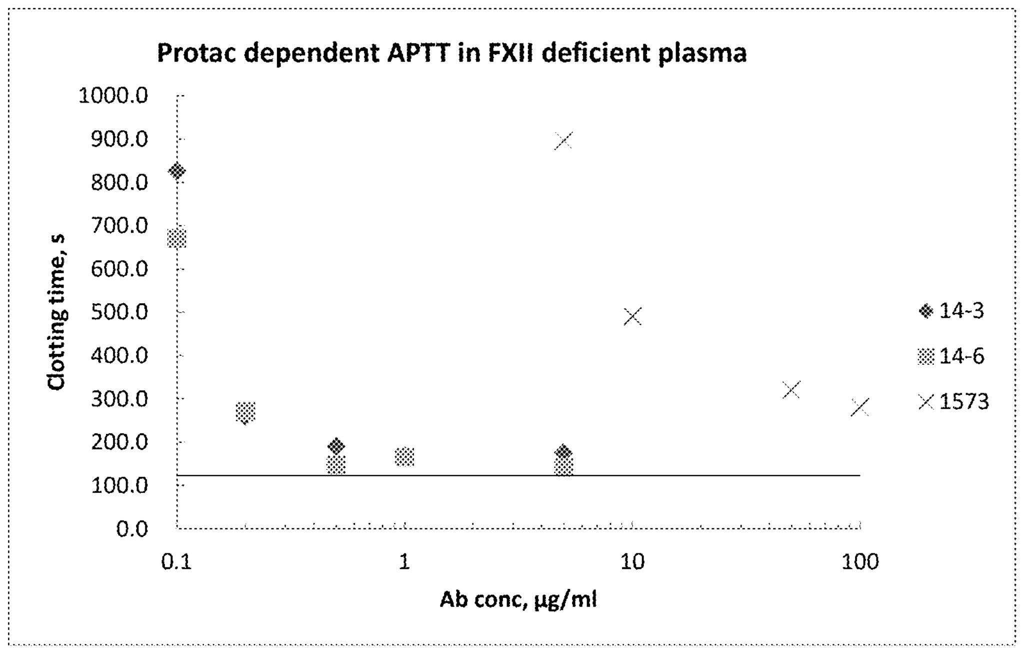

Coagulation factor FXII-deficient plasma+antibodies at various dilutions in FIG. 6E (final concentration)+0.025 U/ml Protac (final concentration)+OWREN-KOLLER buffer, at room temperature for 15 min.

| 150 μl | total 150 ul |
|---|---|

Control: coagulation factor FXII-deficient plasma 150 μl+OWREN-KOLLER buffer 150 μl.

Assay method: STAGO Compact Max APTT-procedure.

Assay result: As shown in FIG. 6E, in the coagulation factor FXII-deficient plasma, the anti-aPC monoclonal antibodies completely inhibited the anticoagulant activity of aPC.

(7) Experimental Result of Effects of Different Antibodies at Different Concentrations on Coagulation Factor FV-Deficient Plasma Experimental method: The antibodies were diluted to corresponding concentrations with OWREN-KOLLER buffer.

Figure 6F:
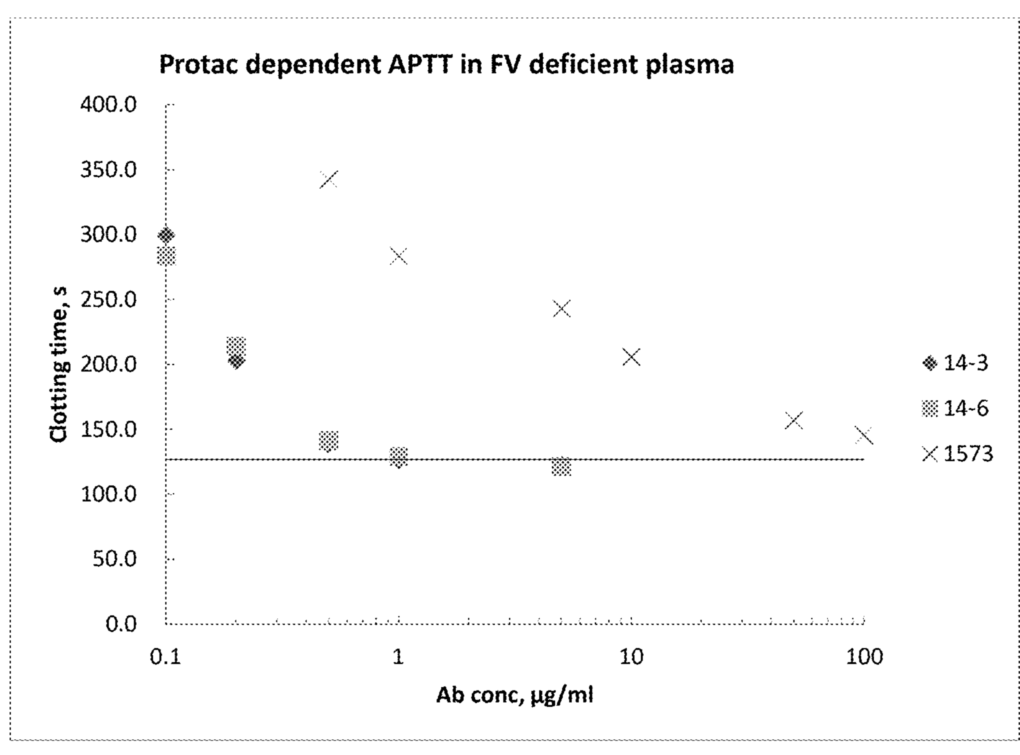

Coagulation factor FV-deficient plasma (containing 5% standard plasma)+antibodies at various dilutions in FIG. 6F (final concentration)+0.05 U/ml Protac (final concentration)+OWREN-KOLLER buffer, at room temperature for 15 min.

| 150 μl | total 150 ul |
|---|---|

Control: coagulation factor FV-deficient plasma (containing 5% standard plasma) 150 μl+OWREN-KOLLER buffer 150 μl.

Assay method: STAGO Compact Max APTT-procedure.

Assay result: As shown in FIG. 6F, in the coagulation factor FV-deficient plasma, the anti-aPC monoclonal antibodies completely inhibited the anticoagulant activity of aPC.

(8) Experimental Result of Effects of Different Antibodies at Different Concentrations on Coagulation Factor FX-Deficient Plasma Experimental method: The antibodies were diluted to corresponding concentrations with OWREN-KOLLER buffer.

Figure 6G:
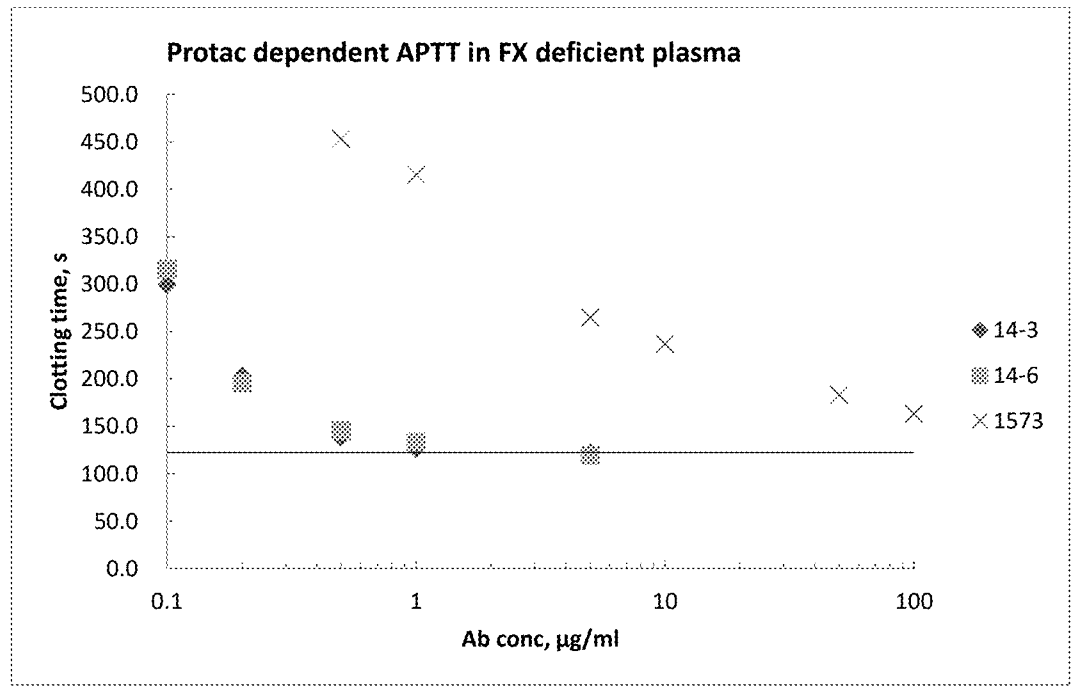

Coagulation factor FX-deficient plasma (containing 1% standard plasma)+antibodies at various dilutions in FIG. 6G (final concentration)+0.05 U/ml Protac (final concentration)+OWREN-KOLLER buffer, at room temperature for 15 min.

| 150 μl | total 150 ul |
|---|---|

Control: coagulation factor FX-deficient plasma (containing 1% standard plasma) 150 μl+OWREN-KOLLER buffer 150 μl.

Assay method: STAGO Compact Max APTT-procedure.

Assay result: As shown in FIG. 6G, in the coagulation factor FX-deficient plasma, the anti-aPC monoclonal antibodies completely inhibited the anticoagulant activity of aPC.

(9) Experimental Result of Effects of Different Antibodies at Different Concentrations on Coagulation Factor VWF-Deficient Plasma Experimental method: The antibodies were diluted to corresponding concentrations with OWREN-KOLLER buffer.

Figure 6H:
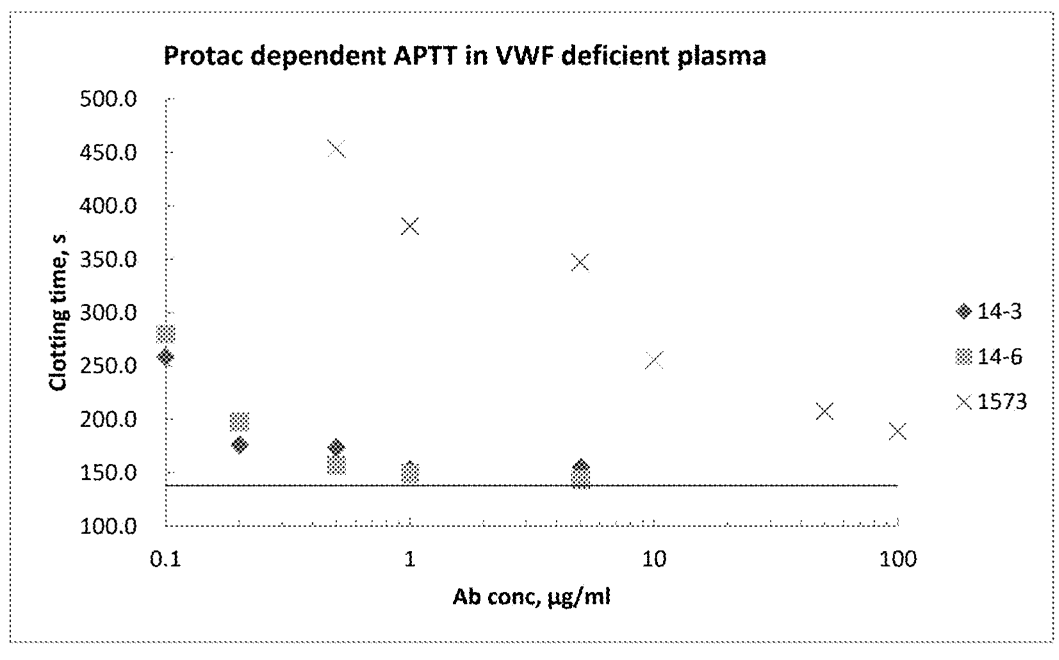

Coagulation factor VWF-deficient plasma+antibodies at various dilutions in FIG. 6H (final concentration)+0.01 U/ml Protac (final concentration)+OWREN-KOLLER buffer, at room temperature for 15 min.

| 150 μl | total 150 ul |
|---|---|

Control: coagulation factor VWF-deficient plasma 150 μl+OWREN-KOLLER buffer 150 μl.

Assay method: STAGO Compact Max APTT-procedure.

Assay result: As shown in FIG. 6H, in the coagulation factor VWF-deficient plasma, the anti-aPC monoclonal antibodies completely inhibited the anticoagulant activity of aPC.

Example 6 In Vivo Pharmacodynamic Experiment

In the humanized protein C hemophilia mouse model (referring to paragraphs [0230] to [0238] in Chinese patent application No. CN201911027061.6), after a certain dose of the anti-aPC monoclonal antibody was injected into mice, the bleeding volume after tail tip amputation was measured to determine the coagulation effect of the anti-aPC monoclonal antibody by inhibiting the anticoagulant function of aPC.

6.1 Experimental Method

The administration was performed by intravenous injection through the canthus of the mouse. 1 hour after the administration, the mice were anesthetized by intraperitoneal injection of sodium pentobarbital. The tail of the anesthetized mouse was cut off 2 mm from the tail tip of the mouse, and the wound of the tail was immersed in 15 ml of saline at 37° C. to collect blood from the mouse. After 20 minutes, the collection was stopped. After red blood cells in the collected solution were lysed, a supernatant was collected by centrifugation. The supernatant was tested using an ultraviolet spectrophotometer at a wavelength of 600 nm. A measured OD value was used to represent the bleeding volume of the mouse, which was used to measure the coagulation function of the mouse. WT represented normal mice, and untreated represented unadministered humanized protein C hemophilia A mice or unadministered humanized protein C hemophilia B mice.

6.2 Experimental Result

Figure 7A:
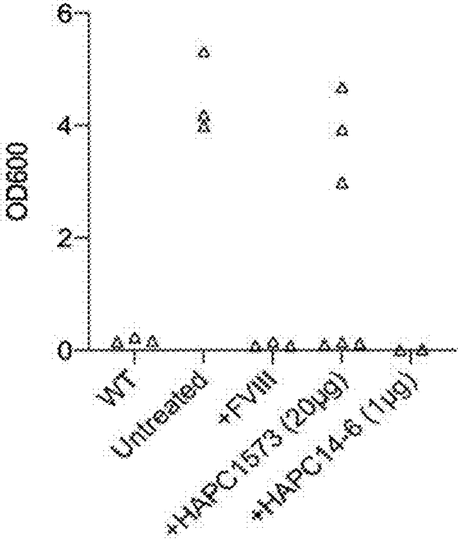
FIG. 7 shows in vivo pharmacodynamic experiments. A: effects of injecting coagulation factor FVIII, HAPC1573 and HAPC-14-6 into coagulation factor FVIII-deficient mice on coagulation function of the deficient mice; B: effects of injecting different doses of HAPC-14-6 into coagulation factor FVIII-deficient mice on coagulation function of the deficient mice; C: effects of injecting HAPC1573 and different doses of HAPC-14-6 into coagulation factor FIX-deficient mice on coagulation function of the deficient mice.

As shown in FIG. 7A, in the humanized protein C hemophilia A mice, 1 U/mouse coagulation factor FVIII, 20 μg/mouse murine antibody 1573 and 1 μg/mouse HAPC-14-6 were injected respectively. The coagulation function of the mice injected with the novel anti-aPC monoclonal antibody HAPC-14-6 was restored to the level of normal mice, which was the same as the effect of treatment of mice with coagulation factor FVIII.

Figure 7B:
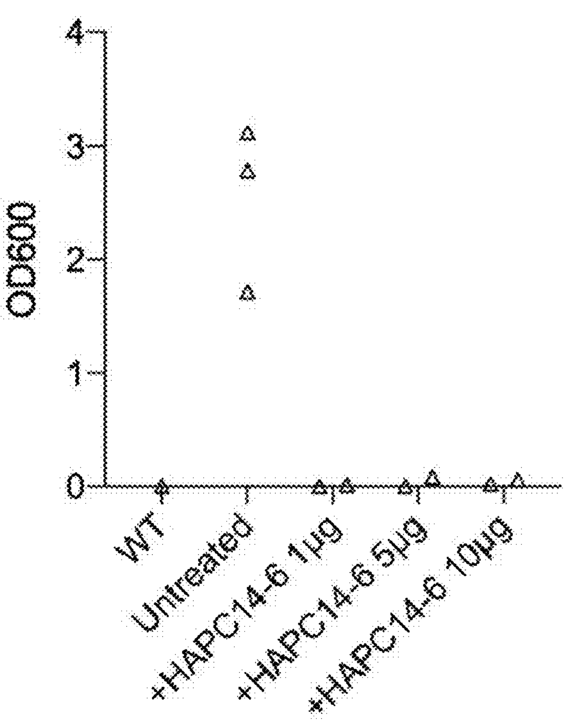

As shown in FIG. 7B, in the humanized protein C hemophilia A mice, after different doses of HAPC-14-6 were respectively injected, the coagulation function of the deficient mice could be restored to the normal level by at most 1 μg of HAPC-14-6.

Figure 7C:
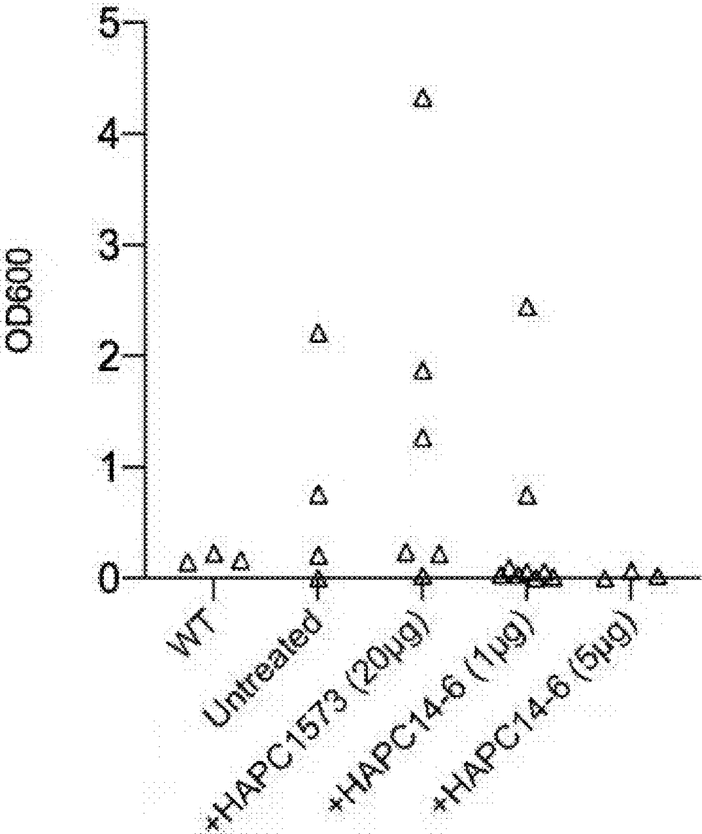

As shown in FIG. 7C, in the humanized protein C hemophilia B mice, after different doses of HAPC-14-6 were respectively injected, the coagulation function of the deficient mice could be restored to the normal level by at most 1 μg of HAPC-14-6.

The result indicated that in the present disclosure, after the protein C activating enzyme (protac)-induced APTT experiments were used to test the minimum dose of anti-aPC monoclonal antibodies to inhibit the anticoagulant activity of aPC in human plasma deficient in multiple coagulation factors, it was found that a concentration of at most 1 μg/mg of the anti-aPC monoclonal antibodies could completely inhibit the anticoagulant activity of aPC, while a concentration of 100 μg/ml or above was required for the murine antibody HAPC1573.

The foregoing embodiments are merely intended for describing the technical solutions of the present disclosure, but not for limiting the present disclosure. Although the present disclosure is described in detail with reference to the foregoing embodiments, persons of ordinary skill in the art should understand that they may still make modifications to the specific implementations described in the foregoing embodiments or make equivalent replacements to some technical features thereof. Changes and advantages that can be conceived by persons skilled in the art without departing from the spirit and scope of the concept of the disclosure, should fall in the scope of the technical solutions claimed in the present disclosure.

What is claimed is:

1. An anti-activated protein C (aPC) monoclonal antibody, wherein the anti-aPC monoclonal antibody is selected from one of the following:

an antibody comprising (a) heavy chain CDRs represented by SEQ ID NOs: 33, 34, and 35; and (b) light chain CDRs represented by SEQ ID NOs: 36, 37, and 38;

an antibody comprising (c) heavy chain CDRs represented by SEQ ID NOs: 39, 40, and 41; and (d) light chain CDRs represented by SEQ ID NOs: 42, 43, and 44;

an antibody comprising (e) heavy chain CDRs represented by SEQ ID NOs: 45, 46, and 47; and (f) light chain CDRs represented by SEQ ID NOs: 48, 49, and 50;

an antibody comprising (g) heavy chain CDRs represented by SEQ ID NOs: 51, 52, and 53; and (h) light chain CDRs represented by SEQ ID NOs: 54, 55, and 56;

an antibody comprising (i) heavy chain CDRs represented by SEQ ID NOs: 57, 58, and 59; and (i) light chain CDRs represented by SEQ ID NOs: 60, 61, and 62;

an antibody comprising (k) heavy chain CDRs represented by SEQ ID NOS: 63, 64, and 65; and (l) light chain CDRs represented by SEQ ID NOs: 66, 67, and 68;

an antibody comprising (m) heavy chain CDRs represented by SEQ ID NOs: 69, 70, and 71; and (n) light chain CDRs represented by SEQ ID NOs: 72, 73, and 74;

an antibody comprising (o) heavy chain CDRs represented by SEQ ID NOs: 75, 76, and 77; and (p) light chain CDRs represented by SEQ ID NOs: 78, 79, and 80;

an antibody comprising (q) heavy chain CDRs represented by SEQ ID NOs: 81, 82, and 83; and (r) light chain CDRs represented by SEQ ID NOs: 84, 85, and 86; and an antibody comprising (s) heavy chain CDRs represented by SEQ ID NOs: 87, 88, and 89; and (t) light chain CDRs represented by SEQ ID NOs: 90, 91, and 92.

2. The anti-aPC monoclonal antibody according to claim 1, wherein the anti-aPC monoclonal antibody is selected from the following:

an antibody comprising a heavy chain as shown in SEQ ID NO: 7 and a light chain as shown in SEQ ID NO: 8;

an antibody comprising a heavy chain as shown in SEQ ID NO: 9 and a light chain as shown in SEQ ID NO: 10;

an antibody comprising a heavy chain as shown in SEQ ID NO: 11 and a light chain as shown in SEQ ID NO: 12;

an antibody comprising a heavy chain as shown in SEQ ID NO: 13 and a light chain as shown in SEQ ID NO: 14;

an antibody comprising a heavy chain as shown in SEQ ID NO: 15 and a light chain as shown in SEQ ID NO: 16;

an antibody comprising a heavy chain as shown in SEQ ID NO: 17 and a light chain as shown in SEQ ID NO: 18;

an antibody comprising a heavy chain as shown in SEQ ID NO: 19 and a light chain as shown in SEQ ID NO: 20;

an antibody comprising a heavy chain as shown in SEQ ID NO: 21 and a light chain as shown in SEQ ID NO: 22;

an antibody comprising a heavy chain as shown in SEQ ID NO: 23 and a light chain as shown in SEQ ID NO: 24; and an antibody comprising a heavy chain as shown in SEQ ID NO: 25 and a light chain as shown in SEQ ID NO: 26.

3. The anti-aPC monoclonal antibody according to claim 1, wherein the anti-aPC monoclonal antibody is a complete antibody or an antibody fragment thereof; wherein the antibody fragment is Fab', Fab, F(ab')2, Fv or scFv.

4. A biological material related to the anti-aPC monoclonal antibody according to claim 1, wherein the biological material is any one of 1) to 3) as follows:

1) A nucleic acid molecule encoding the anti-aPC monoclonal antibody according to claim 1;

2) A construct containing the nucleic acid molecule as described in 1); and

3) An expression system containing the nucleic acid molecule as described in 1).

5. A preparation product, wherein the preparation product is a pharmaceutical composition or a detection kit;

the preparation product comprises the anti-aPC monoclonal antibody according to claim 1; and when being the pharmaceutical composition, the preparation product further comprises a pharmaceutically acceptable carrier.

6. A method for treating coagulation related disorders, comprising administering to an individual in need of treatment an effective amount of the anti-aPC monoclonal antibody according to claim 1; wherein the individual suffers from coagulation deficiency or defect disorders, or the individual is in need of blood coagulation treatment, or the individual suffers from sepsis or hemophilia, or the individual is in need of regulation of hemostasis.

7. The method according to claim 6, wherein the coagulation deficiency or defect disorders comprise disorders causing coagulopathy due to deficiency of coagulation factors and thus causing bleeding, and coagulation disturbances caused by trauma or surgery.

8. The method according to claim 7, wherein the coagulation deficiency or defect disorders comprise hemophilia, sepsis and traumatic hemorrhage.

9. A preparation product, wherein the preparation product is a pharmaceutical composition or a detection kit;

the preparation product comprises any one or more of the biological materials according to claim 4; and when being the pharmaceutical composition, the preparation product further comprises a pharmaceutically acceptable carrier.

10. A method for treating coagulation related disorders, comprising administering to an individual in need of treatment an effective amount of any one or more of the biological materials according to claim 4; wherein the individual suffers from coagulation deficiency or defect disorders, or the individual is in need of blood coagulation treatment, or the individual suffers from sepsis or hemophilia, or the individual is in need of regulation of hemostasis.

11. A method for promoting the ability of activated protein C (aPC) in an individual to cleave histones H3 and H4, comprising administering to the individual in need an effective amount of the anti-aPC monoclonal antibody of claim 1.

12. A method of inhibiting the anticoagulant activity of activated protein C (aPC) in an individual, comprising administering to the individual in need an effective amount of the anti-aPC monoclonal antibody of claim 1.

13. A kit for detecting activated protein C (aPC) in a sample, comprising the anti-aPC monoclonal antibody of claim 1.

* * * * *

SEQUENCE LISTING

```
<160> NUMBER OF SEQ ID NOS: 94

<210> SEQ ID NO 1
<211> LENGTH: 118
<212> TYPE: PRT
<213> ORGANISM: Artificial Sequence
<220> FEATURE:
<223> OTHER INFORMATION: Heavy chain of Humanized antibody 13 (HAPC-13)

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Leu Asn Trp Val Arg Gln Ala Pro Gly Lys Gly Leu Glu Trp Val
        35                  40                  45

Gly Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Ser Ile
65                  70                  75                  80

Thr Tyr Leu Gln Met Asn Ser Leu Arg Ala Glu Asp Thr Ala Val Tyr
                85                  90                  95

Tyr Cys Ala Arg Glu Gly Asp Tyr Phe Asp Tyr Trp Gly Gln Gly Thr
            100                 105                 110

Thr Val Thr Val Ser Ser
        115


<210> SEQ ID NO 2
<211> LENGTH: 111
<212> TYPE: PRT
```

```
<213> ORGANISM: Artificial Sequence
<220> FEATURE:
<223> OTHER INFORMATION: Light chain of Humanized antibody 13 (HAPC-13)

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Phe
            20                  25                  30

Gly Ala Thr Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys
            100                 105                 110


<210> SEQ ID NO 3
<211> LENGTH: 118
<212> TYPE: PRT
<213> ORGANISM: Artificial Sequence
<220> FEATURE:
<223> OTHER INFORMATION: Heavy chain of Humanized antibody 16 (HAPC-16)

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Leu Asn Trp Val Arg Gln Ala Pro Gly Lys Gly Leu Glu Trp Val
        35                  40                  45

Gly Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Ser Ile
65                  70                  75                  80

Thr Tyr Leu Gln Met Asn Ser Leu Arg Ala Glu Asp Thr Ala Val Tyr
                85                  90                  95

Tyr Cys Ala Arg Glu Gly Asp Tyr Phe Asp Tyr Trp Gly Gln Gly Thr
            100                 105                 110

Thr Val Thr Val Ser Ser
        115


<210> SEQ ID NO 4
<211> LENGTH: 111
<212> TYPE: PRT
<213> ORGANISM: Artificial Sequence
<220> FEATURE:
<223> OTHER INFORMATION: Light chain of Humanized antibody 16 (HAPC-16)

<400> SEQUENCE: 4

Asn Ile Val Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Phe
            20                  25                  30

Gly Ala Thr Phe Met His Trp Tyr Gln Gln Lys Pro Gly Lys Pro Pro
        35                  40                  45
```

```
Lys Leu Leu Ile Tyr Leu Ala Ser Asn Leu Glu Ser Gly Val Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys
            100                 105                 110


<210> SEQ ID NO 5
<211> LENGTH: 118
<212> TYPE: PRT
<213> ORGANISM: Artificial Sequence
<220> FEATURE:
<223> OTHER INFORMATION: Heavy chain of Humanized antibody 14 (HAPC-14)

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Leu Asn Trp Val Arg Gln Ala Pro Gly Lys Gly Leu Glu Trp Val
        35                  40                  45

Gly Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Ser Ile
65                  70                  75                  80

Thr Tyr Leu Gln Met Asn Ser Leu Arg Ala Glu Asp Thr Ala Val Tyr
                85                  90                  95

Tyr Cys Ala Arg Glu Gly Asp Tyr Phe Asp Tyr Trp Gly Gln Gly Thr
            100                 105                 110

Thr Val Thr Val Ser Ser
        115


<210> SEQ ID NO 6
<211> LENGTH: 111
<212> TYPE: PRT
<213> ORGANISM: Artificial Sequence
<220> FEATURE:
<223> OTHER INFORMATION: Light chain of Humanized antibody 14 (HAPC-14)

<400> SEQUENCE: 6

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Phe
            20                  25                  30

Gly Ala Thr Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys
            100                 105                 110
```

```
<210> SEQ ID NO 7
<211> LENGTH: 118
<212> TYPE: PRT
<213> ORGANISM: Artificial Sequence
<220> FEATURE:
<223> OTHER INFORMATION: Heavy chain of HAPC-14-1

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Tyr Leu Asn Trp Val Arg Gln Ala Pro Gly Lys Gly Leu Glu Trp Val
        35                  40                  45

Gly Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Ser Ile
65                  70                  75                  80

Thr Tyr Leu Gln Met Asn Ser Leu Arg Ala Glu Asp Thr Ala Val Tyr
                85                  90                  95

Tyr Cys Ala Arg Glu Gly Asp Tyr Phe Asp Tyr Trp Gly Gln Gly Thr
            100                 105                 110

Thr Val Thr Val Ser Ser
        115


<210> SEQ ID NO 8
<211> LENGTH: 111
<212> TYPE: PRT
<213> ORGANISM: Artificial Sequence
<220> FEATURE:
<223> OTHER INFORMATION: Light chain of HAPC-14-1

<400> SEQUENCE: 8

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Phe
            20                  25                  30

Gly Ala Thr Phe Met His Trp Tyr Gln Gln Lys Pro Gly Lys Ala Pro
        35                  40                  45

Lys Leu Leu Ile Tyr Leu Ala Ser Trp Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys
            100                 105                 110


<210> SEQ ID NO 9
<211> LENGTH: 118
<212> TYPE: PRT
<213> ORGANISM: Artificial Sequence
<220> FEATURE:
<223> OTHER INFORMATION: Heavy chain of HAPC-14-2

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30
```

```
Tyr Leu Asn Trp Val Arg Gln Ala Pro Gly Lys Gly Leu Glu Trp Val
        35                  40                  45

Gly Asp Ile Arg Leu Lys Lys Asn Asn Tyr Glu Lys His Tyr Ala Glu
    50                  55                  60

Ser Val Lys Gly Arg Phe Thr Ile Ser Arg Asp Asp Ser Lys Ser Ile
65                  70                  75                  80

Thr Tyr Leu Gln Met Asn Ser Leu Arg Ala Glu Asp Thr Ala Val Tyr
                85                  90                  95

Tyr Cys Ala Arg Glu Gly Asp Tyr Phe Asp Tyr Trp Gly Gln Gly Thr
            100                 105                 110

Thr Val Thr Val Ser Ser
        115


<210> SEQ ID NO 10
<211> LENGTH: 111
<212> TYPE: PRT
<213> ORGANISM: Artificial Sequence
<220> FEATURE:
<223> OTHER INFORMATION: Light chain of HAPC-14-2

<400> SEQUENCE: 10

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Phe
            20                  25                  30

Gly Ala Thr Phe Met His Trp Tyr Gln Gln Lys Pro Gly Lys Ala Pro
        35                  40                  45

Lys Leu Leu Ile Tyr Leu Ala Ser Trp Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Val Gln Asn Asn
                85                  90                  95

Glu Asp Pro Tyr Thr Phe Gly Gln Gly Thr Lys Leu Glu Ile Lys
            100                 105                 110


<210> SEQ ID NO 11
<211> LENGTH: 118
<212> TYPE: PRT
<213> ORGANISM: Artificial Sequence
<220> FEATURE:
<223> OTHER INFORMATION: Heavy chain of HAPC-14-3

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Tyr Leu Asn Trp Val Arg Gln Ala Pro Gly Lys Gly Leu Glu Trp Val
        35                  40                  45

Gly Asp Ile Arg Leu Lys Lys Asn Asn Tyr Glu Lys His Tyr Ala Glu
    50                  55                  60

Ser Val Lys Gly Arg Phe Thr Ile Ser Arg Asp Asp Ser Lys Ser Ile
65                  70                  75                  80

Thr Tyr Leu Gln Met Asn Ser Leu Arg Ala Glu Asp Thr Ala Val Tyr
                85                  90                  95

Tyr Cys Ala Arg Glu Gly Asp Tyr Phe Asp Tyr Trp Gly Gln Gly Thr
```

```
            100                 105                 110

Thr Val Thr Val Ser Ser
        115


<210> SEQ ID NO 12
<211> LENGTH: 111
<212> TYPE: PRT
<213> ORGANISM: Artificial Sequence
<220> FEATURE:
<223> OTHER INFORMATION: Light chain of HAPC-14-3

<400> SEQUENCE: 12

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Phe
            20                  25                  30

Gly Ala Thr Phe Met His Trp Tyr Gln Gln Lys Pro Gly Lys Ala Pro
        35                  40                  45

Lys Leu Leu Ile Tyr Leu Ala Ser Arg Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Val Gln Asn Asn
                85                  90                  95

Glu Asp Pro Tyr Thr Phe Gly Gln Gly Thr Lys Leu Glu Ile Lys
            100                 105                 110


<210> SEQ ID NO 13
<211> LENGTH: 118
<212> TYPE: PRT
<213> ORGANISM: Artificial Sequence
<220> FEATURE:
<223> OTHER INFORMATION: Heavy chain of HAPC-14-4

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Tyr Leu Asn Trp Val Arg Gln Ala Pro Gly Lys Gly Leu Glu Trp Val
        35                  40                  45

Gly Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Ser Ile
65                  70                  75                  80

Thr Tyr Leu Gln Met Asn Ser Leu Arg Ala Glu Asp Thr Ala Val Tyr
                85                  90                  95

Tyr Cys Ala Arg Glu Gly Asp Tyr Phe Asp Tyr Trp Gly Gln Gly Thr
            100                 105                 110

Thr Val Thr Val Ser Ser
        115


<210> SEQ ID NO 14
<211> LENGTH: 111
<212> TYPE: PRT
<213> ORGANISM: Artificial Sequence
<220> FEATURE:
<223> OTHER INFORMATION: Light chain of HAPC-14-4

<400> SEQUENCE: 14
```

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Phe
            20                  25                  30

Gly Ala Thr Phe Met His Trp Tyr Gln Gln Lys Pro Gly Lys Ala Pro
        35                  40                  45

Lys Leu Leu Ile Tyr Leu Ala Ser Arg Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Val Gln Asn Asn
                85                  90                  95

Glu Asp Pro Tyr Thr Phe Gly Gln Gly Thr Lys Leu Glu Ile Lys
            100                 105                 110


<210> SEQ ID NO 15
<211> LENGTH: 118
<212> TYPE: PRT
<213> ORGANISM: Artificial Sequence
<220> FEATURE:
<223> OTHER INFORMATION: Heavy chain of HAPC-14-5

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Tyr Leu Asn Trp Val Arg Gln Ala Pro Gly Lys Gly Leu Glu Trp Val
        35                  40                  45

Gly Asp Ile Arg Leu Lys Lys Asn Asn Tyr Glu Lys His Tyr Ala Glu
    50                  55                  60

Ser Val Lys Gly Arg Phe Thr Ile Ser Arg Asp Asp Ser Lys Ser Ile
65                  70                  75                  80

Thr Tyr Leu Gln Met Asn Ser Leu Arg Ala Glu Asp Thr Ala Val Tyr
                85                  90                  95

Tyr Cys Ala Arg Glu Gly Asp Tyr Phe Asp Tyr Trp Gly Gln Gly Thr
            100                 105                 110

Thr Val Thr Val Ser Ser
        115


<210> SEQ ID NO 16
<211> LENGTH: 111
<212> TYPE: PRT
<213> ORGANISM: Artificial Sequence
<220> FEATURE:
<223> OTHER INFORMATION: Light chain of HAPC-14-5

<400> SEQUENCE: 16

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Phe
            20                  25                  30

Gly Ala Thr Phe Met His Trp Tyr Gln Gln Lys Pro Gly Lys Ala Pro
        35                  40                  45

Lys Leu Leu Ile Tyr Leu Ala Ser Trp Leu Gly Ser Gly Val Pro Ser
    50                  55                  60

Arg Phe Ser Gly Ser Gly Ser Gly Thr Asp Phe Thr Leu Thr Ile Ser
```

```
65                  70                  75                  80

Ser Leu Gln Pro Glu Asp Phe Ala Thr Tyr Tyr Cys Val Gln Asn Asn
                85                  90                  95

Glu Asp Pro Tyr Thr Phe Gly Gln Gly Thr Lys Leu Glu Ile Lys
            100                 105                 110


<210> SEQ ID NO 17
<211> LENGTH: 118
<212> TYPE: PRT
<213> ORGANISM: Artificial Sequence
<220> FEATURE:
<223> OTHER INFORMATION: Heavy chain of HAPC-14-6

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Tyr Leu Asn Trp Val Arg Gln Ala Pro Gly Lys Gly Leu Glu Trp Val
        35                  40                  45

Gly Asp Ile Arg Leu Lys Lys Asn Asn Tyr Glu Lys His Tyr Ala Glu
    50                  55                  60

Ser Val Lys Gly Arg Phe Thr Ile Ser Arg Asp Asp Ser Lys Ser Ile
65                  70                  75                  80

Thr Tyr Leu Gln Met Asn Ser Leu Arg Ala Glu Asp Thr Ala Val Tyr
                85                  90                  95

Tyr Cys Ala Arg Glu Gly Asp Tyr Phe Asp Tyr Trp Gly Gln Gly Thr
            100                 105                 110

Thr Val Thr Val Ser Ser
        115


<210> SEQ ID NO 18
<211> LENGTH: 111
<212> TYPE: PRT
<213> ORGANISM: Artificial Sequence
<220> FEATURE:
<223> OTHER INFORMATION: Light chain of HAPC-14-6

<400> SEQUENCE: 18

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Phe
            20                  25                  30

Gly Ala Thr Phe Met His Trp Tyr Gln Gln Lys Pro Gly Lys Ala Pro
        35                  40                  45

Lys Leu Leu Ile Tyr Leu Ala Ser Arg Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys
            100                 105                 110


<210> SEQ ID NO 19
<211> LENGTH: 118
<212> TYPE: PRT
<213> ORGANISM: Artificial Sequence
<220> FEATURE:
```

<223> OTHER INFORMATION: Heavy chain of HAPC-14-7

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Tyr Leu Asn Trp Val Arg Gln Ala Pro Gly Lys Gly Leu Glu Trp Val
        35                  40                  45

Gly Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Ser Ile
65                  70                  75                  80

Thr Tyr Leu Gln Met Asn Ser Leu Arg Ala Glu Asp Thr Ala Val Tyr
                85                  90                  95

Tyr Cys Ala Arg Glu Gly Asp Tyr Phe Asp Tyr Trp Gly Gln Gly Thr
            100                 105                 110

Thr Val Thr Val Ser Ser
        115
```

<210> SEQ ID NO 20
<211> LENGTH: 111
<212> TYPE: PRT
<213> ORGANISM: Artificial Sequence
<220> FEATURE:
<223> OTHER INFORMATION: Light chain of HAPC-14-7

<400> SEQUENCE: 20

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Phe
            20                  25                  30

Gly Ala Thr Phe Met His Trp Tyr Gln Gln Lys Pro Gly Lys Ala Pro
        35                  40                  45

Lys Leu Leu Ile Tyr Leu Ala Ser Arg Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys
            100                 105                 110
```

<210> SEQ ID NO 21
<211> LENGTH: 118
<212> TYPE: PRT
<213> ORGANISM: Artificial Sequence
<220> FEATURE:
<223> OTHER INFORMATION: Heavy chain of HAPC-14-8

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Tyr Leu Asn Trp Val Arg Gln Ala Pro Gly Lys Gly Leu Glu Trp Val
        35                  40                  45

Gly Asp Ile Arg Leu Lys Lys Asn Asn Tyr Glu Lys His Tyr Ala Glu
```

```
    50                  55                  60

Ser Val Lys Gly Arg Phe Thr Ile Ser Arg Asp Asp Ser Lys Ser Ile
65                  70                  75                  80

Thr Tyr Leu Gln Met Asn Ser Leu Arg Ala Glu Asp Thr Ala Val Tyr
                85                  90                  95

Tyr Cys Ala Arg Glu Gly Asp Thr Phe Asp Tyr Trp Gly Gln Gly Thr
            100                 105                 110

Thr Val Thr Val Ser Ser
        115


<210> SEQ ID NO 22
<211> LENGTH: 111
<212> TYPE: PRT
<213> ORGANISM: Artificial Sequence
<220> FEATURE:
<223> OTHER INFORMATION: Light chain of HAPC-14-8

<400> SEQUENCE: 22

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Phe
            20                  25                  30

Gly Ala Thr Phe Met His Trp Tyr Gln Gln Lys Pro Gly Lys Ala Pro
        35                  40                  45

Lys Leu Leu Ile Tyr Leu Ala Ser Arg Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Val Gln Asn Asn
                85                  90                  95

Glu Asp Pro Tyr Thr Phe Gly Gln Gly Thr Lys Leu Glu Ile Lys
            100                 105                 110


<210> SEQ ID NO 23
<211> LENGTH: 118
<212> TYPE: PRT
<213> ORGANISM: Artificial Sequence
<220> FEATURE:
<223> OTHER INFORMATION: Heavy chain of HAPC-14-9

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Tyr Leu Asn Trp Val Arg Gln Ala Pro Gly Lys Gly Leu Glu Trp Val
        35                  40                  45

Gly Asp Ile Arg Leu Lys Lys Asn Asn Tyr Glu Lys His Tyr Ala Glu
    50                  55                  60

Ser Val Lys Gly Arg Phe Thr Ile Ser Arg Asp Asp Ser Lys Ser Ile
65                  70                  75                  80

Thr Tyr Leu Gln Met Asn Ser Leu Arg Ala Glu Asp Thr Ala Val Tyr
                85                  90                  95

Tyr Cys Ala Arg Glu Gly Asp Thr Phe Asp Tyr Trp Gly Gln Gly Thr
            100                 105                 110

Thr Val Thr Val Ser Ser
        115
```

<210> SEQ ID NO 24
<211> LENGTH: 111
<212> TYPE: PRT
<213> ORGANISM: Artificial Sequence
<220> FEATURE:
<223> OTHER INFORMATION: Light chain of HAPC-14-9

<400> SEQUENCE: 24

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Phe
            20                  25                  30

Gly Ala Thr Phe Met His Trp Tyr Gln Gln Lys Pro Gly Lys Ala Pro
        35                  40                  45

Lys Leu Leu Ile Tyr Leu Ala Ser Arg Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys
            100                 105                 110
```

<210> SEQ ID NO 25
<211> LENGTH: 118
<212> TYPE: PRT
<213> ORGANISM: Artificial Sequence
<220> FEATURE:
<223> OTHER INFORMATION: Heavy chain of HAPC-14-10

<400> SEQUENCE: 25

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Leu Asn Trp Val Arg Gln Ala Pro Gly Lys Gly Leu Glu Trp Val
        35                  40                  45

Gly Asp Ile Arg Leu Lys Lys Asn Asn Tyr Glu Lys His Tyr Ala Glu
    50                  55                  60

Ser Val Lys Gly Arg Phe Thr Ile Ser Arg Asp Asp Ser Lys Ser Ile
65                  70                  75                  80

Thr Tyr Leu Gln Met Asn Ser Leu Arg Ala Glu Asp Thr Ala Val Tyr
                85                  90                  95

Tyr Cys Ala Arg Glu Gly Asp Thr Phe Asp Tyr Trp Gly Gln Gly Thr
            100                 105                 110

Thr Val Thr Val Ser Ser
        115
```

<210> SEQ ID NO 26
<211> LENGTH: 111
<212> TYPE: PRT
<213> ORGANISM: Artificial Sequence
<220> FEATURE:
<223> OTHER INFORMATION: Light chain of HAPC-14-10

<400> SEQUENCE: 26

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Phe
```

```
            20                  25                  30

Gly Ala Thr Phe Met His Trp Tyr Gln Gln Lys Pro Gly Lys Ala Pro
        35                  40                  45

Lys Leu Leu Ile Tyr Leu Ala Ser Arg Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Val Gln Asn Asn
                85                  90                  95

Glu Asp Pro Tyr Thr Phe Gly Gln Gly Thr Lys Leu Glu Ile Lys
            100                 105                 110


<210> SEQ ID NO 27
<211> LENGTH: 5
<212> TYPE: PRT
<213> ORGANISM: Artificial Sequence
<220> FEATURE:
<223> OTHER INFORMATION: HAPC-14 Heavy chain CDR1

<400> SEQUENCE: 27

Asn Tyr Tyr Leu Asn
1               5


<210> SEQ ID NO 28
<211> LENGTH: 19
<212> TYPE: PRT
<213> ORGANISM: Artificial Sequence
<220> FEATURE:
<223> OTHER INFORMATION: HAPC-14 Heavy chain CDR2

<400> SEQUENCE: 28

Asp Ile Arg Leu Lys Ser Asn Asn Tyr Glu Lys His Tyr Ala Glu Ser
1               5                   10                  15

Val Lys Gly


<210> SEQ ID NO 29
<211> LENGTH: 7
<212> TYPE: PRT
<213> ORGANISM: Artificial Sequence
<220> FEATURE:
<223> OTHER INFORMATION: HAPC-14 Heavy chain CDR3

<400> SEQUENCE: 29

Glu Gly Asp Tyr Phe Asp Tyr
1               5


<210> SEQ ID NO 30
<211> LENGTH: 15
<212> TYPE: PRT
<213> ORGANISM: Artificial Sequence
<220> FEATURE:
<223> OTHER INFORMATION: HAPC-14 Light chain CDR1

<400> SEQUENCE: 30

Arg Ala Ser Glu Ser Val Asp Ser Phe Gly Ala Thr Phe Met His
1               5                   10                  15


<210> SEQ ID NO 31
<211> LENGTH: 7
<212> TYPE: PRT
<213> ORGANISM: Artificial Sequence
<220> FEATURE:
<223> OTHER INFORMATION: HAPC-14 Light chain CDR2
```

<400> SEQUENCE: 31

Leu Ala Ser Asn Leu Glu Ser
1 5

<210> SEQ ID NO 32
<211> LENGTH: 9
<212> TYPE: PRT
<213> ORGANISM: Artificial Sequence
<220> FEATURE:
<223> OTHER INFORMATION: HAPC-14 Light chain CDR3

<400> SEQUENCE: 32

Gln Gln Asn Asn Glu Asp Pro Tyr Thr
1 5

<210> SEQ ID NO 33
<211> LENGTH: 5
<212> TYPE: PRT
<213> ORGANISM: Artificial Sequence
<220> FEATURE:
<223> OTHER INFORMATION: HAPC-14-1 Heavy chain CDR1

<400> SEQUENCE: 33

Phe Tyr Tyr Leu Asn
1 5

<210> SEQ ID NO 34
<211> LENGTH: 19
<212> TYPE: PRT
<213> ORGANISM: Artificial Sequence
<220> FEATURE:
<223> OTHER INFORMATION: HAPC-14-1 Heavy chain CDR2

<400> SEQUENCE: 34

Asp Ile Arg Leu Lys Ser Asn Asn Tyr Glu Lys His Tyr Ala Glu Ser
1 5 10 15

Val Lys Gly

<210> SEQ ID NO 35
<211> LENGTH: 7
<212> TYPE: PRT
<213> ORGANISM: Artificial Sequence
<220> FEATURE:
<223> OTHER INFORMATION: HAPC-14-1 Heavy chain CDR3

<400> SEQUENCE: 35

Glu Gly Asp Tyr Phe Asp Tyr
1 5

<210> SEQ ID NO 36
<211> LENGTH: 15
<212> TYPE: PRT
<213> ORGANISM: Artificial Sequence
<220> FEATURE:
<223> OTHER INFORMATION: HAPC-14-1 Light chain CDR1

<400> SEQUENCE: 36

Arg Ala Ser Glu Ser Val Asp Ser Phe Gly Ala Thr Phe Met His
1 5 10 15

<210> SEQ ID NO 37
<211> LENGTH: 7
<212> TYPE: PRT
<213> ORGANISM: Artificial Sequence
<220> FEATURE:
<223> OTHER INFORMATION: HAPC-14-1 Light chain CDR2

<400> SEQUENCE: 37

Leu Ala Ser Trp Leu Gly Ser
1 5

<210> SEQ ID NO 38
<211> LENGTH: 9
<212> TYPE: PRT
<213> ORGANISM: Artificial Sequence
<220> FEATURE:
<223> OTHER INFORMATION: HAPC-14-1 Light chain CDR3

<400> SEQUENCE: 38

Gln Gln Asn Asn Glu Asp Pro Tyr Thr
1 5

<210> SEQ ID NO 39
<211> LENGTH: 5
<212> TYPE: PRT
<213> ORGANISM: Artificial Sequence
<220> FEATURE:
<223> OTHER INFORMATION: HAPC-14-2 Heavy chain CDR1

<400> SEQUENCE: 39

Phe Tyr Tyr Leu Asn
1 5

<210> SEQ ID NO 40
<211> LENGTH: 19
<212> TYPE: PRT
<213> ORGANISM: Artificial Sequence
<220> FEATURE:
<223> OTHER INFORMATION: HAPC-14-2 Heavy chain CDR2

<400> SEQUENCE: 40

Asp Ile Arg Leu Lys Lys Asn Asn Tyr Glu Lys His Tyr Ala Glu Ser
1 5 10 15

Val Lys Gly

<210> SEQ ID NO 41
<211> LENGTH: 7
<212> TYPE: PRT
<213> ORGANISM: Artificial Sequence
<220> FEATURE:
<223> OTHER INFORMATION: HAPC-14-2 Heavy chain CDR3

<400> SEQUENCE: 41

Glu Gly Asp Tyr Phe Asp Tyr
1 5

<210> SEQ ID NO 42
<211> LENGTH: 15
<212> TYPE: PRT
<213> ORGANISM: Artificial Sequence
<220> FEATURE:
<223> OTHER INFORMATION: HAPC-14-2 Light chain CDR1

<400> SEQUENCE: 42

Arg Ala Ser Glu Ser Val Asp Ser Phe Gly Ala Thr Phe Met His
1 5 10 15

<210> SEQ ID NO 43
<211> LENGTH: 7
<212> TYPE: PRT
<213> ORGANISM: Artificial Sequence
<220> FEATURE:

<223> OTHER INFORMATION: HAPC-14-2 Light chain CDR2

<400> SEQUENCE: 43

Leu Ala Ser Trp Leu Glu Ser
1 5

<210> SEQ ID NO 44
<211> LENGTH: 9
<212> TYPE: PRT
<213> ORGANISM: Artificial Sequence
<220> FEATURE:
<223> OTHER INFORMATION: HAPC-14-2 Light chain CDR3

<400> SEQUENCE: 44

Val Gln Asn Asn Glu Asp Pro Tyr Thr
1 5

<210> SEQ ID NO 45
<211> LENGTH: 5
<212> TYPE: PRT
<213> ORGANISM: Artificial Sequence
<220> FEATURE:
<223> OTHER INFORMATION: HAPC-14-3 Heavy chain CDR1

<400> SEQUENCE: 45

Phe Tyr Tyr Leu Asn
1 5

<210> SEQ ID NO 46
<211> LENGTH: 19
<212> TYPE: PRT
<213> ORGANISM: Artificial Sequence
<220> FEATURE:
<223> OTHER INFORMATION: HAPC-14-3 Heavy chain CDR2

<400> SEQUENCE: 46

Asp Ile Arg Leu Lys Lys Asn Asn Tyr Glu Lys His Tyr Ala Glu Ser
1 5 10 15

Val Lys Gly

<210> SEQ ID NO 47
<211> LENGTH: 7
<212> TYPE: PRT
<213> ORGANISM: Artificial Sequence
<220> FEATURE:
<223> OTHER INFORMATION: HAPC-14-3 Heavy chain CDR3

<400> SEQUENCE: 47

Glu Gly Asp Tyr Phe Asp Tyr
1 5

<210> SEQ ID NO 48
<211> LENGTH: 15
<212> TYPE: PRT
<213> ORGANISM: Artificial Sequence
<220> FEATURE:
<223> OTHER INFORMATION: HAPC-14-3 Light chain CDR1

<400> SEQUENCE: 48

Arg Ala Ser Glu Ser Val Asp Ser Phe Gly Ala Thr Phe Met His
1 5 10 15

<210> SEQ ID NO 49
<211> LENGTH: 7
<212> TYPE: PRT
<213> ORGANISM: Artificial Sequence
<220> FEATURE:
<223> OTHER INFORMATION: HAPC-14-3 Light chain CDR2

<400> SEQUENCE: 49

Leu Ala Ser Arg Leu Gly Ser
1 5

<210> SEQ ID NO 50
<211> LENGTH: 9
<212> TYPE: PRT
<213> ORGANISM: Artificial Sequence
<220> FEATURE:
<223> OTHER INFORMATION: HAPC-14-3 Light chain CDR3

<400> SEQUENCE: 50

Val Gln Asn Asn Glu Asp Pro Tyr Thr
1 5

<210> SEQ ID NO 51
<211> LENGTH: 5
<212> TYPE: PRT
<213> ORGANISM: Artificial Sequence
<220> FEATURE:
<223> OTHER INFORMATION: HAPC-14-4 Heavy chain CDR1

<400> SEQUENCE: 51

Phe Tyr Tyr Leu Asn
1 5

<210> SEQ ID NO 52
<211> LENGTH: 19
<212> TYPE: PRT
<213> ORGANISM: Artificial Sequence
<220> FEATURE:
<223> OTHER INFORMATION: HAPC-14-4 Heavy chain CDR2

<400> SEQUENCE: 52

Asp Ile Arg Leu Lys Ser Asn Asn Tyr Glu Lys His Tyr Ala Glu Ser
1 5 10 15

Val Lys Gly

<210> SEQ ID NO 53
<211> LENGTH: 7
<212> TYPE: PRT
<213> ORGANISM: Artificial Sequence
<220> FEATURE:
<223> OTHER INFORMATION: HAPC-14-4 Heavy chain CDR3

<400> SEQUENCE: 53

Glu Gly Asp Tyr Phe Asp Tyr
1 5

<210> SEQ ID NO 54
<211> LENGTH: 15
<212> TYPE: PRT
<213> ORGANISM: Artificial Sequence
<220> FEATURE:
<223> OTHER INFORMATION: HAPC-14-4 Light chain CDR1

<400> SEQUENCE: 54

Arg Ala Ser Glu Ser Val Asp Ser Phe Gly Ala Thr Phe Met His
1 5 10 15

<210> SEQ ID NO 55
<211> LENGTH: 7
<212> TYPE: PRT

<213> ORGANISM: Artificial Sequence
<220> FEATURE:
<223> OTHER INFORMATION: HAPC-14-4 Light chain CDR2

<400> SEQUENCE: 55

Leu Ala Ser Arg Leu Gly Ser
1 5

<210> SEQ ID NO 56
<211> LENGTH: 9
<212> TYPE: PRT
<213> ORGANISM: Artificial Sequence
<220> FEATURE:
<223> OTHER INFORMATION: HAPC-14-4 Light chain CDR3

<400> SEQUENCE: 56

Val Gln Asn Asn Glu Asp Pro Tyr Thr
1 5

<210> SEQ ID NO 57
<211> LENGTH: 5
<212> TYPE: PRT
<213> ORGANISM: Artificial Sequence
<220> FEATURE:
<223> OTHER INFORMATION: HAPC-14-5 Heavy chain CDR1

<400> SEQUENCE: 57

Phe Tyr Tyr Leu Asn
1 5

<210> SEQ ID NO 58
<211> LENGTH: 19
<212> TYPE: PRT
<213> ORGANISM: Artificial Sequence
<220> FEATURE:
<223> OTHER INFORMATION: HAPC-14-5 Heavy chain CDR2

<400> SEQUENCE: 58

Asp Ile Arg Leu Lys Lys Asn Asn Tyr Glu Lys His Tyr Ala Glu Ser
1 5 10 15

Val Lys Gly

<210> SEQ ID NO 59
<211> LENGTH: 7
<212> TYPE: PRT
<213> ORGANISM: Artificial Sequence
<220> FEATURE:
<223> OTHER INFORMATION: HAPC-14-5 Heavy chain CDR3

<400> SEQUENCE: 59

Glu Gly Asp Tyr Phe Asp Tyr
1 5

<210> SEQ ID NO 60
<211> LENGTH: 15
<212> TYPE: PRT
<213> ORGANISM: Artificial Sequence
<220> FEATURE:
<223> OTHER INFORMATION: HAPC-14-5 Light chain CDR1

<400> SEQUENCE: 60

Arg Ala Ser Glu Ser Val Asp Ser Phe Gly Ala Thr Phe Met His
1 5 10 15

<210> SEQ ID NO 61
<211> LENGTH: 7

<212> TYPE: PRT
<213> ORGANISM: Artificial Sequence
<220> FEATURE:
<223> OTHER INFORMATION: HAPC-14-5 Light chain CDR2

<400> SEQUENCE: 61

Leu Ala Ser Trp Leu Gly Ser
1               5

<210> SEQ ID NO 62
<211> LENGTH: 9
<212> TYPE: PRT
<213> ORGANISM: Artificial Sequence
<220> FEATURE:
<223> OTHER INFORMATION: HAPC-14-5 Light chain CDR3

<400> SEQUENCE: 62

Val Gln Asn Asn Glu Asp Pro Tyr Thr
1               5

<210> SEQ ID NO 63
<211> LENGTH: 5
<212> TYPE: PRT
<213> ORGANISM: Artificial Sequence
<220> FEATURE:
<223> OTHER INFORMATION: HAPC-14-6 Heavy chain CDR1

<400> SEQUENCE: 63

Phe Tyr Tyr Leu Asn
1               5

<210> SEQ ID NO 64
<211> LENGTH: 19
<212> TYPE: PRT
<213> ORGANISM: Artificial Sequence
<220> FEATURE:
<223> OTHER INFORMATION: HAPC-14-6 Heavy chain CDR2

<400> SEQUENCE: 64

Asp Ile Arg Leu Lys Lys Asn Asn Tyr Glu Lys His Tyr Ala Glu Ser
1               5                   10                  15

Val Lys Gly

<210> SEQ ID NO 65
<211> LENGTH: 7
<212> TYPE: PRT
<213> ORGANISM: Artificial Sequence
<220> FEATURE:
<223> OTHER INFORMATION: HAPC-14-6 Heavy chain CDR3

<400> SEQUENCE: 65

Glu Gly Asp Tyr Phe Asp Tyr
1               5

<210> SEQ ID NO 66
<211> LENGTH: 15
<212> TYPE: PRT
<213> ORGANISM: Artificial Sequence
<220> FEATURE:
<223> OTHER INFORMATION: HAPC-14-6 Light chain CDR1

<400> SEQUENCE: 66

Arg Ala Ser Glu Ser Val Asp Ser Phe Gly Ala Thr Phe Met His
1               5                   10                  15

<210> SEQ ID NO 67

<211> LENGTH: 7
<212> TYPE: PRT
<213> ORGANISM: Artificial Sequence
<220> FEATURE:
<223> OTHER INFORMATION: HAPC-14-6 Light chain CDR2

<400> SEQUENCE: 67

Leu Ala Ser Arg Leu Gly Ser
1 5

<210> SEQ ID NO 68
<211> LENGTH: 9
<212> TYPE: PRT
<213> ORGANISM: Artificial Sequence
<220> FEATURE:
<223> OTHER INFORMATION: HAPC-14-6 Light chain CDR3

<400> SEQUENCE: 68

Gln Gln Asn Asn Glu Asp Pro Tyr Thr
1 5

<210> SEQ ID NO 69
<211> LENGTH: 5
<212> TYPE: PRT
<213> ORGANISM: Artificial Sequence
<220> FEATURE:
<223> OTHER INFORMATION: HAPC-14-7 Heavy chain CDR1

<400> SEQUENCE: 69

Phe Tyr Tyr Leu Asn
1 5

<210> SEQ ID NO 70
<211> LENGTH: 19
<212> TYPE: PRT
<213> ORGANISM: Artificial Sequence
<220> FEATURE:
<223> OTHER INFORMATION: HAPC-14-7 Heavy chain CDR2

<400> SEQUENCE: 70

Asp Ile Arg Leu Lys Ser Asn Asn Tyr Glu Lys His Tyr Ala Glu Ser
1 5 10 15

Val Lys Gly

<210> SEQ ID NO 71
<211> LENGTH: 7
<212> TYPE: PRT
<213> ORGANISM: Artificial Sequence
<220> FEATURE:
<223> OTHER INFORMATION: HAPC-14-7 Heavy chain CDR3

<400> SEQUENCE: 71

Glu Gly Asp Tyr Phe Asp Tyr
1 5

<210> SEQ ID NO 72
<211> LENGTH: 15
<212> TYPE: PRT
<213> ORGANISM: Artificial Sequence
<220> FEATURE:
<223> OTHER INFORMATION: HAPC-14-7 Light chain CDR1

<400> SEQUENCE: 72

Arg Ala Ser Glu Ser Val Asp Ser Phe Gly Ala Thr Phe Met His
1 5 10 15

<210> SEQ ID NO 73
<211> LENGTH: 7
<212> TYPE: PRT
<213> ORGANISM: Artificial Sequence
<220> FEATURE:
<223> OTHER INFORMATION: HAPC-14-7 Light chain CDR2

<400> SEQUENCE: 73

Leu Ala Ser Arg Leu Glu Ser
1 5

<210> SEQ ID NO 74
<211> LENGTH: 9
<212> TYPE: PRT
<213> ORGANISM: Artificial Sequence
<220> FEATURE:
<223> OTHER INFORMATION: HAPC-14-7 Light chain CDR3

<400> SEQUENCE: 74

Gln Gln Asn Asn Glu Asp Pro Tyr Thr
1 5

<210> SEQ ID NO 75
<211> LENGTH: 5
<212> TYPE: PRT
<213> ORGANISM: Artificial Sequence
<220> FEATURE:
<223> OTHER INFORMATION: HAPC-14-8 Heavy chain CDR1

<400> SEQUENCE: 75

Phe Tyr Tyr Leu Asn
1 5

<210> SEQ ID NO 76
<211> LENGTH: 19
<212> TYPE: PRT
<213> ORGANISM: Artificial Sequence
<220> FEATURE:
<223> OTHER INFORMATION: HAPC-14-8 Heavy chain CDR2

<400> SEQUENCE: 76

Asp Ile Arg Leu Lys Lys Asn Asn Tyr Glu Lys His Tyr Ala Glu Ser
1 5 10 15

Val Lys Gly

<210> SEQ ID NO 77
<211> LENGTH: 7
<212> TYPE: PRT
<213> ORGANISM: Artificial Sequence
<220> FEATURE:
<223> OTHER INFORMATION: HAPC-14-8 Heavy chain CDR3

<400> SEQUENCE: 77

Glu Gly Asp Thr Phe Asp Tyr
1 5

<210> SEQ ID NO 78
<211> LENGTH: 15
<212> TYPE: PRT
<213> ORGANISM: Artificial Sequence
<220> FEATURE:
<223> OTHER INFORMATION: HAPC-14-8 Light chain CDR1

<400> SEQUENCE: 78

Arg Ala Ser Glu Ser Val Asp Ser Phe Gly Ala Thr Phe Met His
1 5 10 15

<210> SEQ ID NO 79
<211> LENGTH: 7
<212> TYPE: PRT
<213> ORGANISM: Artificial Sequence
<220> FEATURE:
<223> OTHER INFORMATION: HAPC-14-8 Light chain CDR2

<400> SEQUENCE: 79

Leu Ala Ser Arg Leu Gly Ser
1 5

<210> SEQ ID NO 80
<211> LENGTH: 9
<212> TYPE: PRT
<213> ORGANISM: Artificial Sequence
<220> FEATURE:
<223> OTHER INFORMATION: HAPC-14-8 Light chain CDR3

<400> SEQUENCE: 80

Val Gln Asn Asn Glu Asp Pro Tyr Thr
1 5

<210> SEQ ID NO 81
<211> LENGTH: 5
<212> TYPE: PRT
<213> ORGANISM: Artificial Sequence
<220> FEATURE:
<223> OTHER INFORMATION: HAPC-14-9 Heavy chain CDR1

<400> SEQUENCE: 81

Phe Tyr Tyr Leu Asn
1 5

<210> SEQ ID NO 82
<211> LENGTH: 19
<212> TYPE: PRT
<213> ORGANISM: Artificial Sequence
<220> FEATURE:
<223> OTHER INFORMATION: HAPC-14-9 Heavy chain CDR2

<400> SEQUENCE: 82

Asp Ile Arg Leu Lys Lys Asn Asn Tyr Glu Lys His Tyr Ala Glu Ser
1 5 10 15

Val Lys Gly

<210> SEQ ID NO 83
<211> LENGTH: 7
<212> TYPE: PRT
<213> ORGANISM: Artificial Sequence
<220> FEATURE:
<223> OTHER INFORMATION: HAPC-14-9 Heavy chain CDR3

<400> SEQUENCE: 83

Glu Gly Asp Thr Phe Asp Tyr
1 5

<210> SEQ ID NO 84
<211> LENGTH: 15
<212> TYPE: PRT
<213> ORGANISM: Artificial Sequence
<220> FEATURE:
<223> OTHER INFORMATION: HAPC-14-9 Light chain CDR1

<400> SEQUENCE: 84

Arg Ala Ser Glu Ser Val Asp Ser Phe Gly Ala Thr Phe Met His
1 5 10 15

<210> SEQ ID NO 85
<211> LENGTH: 7
<212> TYPE: PRT
<213> ORGANISM: Artificial Sequence
<220> FEATURE:
<223> OTHER INFORMATION: HAPC-14-9 Light chain CDR2

<400> SEQUENCE: 85

```
Leu Ala Ser Arg Leu Gly Ser
1               5
```

<210> SEQ ID NO 86
<211> LENGTH: 9
<212> TYPE: PRT
<213> ORGANISM: Artificial Sequence
<220> FEATURE:
<223> OTHER INFORMATION: HAPC-14-9 Light chain CDR3

<400> SEQUENCE: 86

```
Gln Gln Asn Asn Glu Asp Pro Tyr Thr
1               5
```

<210> SEQ ID NO 87
<211> LENGTH: 5
<212> TYPE: PRT
<213> ORGANISM: Artificial Sequence
<220> FEATURE:
<223> OTHER INFORMATION: HAPC-14-10 Heavy chain CDR1

<400> SEQUENCE: 87

```
Asn Tyr Tyr Leu Asn
1               5
```

<210> SEQ ID NO 88
<211> LENGTH: 19
<212> TYPE: PRT
<213> ORGANISM: Artificial Sequence
<220> FEATURE:
<223> OTHER INFORMATION: HAPC-14-10 Heavy chain CDR2

<400> SEQUENCE: 88

```
Asp Ile Arg Leu Lys Lys Asn Asn Tyr Glu Lys His Tyr Ala Glu Ser
1               5                   10                  15

Val Lys Gly
```

<210> SEQ ID NO 89
<211> LENGTH: 7
<212> TYPE: PRT
<213> ORGANISM: Artificial Sequence
<220> FEATURE:
<223> OTHER INFORMATION: HAPC-14-10 Heavy chain CDR3

<400> SEQUENCE: 89

```
Glu Gly Asp Thr Phe Asp Tyr
1               5
```

<210> SEQ ID NO 90
<211> LENGTH: 15
<212> TYPE: PRT
<213> ORGANISM: Artificial Sequence
<220> FEATURE:
<223> OTHER INFORMATION: HAPC-14-10 Light chain CDR1

<400> SEQUENCE: 90

```
Arg Ala Ser Glu Ser Val Asp Ser Phe Gly Ala Thr Phe Met His
```

-continued

```
1               5                   10                  15


<210> SEQ ID NO 91
<211> LENGTH: 15
<212> TYPE: PRT
<213> ORGANISM: Artificial Sequence
<220> FEATURE:
<223> OTHER INFORMATION: HAPC-14-10 Light chain CDR2

<400> SEQUENCE: 91

Arg Ala Ser Glu Ser Val Asp Ser Phe Gly Ala Thr Phe Met His
1               5                   10                  15


<210> SEQ ID NO 92
<211> LENGTH: 9
<212> TYPE: PRT
<213> ORGANISM: Artificial Sequence
<220> FEATURE:
<223> OTHER INFORMATION: HAPC-14-10 Light chain CDR3

<400> SEQUENCE: 92

Val Gln Asn Asn Glu Asp Pro Tyr Thr
1               5


<210> SEQ ID NO 93
<211> LENGTH: 7
<212> TYPE: PRT
<213> ORGANISM: Artificial Sequence
<220> FEATURE:
<223> OTHER INFORMATION: R2-25G5 Light chain CDR2

<400> SEQUENCE: 93

Leu Ala Ser Trp Leu Pro Ser
1               5


<210> SEQ ID NO 94
<211> LENGTH: 7
<212> TYPE: PRT
<213> ORGANISM: Artificial Sequence
<220> FEATURE:
<223> OTHER INFORMATION: R2-29D9 Light chain CDR2

<400> SEQUENCE: 94

Leu Ala Ser Arg Leu Pro Ser
1               5
```